US008680182B2

(12) United States Patent
Jin et al.

(10) Patent No.: US 8,680,182 B2
(45) Date of Patent: Mar. 25, 2014

(54) METHODS FOR PROMOTING THE REVASCULARIZATION AND REENERVATION OF CNS LESIONS

(75) Inventors: Xing Jin, Charleston, SC (US); Xuejun Wen, Charleston, SC (US); Vibhor Krishna, Charleston, SC (US); Ning Zhang, Charleston, SC (US)

(73) Assignees: Clemson University Research Foundation, Clemson, SC (US); MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 13/447,041

(22) Filed: Apr. 13, 2012

(65) Prior Publication Data

US 2012/0282324 A1    Nov. 8, 2012

Related U.S. Application Data

(63) Continuation-in-part of application No. 12/794,556, filed on Jun. 4, 2010, now Pat. No. 8,481,067.

(60) Provisional application No. 61/184,163, filed on Jun. 4, 2009.

(51) Int. Cl.
| | |
|---|---|
| *A01N 25/08* | (2006.01) |
| *A61F 2/44* | (2006.01) |
| *A61L 27/52* | (2006.01) |
| *A61L 27/54* | (2006.01) |
| *A61L 27/58* | (2006.01) |
| *A61L 15/32* | (2006.01) |

(52) U.S. Cl.
USPC ............... 524/9; 424/409; 424/422; 424/423; 424/425; 424/444; 424/456; 424/499; 424/78.05; 424/78.08; 424/1.45; 524/916

(58) Field of Classification Search
None
See application file for complete search history.

(56) References Cited

U.S. PATENT DOCUMENTS

| | | | |
|---|---|---|---|
| 7,051,654 | B2 | 5/2006 | Boland et al. |
| 7,101,857 | B2 | 9/2006 | Sung et al. |
| 7,282,220 | B1 | 10/2007 | Sung et al. |
| 7,468,192 | B2 | 12/2008 | Mizuno et al. |
| 7,485,617 | B1 | 2/2009 | Pohl et al. |
| 7,786,074 | B2 | 8/2010 | Gourdie et al. |
| 7,828,539 | B1 | 11/2010 | Beachley et al. |
| 7,888,319 | B2 | 2/2011 | Gourdie et al. |
| 7,914,819 | B1 | 3/2011 | Wen et al. |
| 8,124,001 | B1 | 2/2012 | Wen et al. |
| 2003/0175410 | A1 | 9/2003 | Campbell et al. |
| 2003/0198619 | A1 | 10/2003 | Dong et al. |
| 2004/0018295 | A1 | 1/2004 | Qiu et al. |
| 2005/0019404 | A1 | 1/2005 | Sung et al. |
| 2005/0171616 | A1 | 8/2005 | Sung et al. |
| 2006/0149392 | A1 | 7/2006 | Hsieh et al. |
| 2006/0257368 | A1 | 11/2006 | Wen |
| 2007/0077270 | A1 | 4/2007 | Wen |
| 2008/0097606 | A1 | 4/2008 | Cragg et al. |
| 2008/0213238 | A1 | 9/2008 | Gandy et al. |
| 2008/0213334 | A1 | 9/2008 | Lockwood et al. |
| 2010/0015068 | A1 | 1/2010 | Karp et al. |
| 2011/0038921 | A1 | 2/2011 | Wen et al. |
| 2011/0091550 | A1 | 4/2011 | Zhang et al. |

FOREIGN PATENT DOCUMENTS

| | | |
|---|---|---|
| WO | WO 02/102429 A1 | 12/2002 |
| WO | WO 03/040235 A1 | 5/2003 |
| WO | WO 2008/105791 A2 | 9/2008 |
| WO | WO 2010/096795 A1 | 8/2010 |
| WO | WO 2010/120757 A2 | 10/2010 |

OTHER PUBLICATIONS

Sharma HS, Annals of the New York Academy of Sciences, 112:95-111, Dec. 2007.*
Nomura et al., Tissue Engineering: part A, 14(5): 649-665, published online Apr. 17, 2008.*
Mao et al., Biomaterials, 24:1621-1629, 2003.*
Agarwal et al. "Stable Nanocolloids of Poorly Soluble Drugs with High Drug Content Prepared Using the Combination of Sonication and Layer-by-Layer Technology" *Journal of Controlled Release* 128:225-260 (2008).
Allen et al. "Clinical relevance of the neurotrophins and their receptors" *Clinical Science* 110:175-191 (2006).
Angele et al. "Characterization of Esterified Hyaluronan-Gelatin Polymer Composites Suitable for Chondrogenic Differentiation of Mesenchymal Stem Cells" *J. Biomed Mater Res* 91A:416-427 (2008).
Awad et al. "Chondrogenic Differentiation of Adipose-Derived Adult Stem Cells in Agarose Alginate and Gelatin Scaffolds" *Biomaterials* 25:3211-3222 (2004).
Barbani et al. "Bioartificial Materials Based on Blends of Collagen and Poly(Acrylic Acid)" *Journal of Applied Polymer Science* 72:971-976 (1999).
Beachley et al. "Effect of Electrospinning Parameters on the Nanofiber Diameter and Length" *Mater Sci Eng C Mater Biol Appl.* 29(3):663-668 (2009).
Beachley et al. "Fabrication of Nanofiber Reinforced Protein Structures for Tissue Engineering" *Mater Sci Eng C Mater Biol Appl.* 29(8):2448-2453 (2009).
Beachley et al. "Polymer Nanofibrous Structures: Fabrication Biofunctionalization and Cell Interactions" *Prog Polym Sci.* 35(7):868-892 (2010).

(Continued)

*Primary Examiner* — Daniel E Kolker
*Assistant Examiner* — Stacey N MacFarlane
(74) *Attorney, Agent, or Firm* — Myers Bigel Sibley & Sajovec, P.A.

(57) ABSTRACT

The present invention provides methods of promoting the revascularization and/or reenervation of central nervous system lesions using an in-situ crosslinkable hydrogel. The present invention also provides methods of treating a spinal cord injury by topically delivering to the spinal cord injury site a vehicle comprising a neurotrophic factor and/or anti-inflammatory agent. Also provided are methods of treating a spinal cord injury by topically administering or delivering a hydrogel to the injury site.

18 Claims, 20 Drawing Sheets

(56) References Cited

OTHER PUBLICATIONS

Beachley et al. "Three Dimensional Aligned Individual Nano-Fibers for Neural Tissue Engineering" *Society for Biomaterials* 33$^{rd}$ Annual Meeting Chicago IL (2007) (Abstract).
Bellamkonda et al. "Hydrogel-based three-dimensional matrix for neural cells" *Journal of Biomedical Materials Research* 29:663-671 (1995).
Cai et al. "Biodegradable Chitosan Scaffolds Containing Microspheres as Carriers for Controlled Transforming Growth Factor-$\beta_1$ Delivery for Cartilage Tissue Engineering" *Chinese Medical Journal* 120(3):197-203 (2007).
Cai et al. "Injectable glycosaminoglycan hydrogels for controlled release of human basic fibroblast growth factor" *Biomaterials* 26:6054-6067 (2005).
Carmeliet. "Angiogenesis in health and disease" *Nature Medicine* 9(6):653-660 (2003).
Cho et al. "Chitosan produces potent neuroprotection and physiological recovery following traumatic spinal cord injury" *The Journal of Experimental Biology* 213:1513-1520 (2010).
Cooke et al. "Effect of rhPDGF-BB Delivery of Mediators of Periodontal Wound Repair" *Tissue Engineering* 12(6):1441-1450 (2006).
Crompton et al. "Polylysine-functionalised thermoresponsive chitosan hydrogel for neural tissue engineering" *Biomaterials* 28:441-449 (2007).
Dash et al. "Kinetic Modeling on Drug Release from Controlled Drug Delivery Systems" *Acta Poloniae Pharmaceutica—Drug Research* 67(3):217-223 (2010).
Decher "Fuzzy Nanoassemblies: Toward Layered Polymeric Multicomposites" *Science* 277:1232-1237 (1997).
Deguchi et al. Implantation of a new porous gelatin-siloxane hybrid into a brain lesion as a potential scaffold for tissue regeneration *Journal of Cerebral Blood Flow & Metabolism* 26:1263-1273 (2006).
Eagle et al. "Axonal Regeneration and Limited Functional Recovery Following Hippocampal Deafferentation" *The Journal of Comparative Neurology* 363:377-388 (1995).
Erggelet et al. Regeneration of Ovine Articular Cartilage Defects by Cell-Free Polymer-Based Implants *Biomaterials* 28:5570-5580 (2007).
Frank et al. "Characterization of DNA Complexes Formed by the Nuclear Receptor Constitutive Androstane Receptor" *The Journal of Biological Chemistry* 278(44):43299-43310 (2003).
Freier et al. "Controlling cell adhesion and degradation of chitosan films by N-acetylation" *Biomaterials* 26:5872-5878 (2005).
Frenkel et al. "Scaffolds for Articular Cartilage Repair" *Annals of Biomedical Engineering* 32(1):26-34 (2004).
Gamez et al. "Photofabricated Gelatin-Based Nerve Conduits: Nerve Tissue Regeneration Potentials" *Cell Transplantation* 13:549-564 (2004).
Gotterbarm et al. "An in vivo Study of a Growth-Factor Enhanced Cell Free Two-Layered Collagen-Tricalcium Phosphate in Deep Osteochondral Defects" *Biomaterials* 27:3387-3395 (2006).
Guo et al. "Novel Gene-Modified-Tissue Engineering of Cartilage Using Stable Transforming Growth Factor-$\beta$1-Transfected Mesenchymal Stem Cells Grown on Chitosan Scaffolds" *Journal of Bioscience and Bioengineering* 103(6):547-556 (2007).
Guo et al. "Porous Chitosan-Gelatin Scaffold Containing Plasmid DNA Encoding Transforming Growth Factor-$\beta$1 for Chondrocytes Proliferation" *Biomaterials* 27:1095-1103 (2006).
Gupta et al. "Fast-gelling injectable blend of hyaluronan and methylcellulose for intrathecal localized delivery to the injured spinal cord" *Biomaterials* 27:2370-2379 (2006).
Hannila et al. "The Role of Cyclic AMP Signaling in Promoting Axonal Regeneration After Spinal Cord Injury" *Experimental Neurology* 209:321-332 (2008).
Hattori et al. "Chondrotinase ABC Enhances Axonal Regeneration Across Nerve Gaps" *Journal of Clinical Neuroscience* 15:185-191 (2008).
Horn et al. "Influence of cross-linked hyaluronic acid hydrogels on neurite outgrowth and recovery from spinal cord injury" *J. Neurosurg Spine* 6:133-140 (2007).
Hou et al. "The repair of brain lesion by implantation of hyaluronic acid hydrogels modified with laminin" *Journal of Neuroscience Methods* 148:60-70 (2005).
Huang et al. "In Vitro Characterization of Chitosan-Gelatin Scaffolds for Tissue Engineering" *Biomaterials* 26(36):7616-7627(2005).
Hunziker et al. "Repair of Partial-Thickness Defects in Articular Cartilage: Cell Recruitment from the Synovial Membrane" *The Journal of Bone and Joint Surgery Inc.* 78-A(5):721-733 (1996).
Imitola et al. Directed migration of neural stem cells to sites of CNS injury by the stromal cell-derived factor 1$\alpha$/CXC chemokine receptor 4 pathway *PNAS* 101(52):18117-18122 (2004).
Inanc et al. "Periodontal Ligament Cellular Structures Engineered with Electrospun Poly(DL-Lactide-co-Glycolide) Nanofibrous Membrane Scaffolds" *Journal of Biomedical Materials Research* 90A:186-195 (2009).
International Preliminary Report on Patentability of International Application No. PCT/US2010/030865 issued Oct. 18, 2011 (9 pages).
International Search Report and Written Opinion of International Application No. PCT/US2010/030865 mailed Dec. 20, 2010 (14 pages).
Jain et al. "In situ gelling hydrogels for conformal repair of spinal cord defects and local delivery of BDNF after spinal cord injury" *Biomaterials* 27:497-504 published online Aug. 15, 2005.
Kim et al. "Porous Chitosan Scaffold Containing Microspheres Loaded with Transforming Growth Factor-Beta1: Implications for Cartilage Tissue Engineering" *Control Release* 91(3):365-374 (2003).
Kim et al. Porous Scaffolds of Gelatin-Hydroxyapatite Nanocomposites Obtained by Biomimetic Approach: Characterization and Antibiotic Drug Release *J. Biomed Mater Res B Appl Biomater* 74(2):686-698 (2005).
Klaver et al. "Bioactive surface for neural electrodes: Decreasing astrocyte proliferation via transforming growth factor-$\beta$1" *J Biomed Mater Res* 81A:1011-1016 (2007).
Kuo et al. "Regeneration of Dentin-Pulp Complex with Cementum and Periodontal Ligament Formation Using Dental Bud Cells in Gelatin-Chondroitin-Hyaluronan Tri-Copolymer Scaffold in Swine" *J Biomed Mater Res* 86(A):1062-1068 (2008).
Kuo et al. "Cartilage Tissue Engineering: Its Potential and Uses" *Curr Opin Rheumatol* 18:64-73 (2006).
Kurth et al. "Chondrogenic Potential of Human Synovial Mesenchymal Stem Cells in Alginate" *OsteoArthritis and Cartilage* 15:1178-1189 (2007).
Kwok et al. "The Anti-Inflammatory Natural Product Parthenolide from the Medicinal Herb Feverfew Directly Binds to and Inhibits IkB Kinase" *Chemistry & Biology* 8:759-766 (2001).
Laurent et al. "The structure and function of hyaluronan: An overview" *Immunol Cell Biol* 74(2):A1-7 (1996).
Leach et al. "Development of photocrosslinkable hyaluronic acid-polyethylene glycol-peptide composite hydrogels for soft tissue engineering" *J Biomed Mater Res* vol. 70A:74-82 (2004).
Lee et al. "Effects of the Controlled-Released TGF-beta 1 from Chitosan Microspheres on Chondrocytes Cultured in a Collagen/Chitosan/Glycosaminoglycan Scaffold" *Biomaterials* 25(18):4163-4173 (2004).
Lu et al. "Collagen scaffolds populated with human marrow stromal cells reduce lesion volume and improve functional outcome after traumatic brain injury" *Neurosurgery* 61(3):596-603 (2007).
Luo et al. "Cross-linked hyaluronic acid hydrogel films: new biomaterials for drug delivery" *Journal of Controlled Release* 69:169-184 (2000).
Lutolf et al. "Repair of Bone Defects Using Synthetic Mimetics of Collagenous Extracellular Matrices" *Nature Biotechnology* 21:513-518 (2003).
Lvov et al. "Converting Poorly Soluble Materials into Stable Aqueous Nanocolloids" *Langmuir* 27(3):1212-1217 (2011).
Mao et al. "The properties of chitosan-gelatin membranes and scaffolds modified with hyaluronic acid by different methods" *Biomaterials* 24:1621-1629 (2003).

(56) References Cited

OTHER PUBLICATIONS

Martino et al. "Chitosan: A Versatile Biopolymer for Orthopaedic Tissue-Engineering" *Biomaterials* 26:5983-5990 (2005).
Matsuda and Magoshi. "Preparation of Vinylated Polysaccharides and Photofabrication of Tubular Scaffolds as Potential Use in Tissue Engineering" *Biomacromolecules* 3:942-950 (2002).
Murphy et al. "Engagement of CD44 modulates cyclooxygenase induction, VEGF generation and proliferation in human vascular endothelial cells" *The FASEB Journal* 19:446-448 (2005).
Nicholas et al. "Denatured Thiolated Collagen" *Biomaterials* 18:807-813 (1997).
Nisbet et al. "Review Neural Tissue Engineering of the CNS Using Hydrogels" *J Biomed Mater Res Part B: Appl Biomater* 87B: 251-263 (2008).
Nomura et al. "Extramedullary Chitosan Channels Promote Survival of Transplanted Neural Stem and Progenitor Cells and Create a Tissue Bridge After Complete Spinal Cord Transection" *Tissue Engineering: Part A* 14(5): 649-665 (published online Apr. 17, 2008).
Okuda et al. "Time-Programmed Dual Release Formulation by Multilayered Drug-Loaded Nanofiber Meshes" *Journal of Controlled Release* 143:258-264 (2010).
Page et al. "The Pathogenesis of Human Periodontitis: an Introduction" *Periodontology* 14:9-11 (1997).
Peattie et al. "Stimulation of in vivo angiogenesis by cytokine-loaded hyaluronic acid hydrogel implants" *Biomaterials* 25:2789-2798 (2004).
Peattie et al. "Dual growth factor-induced angiogenesis in vivo using hyaluronan hydrogel implants" *Biomaterials* 27:1868-1875 (2006).
Pike et al. "Heparin-Regulated Release of Growth Factors In Vitro and Angiogenic Response In Vivo to Implanted Hyaluronan Hydrogels Containing VEGF and bFGF" *Biomaterials* 27:5242-5251 (2006).
Plant et al. "Implantation of Collagen IV/poly(2-hydroxyethyl Methacrylate) Hydrogels Containing Schwann Cells into the Lesioned Rat Optic Tract" *Cell Transplant* 4:381-91 (1998).
Ponticiello et al. "Gelatin-Based Resorbable Sponge as a Carrier Matrix for Human Mesenchymal Stem Cells in Cartilage Regeneration Therapy" *J. Biomed Mater Res* 52:246-255 (2000).
Prestwich et al. "Injectable synthetic extracellular matrices for tissue engineering and repair" *Adv Exp Med Biol* 585:125-133 (2007).
Qiu et al. "Chemically Modified Light-Curable Chitosans with Enhanced Potential for Bone Tissue Repair" *J Biomed Mater Res* 89(A):772-779 (2009).
Qiu et al. "Fabrication of Permeable Tubular Constructs From Chemically Modified Chitosan With Enhanced Antithrombogenic Property" *J Biomed Mater Res Part B: Appl Biomater* 90B:668-678 (2009).
Qiu. "Chitosan Derivatives for Tissue Engineering" Clemson University Ph.D. degree thesis Aug. 2008 (11 pages).
Radice et al. "Hyaluronan-based biopolymers as delivery vehicles for bone-marrow-derived mesenchymal progenitors" *J Biomed Mater Res* vol. 50:101-109 (2000).
Reichardt. "Neurotrophin-regulated signalling pathways" *Phil. Trans. R. Soc. B* 361:1545-1564 (2000).
Riley et al. "Stimulation of in vivo angiogenesis using dual growth factor-loaded crosslinked glycosaminoglycan hydrogels" *Biomaterials* 27(35):5935-5943 (2007).
Sanes."Roles of Extracellular Matrix In Neural Development" *Ann. Rev. Physiol.* 45:581-600 (1983).
Schagemann et al. "Cell-Laden and Cell-Free Biopolymer Hydrogel for the Treatment of Osteochondral Defects in a Sheep Model" *Tissue Engineering* Part A 15(1):75-83 (2009).
Segura et al. "Crosslinked hyaluronic acid hydrogels: a strategy to functionalize and pattern" *Biomaterials* 26:359-371 (2005).
Sharma et al. "A Select Combination of Neurotrophins Enhances Neuroprotection and Functional Recovery following Spinal Cord Injury" *Annals of the New York Academy of Sciences* 112:95-111 (2007).

Shor et al. "Fabrication of Three-Dimensional Polycaprolactone/Hydroxyapatite Tissue Scaffolds and Osteoblast-Scaffold Interactions in vitro" *Biomaterials* 28:5291-5297 (2007).
Shu et al. "Attachment and spreading of fibroblasts on an RGD peptide-modified injectable hyaluronan hydrogel" *J Biomed Mater Res* 68A:365-375 (2004).
Shu et al. "Disulfide Cross-Linked Hyaluronan Hydrogels" *Biomacromolecules* 3:1304-1311 (2002).
Shu et al. "Disulfide-crosslinked hyaluronan-gelatin hydrogel films: a covalent mimic of the extracellular matrix for in vitro cell growth" *Biomaterials* 24:3825-3834 (2003).
Shu et al. "In situ crosslinkable hyaluronan hydrogels for tissue engineering" *Biomaterials* 25:1339-1348 (published online Oct. 14, 2003).
Shu et al. "Synthesis and evaluation of injectable in situ crosslinkable synthetic extracellular matrices for tissue engineering" *J Biomed Mater Res* 79A:902-912 (2006).
Sill et al. "Electrospinning: Applications in Drug Delivery and Tissue Engineering" *Biomaterials* 29:1989-2006 (2008).
Slater et al. "An In Vitro Model of the Glomerular Capillary Wall Using Electrospun Collagen Nanofibres in a Bioartificial Composite Basement Membrane" *PLoS ONE* 6(6):e20802 (2011).
Solchaga et al. "Hyaluronan-based Polymers in the Treatment of Osteochondral Defects" *Journal of Orthopaedic Research* 18(5):773-780 (2000).
Stabenfeldt et al. "Thermoreversible laminin-functionalized hydrogel for neural tissue engineering" *J Biomed Mater Res* 77A:718-725 (2006).
Stoop "Smart Biomaterials for Tissue Engineering of Cartilage" *Injury Int. J. Care Injured* 39S1:77-87 (2008).
Taba et al. "Current Concepts in Periodontal Bioengineering" *Orthod Craniofacial Res* 8:292-302 (2005).
Tamai et al. "A New Biotechnology for Articular Cartilage Repair: Subchondral Implantation of a Composite of Interconnected Porous Hydroxyapatite Synthetic Polymer (PLA-PEG) and Bone Morphogenetic Protein-2 (rhBMP-2)" *OsteoArthritis and Cartilage* 13:405-417 (2005).
Tate et al. "Biocompatibility of methylcellulose-based constructs designed for intracerebral gelation following experimental traumatic brain injury" *Biomaterials* 22:1113-1123 (2001).
Tian et al. "Hyaluronic Acid-Poly-D-Lysine-Based Three-Dimensional Hydrogel for Traumatic Brain Injury" *Tissue Engineering* 11(3-4):513-528 (2005).
Trochon et al. "Evidence of Involvement of CD44 In Endothelial Cell Proliferation Migration And Angiogenesis" In Vitro *Int. J. Cancer* 66:664-668 (1996).
Wade et al. "Efficacy of hypertonic saline dextran (HSD) in patients with traumatic hypotension: meta-analysis of individual patient data" *Acta Anaesthesiol Scand Suppl* 110:77-79 (1997).
Wei et al. "Nano-Fibrous Scaffold for Controlled Delivery of Recombinant Human PDGF-BB" *J Control Release* 112(1):103-110 (2006).
Wei et al. "Hyaluronic acid hydrogels with IKVAV peptides for tissue repair and axonal regeneration in an injured rat brain" *Biomed. Mater.* 2:S142-S146 (2007).
Wells et al. "Gel Matrix Vehicles for Growth Factor Application in Nerve Gap Injuries Repaired with Tubes: A Comparison of Biomatrix Collagen and Methylcellulose" *Experimental Neurology* 146:395-402 (1997).
Wen "Regeneration of Cartilage In Vivo Without Cell Transplantation: A Bioengineering Strategy" Program for South Carolina Science Technology and Health Conference and 2009 Annual Meeting of the South Carolina Academy of Science Apr. 14-15, 2009.
Wissink et al. "Binding and release of basic fibroblast growth factor from heparinized collagen matrices" *Biomaterials* 22:2291-2299 (2001).
Wissink et al. "Immobilization of heparin to EDC/NHS-crosslinked collagen. Characterization and in vitro evaluation" *Biomaterials* 22:151-163 (2001).
Woerly et al. "Neural Tissue Formation Within Porous Hydrogels Implanted in Brain and Spinal Cord Lesions: Ultrastructural Immunohistochemical and Diffusion Studies" *Tissue Eng* 5(5):467-488 (1999).

(56) References Cited

OTHER PUBLICATIONS

Wong et al. "Effect of Naringin on Bone Cells" *Journal of Orthopaedic Research* 24:2045-2050 (2006).

Wood et al. "Controlling Interlayer Diffusion to Achieve Sustained Multiagent Delivery from Layer-by-Layer Thin Films" *PNAS* 103(27):10207-10212 (2006).

Yang et al. "Nanofiber Enabled Layer-by-Layer Approach toward Three-Dimensional Tissue Formation" *Tissue Engineering* 15(4):945-956 (2009).

Zhang et al, "Three-Dimensional Nanohydroxyapatite/Chitosan Scaffolds as Potential Tissue Engineered Periodontal Tissue" *Journal of Biomaterials Applications* 21:333-349 (2007).

Zhang et al. "Drug-Loaded Degradable Nano-Particles for the Rescue of Tissue Under Hypoxia Condition and Promote Angiogenesis" $229^{th}$ ACS National Meeting San Diego CA Mar. 13, 2005.

Zhang et al. "Synthesis and characterization of biocompatible degradable light-curable polyurethane-based elastic hydrogels" *J Biomed Mater Res* 82A:637-650 (2007).

Zhang et al. "Fabrication of semipermeable hollow fiber membranes with highly aligned texture for nerve guidance" *J Biomed Mater Res* 75A:941-949 (2005).

Zhang et al. "Tissue-engineering approaches for axonal guidance" *Brain Research Reviews* 49:48-64 (2005)(abstract).

Zhao et al. "Recruitment of Endogenous Stem Cells for Tissue Repair" *Macromol. Biosci.* 8:836-842 (2008).

Zhong et al. "Controlled release of anti-inflammatory agent α-MSH from neural implants" *Journal of Controlled Release* 106:309-318 (2005).

Krishna et al. "A systematic review of predictors of functional outcomes utilizing neuronal bridge composed of biodegradable polymer, supporting cells and neurotrophic factors" Abstract for American Association of Neurological Surgeons Annual Meeting, Denver, Colorado, Apr. 9-13, 2011 (1 Page).

Krishna et al. "Functional outcomes after injection of chitosan-gelatin hydrogel for in a rat model of severe spinal cord injury", Poster presentation at Medical University of South Carolina, Charleston, South Carolina. May 5, 2011 (Abstract and poster, 2 pages).

Krishna et al. "Functional outcomes after topical application of chitosan-gelatin hydrogel for in a rat model of severe spinal cord injury" Poster presentation at Medical University of South Carolina, Charleston, South Carolina, May 5, 2011 (Abstract and poster, 2 pages).

Krishna et al., "Functional outcomes after application of chitosan-gelatin hydrogel in a rat model of severe spinal cord injury", Abstract and eposter for American Association of Neurological Surgeons Annual Meeting, Miami, Florida, Apr. 14-18, 2012; poster available online Apr. 1, 2012 (11 pages).

\* cited by examiner 3 mm at low magnification, 300 µm at high magnification 3 mm at low magnification, 300 μm at high magnification

```
                        SEQUENCE LISTING

<160> NUMBER OF SEQ ID NOS: 14

<210> SEQ ID NO 1
<211> LENGTH: 25
<212> TYPE: PRT
<213> ORGANISM: Artificial
<220> FEATURE:
<223> OTHER INFORMATION: Laminin-derived short peptide sequence

<400> SEQUENCE: 1

Cys Asp Pro Val Cys Cys Gly Thr Ala Arg Pro Gly Tyr Ile Gly Ser
1               5                   10                  15

Arg Gly Thr Ala Arg Cys Cys Ala Cys
            20                  25

<210> SEQ ID NO 2
<211> LENGTH: 12
<212> TYPE: PRT
<213> ORGANISM: Artificial
<220> FEATURE:
<223> OTHER INFORMATION: Laminin-derived peptide sequence

<400> SEQUENCE: 2

Cys Cys Arg Arg Ile Lys Val Ala Val Trp Leu Cys
1               5                   10

<210> SEQ ID NO 3
<211> LENGTH: 13
<212> TYPE: PRT
<213> ORGANISM: Artificial
<220> FEATURE:
<223> OTHER INFORMATION: Laminin-derived peptide sequence

<400> SEQUENCE: 3

Cys Cys Arg Arg Tyr Val Val Leu Pro Arg Trp Leu Cys
1               5                   10

<210> SEQ ID NO 4
<211> LENGTH: 16
<212> TYPE: PRT
<213> ORGANISM: Artificial
<220> FEATURE:
<223> OTHER INFORMATION: Laminin-derived peptide sequence

<400> SEQUENCE: 4

Cys Cys Arg Arg Asn Ile Ala Glu Ile Ile Lys Asp Ile Trp Leu Cys
1               5                   10                  15

<210> SEQ ID NO 5
<211> LENGTH: 12
<212> TYPE: PRT
<213> ORGANISM: Artificial
<220> FEATURE:
<223> OTHER INFORMATION: Laminin-derived peptide sequence

<400> SEQUENCE: 5

Cys Cys Arg Arg Tyr Ile Gly Ser Arg Trp Leu Cys
1               5                   10
```

<210> SEQ ID NO 6
<211> LENGTH: 25
<212> TYPE: PRT
<213> ORGANISM: Artificial
<220> FEATURE:
<223> OTHER INFORMATION: Laminin-derived peptide sequence

<400> SEQUENCE: 6

Cys Asp Pro Val Cys Cys Gly Thr Ala Arg Pro Gly Tyr Ile Gly Ser
1               5                   10                  15

Arg Gly Thr Ala Arg Cys Cys Ala Cys
            20                  25

<210> SEQ ID NO 7
<211> LENGTH: 29
<212> TYPE: PRT
<213> ORGANISM: Artificial
<220> FEATURE:
<223> OTHER INFORMATION: Laminin-derived peptide sequence

<400> SEQUENCE: 7

Cys Asp Pro Val Cys Cys Gly Thr Ala Arg Pro Gly Asn Ile Ala Glu
1               5                   10                  15

Ile Ile Lys Asp Ile Gly Thr Ala Arg Cys Cys Ala Cys
            20                  25

<210> SEQ ID NO 8
<211> LENGTH: 26
<212> TYPE: PRT
<213> ORGANISM: Artificial
<220> FEATURE:
<223> OTHER INFORMATION: Laminin-derived peptide sequence

<400> SEQUENCE: 8

Cys Asp Pro Val Cys Cys Gly Thr Ala Arg Pro Gly Tyr Val Val Leu
1               5                   10                  15

Pro Arg Gly Thr Ala Arg Cys Cys Ala Cys
            20                  25

<210> SEQ ID NO 9
<211> LENGTH: 25
<212> TYPE: PRT
<213> ORGANISM: Artificial
<220> FEATURE:
<223> OTHER INFORMATION: Laminin-derived peptide sequence

<400> SEQUENCE: 9

Cys Asp Pro Val Cys Cys Gly Thr Ala Arg Pro Gly Ile Lys Val Ala
1               5                   10                  15

Val Gly Thr Ala Arg Cys Cys Ala Cys
            20                  25

<210> SEQ ID NO 10
<211> LENGTH: 14
<212> TYPE: PRT
<213> ORGANISM: Artificial
<220> FEATURE:
<223> OTHER INFORMATION: Fibronectin-derived peptide sequence

<400> SEQUENCE: 10

Cys Cys Arg Arg Gly Arg Gly Asp Ser Pro Lys Trp Leu Cys
1               5                   10

<210> SEQ ID NO 11

```
<211> LENGTH: 19
<212> TYPE: PRT
<213> ORGANISM: Artificial
<220> FEATURE:
<223> OTHER INFORMATION: Fibronectin-derived peptide sequence

<400> SEQUENCE: 11

Cys Cys Arg Arg Ala Val Thr Gly Arg Gly Asp Ser Pro Ala Ser Ser
1               5                   10                  15

Trp Leu Cys

<210> SEQ ID NO 12
<211> LENGTH: 32
<212> TYPE: PRT
<213> ORGANISM: Artificial
<220> FEATURE:
<223> OTHER INFORMATION: Fibronectin-derived peptide sequence

<400> SEQUENCE: 12

Cys Asp Pro Val Cys Cys Gly Thr Ala Arg Pro Gly Pro Gln Val Thr
1               5                   10                  15

Arg Gly Asp Val Phe Thr Met Pro Gly Thr Ala Arg Cys Cys Ala Cys
                20                  25                  30

<210> SEQ ID NO 13
<211> LENGTH: 23
<212> TYPE: PRT
<213> ORGANISM: Artificial
<220> FEATURE:
<223> OTHER INFORMATION: Fibronectin-derived peptide sequence

<400> SEQUENCE: 13

Cys Asp Pro Val Cys Cys Gly Thr Ala Arg Pro Gly Arg Gly Asp Gly
1               5                   10                  15

Thr Ala Arg Cys Cys Ala Cys
                20

<210> SEQ ID NO 14
<211> LENGTH: 19
<212> TYPE: PRT
<213> ORGANISM: Artificial
<220> FEATURE:
<223> OTHER INFORMATION: Vitronectin-derived peptide sequence

<400> SEQUENCE: 14

Cys Cys Arg Arg Pro Gln Val Thr Arg Gly Asp Val Phe Thr Met Pro
1               5                   10                  15

Trp Leu Cys
```

METHODS FOR PROMOTING THE REVASCULARIZATION AND REENERVATION OF CNS LESIONS

STATEMENT OF PRIORITY

The present application is a continuation-in-part application of, and claims priority to, U.S. application Ser. No. 12/794,556, filed Jun. 4, 2010 now U.S. Pat. No. 8,481,067, which claims the benefit, under 35 U.S.C. §119(e), of U.S. Provisional Application No. 61/184,163, filed Jun. 4, 2009, the entire contents of each of which are incorporated by reference herein.

STATEMENT OF GOVERNMENT SUPPORT

Aspects of this invention were supported by government funding under Grant Nos. R01 NS050243 and P20RR021949 from the National Institutes of Health and Grant Nos. SC090380 and PT073600 from the Department of Defense. The U.S. Government has certain rights in this invention.

STATEMENT REGARDING ELECTRONIC FILING OF A SEQUENCE LISTING

A Sequence Listing in ASCII text format, submitted under 37 C.F.R. §1.821, entitled 9662-4IP_$_{ST}$25.txt, 4,585 bytes in size, generated on Jul. 20, 2012 and filed via EFS-Web, is provided in lieu of a paper copy. This Sequence Listing is incorporated herein by reference into the specification for its disclosures.

FIELD OF THE INVENTION

The present invention relates to methods of treating central nervous system lesions, including promoting revascularization and/or reenervation. The present invention also relates to treating spinal cord injury, including reducing inhibition of axonal regeneration and/or decreasing secondary injury at a spinal cord injury site.

BACKGROUND OF THE INVENTION

Brain stroke ranks as the third leading cause of death and disability in most developed countries (Wolfe et al., *J. Neurol. Neurosurg. Psychiatry* 72:211 (2002), and is the second most common cause of death worldwide (Murray et al., *Lancet* 349:1269 (1997)). About ⅙ of all human beings will suffer at least one stroke in their lives (Seshadri et al., *Stroke* 37:345 (2006)). Stroke can be hemorrhagic, ischemic, or embolic in origin. Each year, 500,000 new cases of brain strokes are reported in the US (Higashida et al., *Am. J. Neuroradiol.* 26:2323 (2005)). Depending upon the particular cerebral vessels involved, stroke patients may have a one-year mortality rate ranging from 60% to 8% (Murray et al., *Lancet* 349:1269 (1997); Salgado et al., *Stroke* 27:661 (1996)). Nonetheless, the surviving stroke patients usually remain severely disabled and require constant care for the rest of their lives.

Despite tremendous effort in thrombolysis and neuroprotection, no effective treatment is available for cerebral stroke in clinical settings. This is largely due to the inability of current treatments to repopulate the stroke lesion cavity with functional neurons and glial cells, which dynamically participate in cell-cell signaling and provide sustained trophic support that is critical for decreased neural degeneration and sustained functional recovery. In support of this notion, neural transplantation strategies have been developed to reconstruct the stroke lesion cavity. Despite its efficacy in providing sustained functional recovery in other types of central nervous system (CNS) injuries, neural transplantation for cerebral stroke repair has had limited success, due to poor donor cell survival and functionality at the infarct site (Savitz et al., *NeuroRx* 1:406 (2004)).

An accumulating body of evidence has indicated the predominant role of glial scar tissue in obstructing brain tissue regeneration and structural repair following stroke (Lipton, *Physiol. Rev.* 79:1431 (1999); Gartshore et al., *Exp. Neurol.* 147:353 (1997)). The dense scar tissue outlining a stroke lesion cavity typically consists of endogenous and/or hematogenous inflammatory cells embedded within a dense, remodeling extracellular matrix (Fitch et al., *J. Neurosci.* 19:8182 (1999); Lindsay, Reactive gliosis. In: Fedoroff S, Vernadakis A, editors. *Astrocytes* Orlando: Academic Press; 1986. pp. 231-262; Preston et al., *J. Neurotrauma* 18:83 (2001)). The presence of the scar tissue not only contributes to regenerative failure, but also to the poor survival and functionality of transplanted cells, and poses a diffusive barrier that hinders the effective delivery of nutrients, oxygen, and pharmacological agents into the lesion cavity.

Since any reparative therapy designed to regenerate brain tissue following a stroke will take place in the lesion site, there is a critical need for strategies to overcome the inhibitory scar and promote neuronal regeneration and reconstruction across the lesion cavity. Most importantly, a well-structured vasculature network that completely re-fills the stroke lesion cavity is a prerequisite to support the brain tissue regeneration process.

Spinal cord injury (SCI) continues to affect a significant number of individuals, especially those in the 18-50 age group (National Spinal Cord Injury Statistical Center (NSCISC) "Spinal Cord Injury Facts and Figures at a Glance" Birmingham: University of Alabama (2010). The injury process involves primary and secondary components (Fehlings et al. "Current status of clinical trials for acute spinal cord injury" *Injury* 36 Suppl 2:B113-22 (2005); Hall et al. "Neuroprotection and acute spinal cord injury: a reappraisal" *Neurorx* 1(1):80-100 (2004); Onose et al. "A review of published reports on neuroprotection in spinal cord injury" *Spinal Cord* 47(10):716-26 (2009). Primary injury occurs immediately after trauma and mainly involves axonal loss at the injury epicenter. Subsequent local inflammation induces secondary injury from the release of cytokines, activation of microglia, and post-traumatic ischemia (Tator et al. "Review of the secondary injury theory of acute spinal cord trauma with emphasis on vascular mechanisms. *J Neurosurg* 75(1):15-26 (1991). Secondary injury leads to delayed necrosis and apoptosis resulting in further neuronal loss. In efforts to minimize secondary injury, several neuroprotection strategies have been investigated in randomized control trials. The most notable among these trials were the first and second National Acute Spinal Cord Injury Studies (NASCIS) (Bracken et al. "Efficacy of methylprednisolone in acute spinal cord injury" *JAMA* 251(1):45-52 (1984); Bracken et al. "A randomized, controlled trial of methylprednisolone or naloxone in the treatment of acute spinal-cord injury. Results of the Second National Acute Spinal Cord Injury Study" *N. Engl. J. Med.* 322(20):1405-11 (1990). The results from both these trials, as well as many subsequent studies focusing on the different treatment strategies, have shown no benefit in secondary injury prevention.

The present invention overcomes these shortcomings by providing methods for promoting revascularization and/or reenervation of CNS lesions and for treating spinal cord injury. The methods may be accompanied by removal of existing scar tissue and/or prevention of scar tissue formation.

SUMMARY OF THE INVENTION

One aspect of the present invention relates to methods of promoting revascularization in a CNS lesion, comprising delivering to the lesion an amount of a hydrogel of this invention effective to promote revascularization of the lesion. In one embodiment, the hydrogel does not comprise any angiogenic factors.

A further aspect of the present invention relates to methods of promoting revascularization and reenervation of a CNS lesion and/or repair/regeneration of a CNS lesion, comprising delivering to the lesion an amount of a hydrogel of this invention effective to promote revascularization and reenervation of the lesion.

A further aspect of the present invention relates to methods of recruiting neural stem cells to a CNS lesion, comprising delivering a hydrogel of this invention that contains at least one neural stem cell recruiting factor to the lesion in an amount effective to promote both revascularization of the lesion and recruitment of neural stem cells to the lesion. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one neural stem cell recruiting factor and neurogenic factor to the lesion in an amount effective to promote both revascularization of the lesion and repopulation of the lesion with functional neurons. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one mitogen for neural stem cell proliferation/expansion to the lesion in an amount effective to promote both revascularization of the lesion and repopulation of the lesion with functional neurons. In some embodiments, the mitogen for neural stem cells is selected from the group consisting of EGF, FGF-2, PDGF and any combination thereof in any ratio.

A further aspect of the present invention relates to methods of repopulating a CNS lesion with functional neurons, comprising delivering a hydrogel of this invention that contains at least one neural differentiation factor to the lesion in an amount effective to promote both revascularization of the lesion and repopulation of the lesion with functional neurons. In certain embodiments, the neural differentiation factor is selected from the group consisting of BDNF, NT-3, GDNF, CNTF and any combination thereof in any ratio.

A further aspect of the present invention relates to methods of repopulating a CNS lesion with functional neurons, comprising delivering a hydrogel of this invention to the lesion in an amount effective to promote revascularization of the lesion, and delivering at least one neural stem cell mobilizing factor to the central nervous system (CNS) of the subject having the lesion. In certain embodiments, the neural stem cell mobilizing factor is delivered to the subventricular zone. In some embodiments, the neural stem cell mobilizing factor is selected from the group consisting of leukemia inhibitory factor, granulocyte-colony stimulating factor and any combination thereof in any ratio.

A further aspect of the present invention relates to methods of repopulating a CNS lesion with functional neurons, comprising: delivering a hydrogel of this invention to the lesion in an amount effective to promote revascularization of the lesion, and delivering both a neural stem cell recruiting factor and a neural stem cell mobilizing factor to the CNS of the subject having the lesion. In certain embodiments, the neural stem cell recruiting factor is present in the hydrogel and the neural stem cell mobilizing factor is delivered to the subventricular zone. In other embodiments, the neural stem cell recruiting factor is hepatocyte growth factor and the neural stem cell mobilizing factor is leukemia inhibitory factor.

A further aspect of the present invention relates to methods of repairing a CNS lesion, comprising delivering to the lesion an amount of a hydrogel of this invention effective to promote the revascularization and reenervation of the lesion, thereby repairing the CNS lesion.

A further aspect of the present invention relates to methods of treating a disorder resulting from a CNS lesion, comprising delivering to the lesion an amount of a hydrogel of this invention effective to promote the revascularization and reenervation of the lesion and to treat at least one symptom of the disorder resulting from the CNS lesion.

A further aspect of the present invention relates to methods of preventing scar tissue growth in a CNS lesion, comprising delivering to the lesion an amount of a hydrogel of this invention comprising at least one agent that blocks the biosynthesis of inhibitory ECM components, wherein said amount is effective to prevent scarring. In certain embodiments, the agent is selected from the group consisting of p-nitrophenyl-b-D-xylopyranoside, dimethyloxalylglycine, cyclic nucleotides, and any combinations thereof in any ratio.

A further aspect of the present invention relates to methods of digesting scar tissue in a CNS lesion, comprising delivering to the lesion an amount of a hydrogel of this invention comprising at least one ECM-degrading enzyme, wherein said amount is effective to digest scar tissue. In certain embodiments, the enzyme is selected from the group consisting of chondroitinase ABC, collagenase IV, and any combination thereof in any ratio.

A further aspect of the present invention relates to methods of maintaining a scar-reduced environment in a CNS lesion, comprising delivering to the lesion site an amount of a hydrogel of this invention comprising at least one agent that blocks the biosynthesis of inhibitory ECM components and/or reduces recruitment of inflammatory cells to the lesion site and/or reduces activity of inflammatory cells at the lesion site and, optionally, at least one ECM-degrading enzyme, wherein said amount is effective to maintain a scar-reduced environment at the lesion site. In certain embodiments, the agent can be, e.g., p-nitrophenyl-b-D-xylopyranoside, dimethyloxalylglycine, cyclic nucleotides, and any combination thereof, and the enzyme can be chondroitinase ABC, collagenase IV, and any combination thereof.

A further aspect of the invention is a method of treating a spinal cord injury, comprising topically delivering to the spinal cord injury site an amount of a neurotrophic factor and/or an anti-inflammatory agent effective to treat the spinal cord injury.

Also provided herein is a method of reducing inhibition of axonal regeneration at a spinal cord injury site, comprising topically delivering to the site an amount of a neurotrophic factor and/or an anti-inflammatory agent effective in reducing inhibition of axonal regeneration at the spinal cord injury site.

Another aspect of this invention is a method of decreasing secondary injury at a spinal cord injury site, comprising topically delivering to the site an amount of a neurotrophic factor and/or an anti-inflammatory agent effective in decreasing secondary injury at the spinal cord injury site.

In additional aspects, the present invention provides a method of delivering a neurotrophic factor and/or an anti-inflammatory agent to a spinal cord injury site, comprising topically delivering to the spinal cord injury site a vehicle comprising the neurotrophic factor and/or anti-inflammatory agent, wherein the vehicle is selected from the group consisting of a hydrogel, a nanosphere, microsphere, membrane, scaffold or any combination thereof, thereby delivering the neurotrophic factor and/or the anti-inflammatory agent to the spinal cord injury site.

A further aspect is a method of preventing or reducing scar tissue growth at a spinal cord injury site, comprising topically delivering to the site an effective amount of at least one agent that blocks the biosynthesis of inhibitory extracellular matrix components and/or reduces recruitment of inflammatory cells to the site and/or reduces activity of inflammatory cells, thereby preventing or reducing scar tissue growth at the spinal cord injury site.

The present invention also provides a method of recruiting stem cells to a spinal cord injury site, comprising topically delivering to the site at least one neural stem cell recruiting factor.

In a further aspect, the present invention provides a method of treating a spinal cord injury, comprising topically delivering to the spinal cord injury site an amount of a chitosan-gelatin based hydrogel effective to treat the spinal cord injury.

Also provided herein is a method of reducing inhibition of axonal regeneration at a spinal cord injury site, comprising topically delivering to the site an amount of a chitosan-gelatin based hydrogel effective in reducing inhibition of axonal regeneration at the spinal cord injury site.

Another aspect of this invention is a method of decreasing secondary injury at a spinal cord injury site, comprising topically delivering to the site an amount of a chitosan-gelatin based hydrogel effective in decreasing secondary injury at the spinal cord injury site.

These and other aspects of the present invention will be discussed in more detail in the description of the invention set forth below.

BRIEF DESCRIPTION OF THE FIGURES

FIGS. 5A, 5C, 5D. Adult rat brain four weeks after focal ischemic stroke (untreated). FIGS. 5B, 5E, 5F. Adult rat brain treated with an in-situ crosslinkable hydrogel four weeks after focal ischemic stroke. FIGS. 5A-5B depict the gross morphology of the brains. FIGS. 5C, 5E contain mosaic image reconstructions of the lesions. Higher resolution images of the lesion interfaces are provided in FIGS. 5D and 5F. Light grey corresponds to GFAP staining for astrocytes. Dark grey represents Reca-1 staining for blood vessels. As shown in panel E, a well-structured vasculature network was rebuilt at the lesion injected with the in-situ crosslinkable hydrogel of the present invention.

DETAILED DESCRIPTION OF THE INVENTION

Figures 1A, 1B:
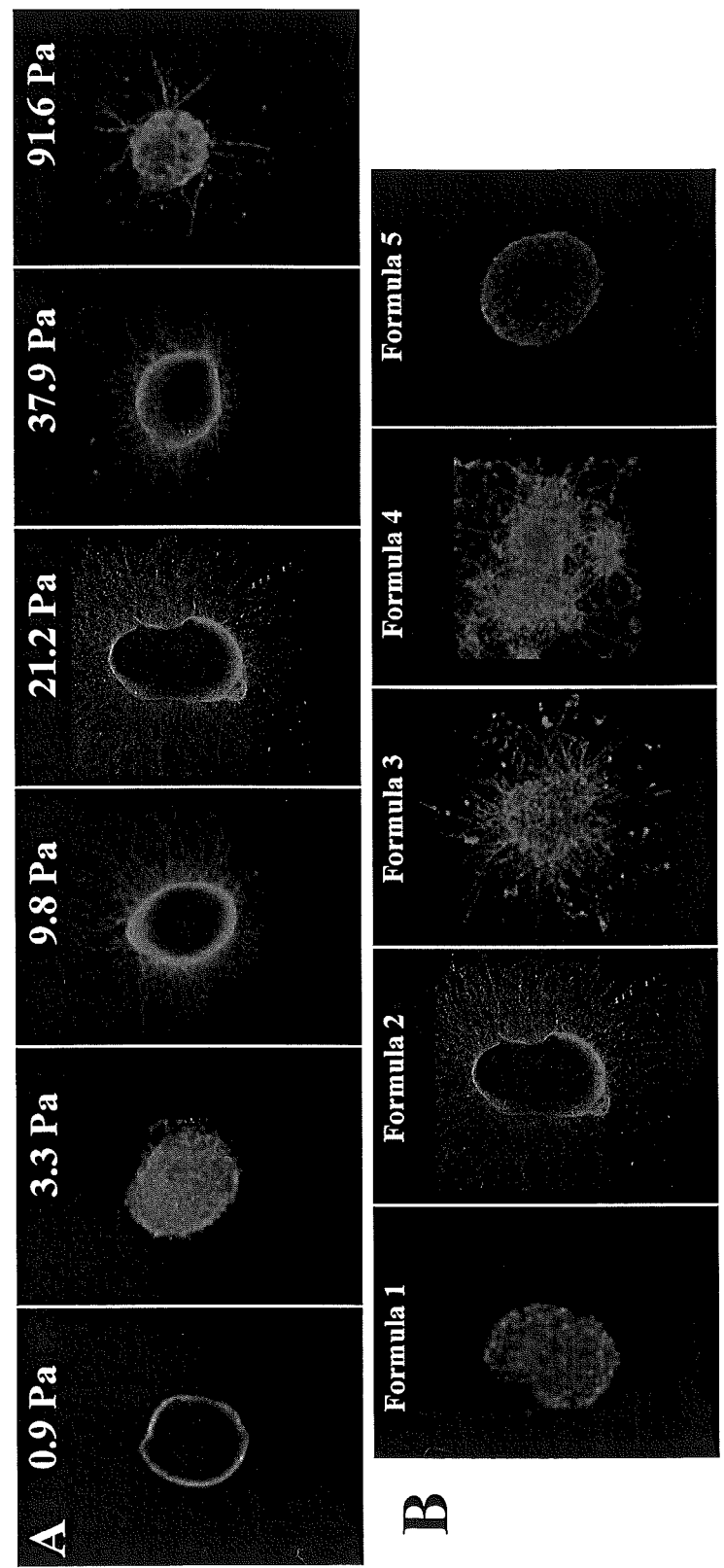
FIGS. 1A-1B show human embryonic stem cell derived neurospheres cultured inside hydrogels comprising different ratios of thiolated multi-arm PEG and laminin-derived short peptide sequences (CDPVCC GTARPGYIGSRGTARC-CAC, SEQ ID NO:1). Formula 1 is 100% PEG, Formula 2 is 75% PEG, Formula 3 is 50% PEG, Formula 4 is 25% PEG, and Formula 5 is 0% PEG.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

DEFINITIONS

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

An "effective" amount as used herein is an amount of a composition of this invention that provides some improvement or benefit to the subject. Alternatively stated, an "effective" amount is an amount that provides some revascularization, reenervation, repopulation, recruitment, treatment, etc. Those skilled in the art will appreciate that such effects need not be complete or curative, as long as some benefit is provided to the subject.

By the terms "treat," "treating" or "treatment of," it is intended that the severity of the patient's condition is reduced or at least partially improved or modified and that some alleviation, mitigation or decrease in at least one clinical symptom is achieved.

As used herein, the term "in-situ crosslinkable hydrogel" describes a hydrogel of this invention in which the gelation process can occur at a local tissue site. The material components of the hydrogel can be injected into a local tissue site in the form of liquid precursors, and gelation starts at the local tissue site right after and/or simultaneously with the injection. The gelation normally occurs in the presence of crosslinkers, and it is accelerated at elevated temperatures (such as at body temperatures when compared to room temperature). To control the gelation in situ, the crosslinker is mixed into the liquid precursors right before the injection so that gelation starts right after the injection. The concentration of the crosslinker in the material also determines the length of time necessary for the gelation to be completed at the tissue site.

As used herein, the term "preventing scar tissue growth in a CNS lesion" refers to any activity that effectively inhibits the growth of scar tissue in a CNS lesion, e.g., an inhibition of about 10%, 20%, 30%, 40%, 50%, 60%, 70%, 80%, 90%, 95%, or more. Those skilled in the art will appreciate that such inhibition need not be complete, as long as scar tissue growth is inhibited, e.g., in an amount that can be detected and or measured.

As used herein, the term "an agent that blocks the biosynthesis of inhibitory ECM components" refers to any molecule or compound that inhibits the biosynthesis of one or more of the molecules that comprise the ECM of scar tissue normally found in or around CNS lesion sites, e.g., an inhibition of about 10%, 20%, 30%, 40%, 50%, 60%, 70%, 80%, 90%, 95%, or more. ECM components are known to those of skill in the art, and include (but are not limited to) collagen IV and chondroitin sulphate proteoglycans. Exemplary agents include p-nitrophenyl-b-D-xylopyranoside (PNPX) and prolyl hydroxylase inhibitors (PHIS), such as ethyl-3,4 dihydroxybernoate (EDHB) and dimethyloxalylglycine (DMOG).

As used herein, the term "an agent that reduces recruitment of an inflammatory response" or "reduces activity of inflammatory cells" refers to a molecule or compound that blocks or interferes with the migration or movement of cells that are involved in an inflammatory response (e.g., macrophages, neutrophils, astrocyes, etc.) to the lesion site and/or inhibits or interferes with the activity of inflammatory cells such that inflammation at the lesion site is reduced or inhibited. A reduction in recruitment and/or a reduction in activity as described herein can be about 10%, 20%, 30%, 40%, 50%, 60%, 70%, 80%<90% OR 100% as compared to the amount of recruitment or activity that would be present in the absence of said molecule or compound. Nonlimiting examples of such molecules or compounds include methylprednisone, dexamethasone, erythropoietin, minocyclin, progesterone, estrogen, anti CD-11 antibodies, magnesium sulfate, riluzole, polyethylene glycol, atorvastatin, ionosin, pioglitazone, chondrotinase ABC, anti Nogo antibodies and any combination thereof.

As used herein, the term "ECM-degrading enzyme" refers to any enzyme that promotes the breakdown and/or digestion of one or more molecules that comprise the ECM of scar tissue normally found in or around CNS lesion sites. Exemplary ECM-degrading enzymes include collagenase IV and chondroitinase ABC ($Ch^{ase}ABC$).

As used herein, the term "scar-reduced environment" refers to any environment that is substantially lacking glial scar tissue. An environment is substantially lacking glial scar tissue when less than about 20%, e.g., less than about 15%, 10%, 5%, or 1% of the total volume of the environment is occupied by glial scar tissue. Methods of measuring the total volume of a CNS lesion are known to those of skill in the art.

As used herein, the term "neural stem cell recruiting factor" refers to any molecule that promotes the attraction and/or proliferation of neural stem cells. In one embodiment, neural stem cell recruiting factors are naturally occurring proteins or active fragments or analogs thereof. Such factors include, but are not limited to, hepatocyte growth factor (HGF), insulin-like growth factor 1 (IGF-1), fibroblast growth factor 2 (FGF-2), platelet-derived growth factor (PDGF), gliotropic factors (Human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18 and glioma-produced ECM (tenascin-C). In other embodiments, the factor may be a small molecule, e.g., less than about 1000 Da, less than about 2000 Da, less than about 3000 Da, less than about 4000 Da less than about 5000 Da, less than about 6000 Da, less than about 7000 Da, less than about 8000 Da, less than about 9000 Da or less than about 10,000 Da.

As used herein, the term "neural differentiation factor" refers to any molecule that promotes the differentiation of neural stern cells and their precursors into neurons and/or glia. Such factors include, but are not limited to, nerve growth factor (NGF), brain-derived neurotrophic factor (BDNF), neurotrophin-3 (NT-3), neurotrophin-4 (NT-4), novel neurotrophin-1 (NNT-1), glial-cell-line-derived neurotrophic factor (GDNF), and conserved dopamine neurotrophic factor (CNTF).

As used herein, the term "neural stem cell mobilizing factor" refers to any molecule that promotes the motility of neural stem cells. Such factors include, but are not limited to, leukemia inhibitory factor (LIF) and granulocyte-colony stimulating factor (G-CSF).

I. Revascularization

Previous reports have implicated the crucial role of vasculature in inducing, supporting, and sustaining neurogenesis, neuronal survival, and brain architecture, which are fundamental for brain tissue regeneration (Ohab et al., *J. Neurosci.* 26:13007 (2006); Leventhal et al., *Mol. Cell. Neurosci.* 13:450 (1999)). Thus, reconstructing the damaged vasculature network within a CNS lesion is a fundamental step in alleviating tissue injury and promoting brain tissue regeneration.

In designing therapeutic strategies to reconstruct the damaged vasculature network of a CNS lesion, one must seek to minimize the surgical trauma to the brain tissue during the implantation procedure to protect healthy brain tissue and the integrity of the blood-brain barrier. For this purpose, biopolymer liquid precursors that are able to undergo in situ polymerization to form scaffolds that conform to the irregular dimensions of the lesion site without producing toxic residues are highly desirable.

To that end, the present invention comprises, consists essentially of, or consists of an in-situ crosslinkable hydrogel that acts as a substrate to promote angiogenesis and neural regeneration. In general, embodiments of the present invention comprise a hydrogel with mechanical properties similar to those of native CNS tissue (~10-40 Pa) and cell adhesion motifs. Most importantly, the hydrogel of the present invention is able to undergo in situ gelation in CNS tissue, allowing it to conform to the irregular dimensions of the CNS lesion.

In some embodiments of the present invention, the in-situ crosslinkable hydrogel comprises at least one synthetic or ECM molecule; in other embodiments, the hydrogel comprises at least two different synthetic or ECM molecules. The synthetic molecule(s) or ECM molecule(s) may be chemically modified, such as by the addition of thiol groups or acrylate groups.

In some embodiments, the hydrogel of this invention can comprise, consist essentially of or consist of a hydrophilic component and an adhesive component. The hydrophilic component can comprise, consist essentially of or consist of, e.g., a polyalkylene glycol (PAG) (e.g., polyethylene glycol (PEG)), hyaluronic acid, chitosan and any combination thereof. The adhesive component of the hydrogel can comprise, consist essentially of or consist of gelatin, collagen, laminin, fibronectin, vitronectin and any combination thereof. Any of the components of the hydrogel of this invention can be thiolated (e.g., thiolated hyaluronic acid, thiolated gelatin, thiolated collagen, thiolated fibronectin, thiolated vitronectin, thiolated laminin, thiolated chitosan, thiolated PEG, thiolated heparin, etc.) or any of the components of the hydrogel can be non-thiolated, in any combination of thiolated and nonthiolated components. The molar ratio of hydrophilic component to adhesive component in the hydrogel can be from about 500:1 to about 1:500, including any ratio between these values not explicitly recited here (e.g., 300:1, 100:1, 50:1, 1:250, 1:100, etc.). The weight ratio of the hydrophilic component to adhesive component in the hydrogel can be from about 1500:1 to about 1:1500, including any ratio between these values not explicitly recited here (e.g., 1300:1, 1000:1, 1:1000, etc.) In some embodiments in which hyaluronic acid or thiolated hyaluronic acid is included in the hydrogel, it can be present in a range of about 2% to about 25% (e.g., about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%) of the weight of the hydrogel.

The hydrogel of the present invention may comprise any extracellular matrix molecule, including one or more of hyaluronic acid, collagen, heparin, laminin, gelatin, fibronectin, dextran, and/or chitosan. In certain embodiments, the hydrogel comprises both hyaluronic acid and collagen. In a still more preferred embodiment, the ratio of hyaluronic acid to collagen, laminin, chitosan or gelatin can range from about 15:1 to about 1:15 (including e.g., a range of about10:1 to about 1:10; a range of about 5:1 to about 1:5, a range of about 3:1 to 1:3). In one embodiment, the ratio of hyaluronic acid to collagen is about 1:3. In further embodiments, the hydrogel may comprise hyaluronic acid, collagen, and laminin. In yet further embodiments the hydrogel may comprise hyaluronic acid and gelatin in any of the ratios described herein. In some embodiments, the hydrogel can comprise chitosan and gelatin in any ratios described herein.

The hydrogel of the present invention may also comprise any types of polyethylene glycol (PEG), including one arm PEG or multi-arm PEG. PEG may have thiol groups or acrylate groups. The hydrogel of the present invention may comprise any types of ECM derived short peptide sequences, including short peptides from collagen, laminin, gelatin, fibronectin, vitronectin, and so on. In certain embodiments, the hydrogel comprises both PEG and peptide sequence(s). In a still further embodiment, the ratio of PEG to peptide sequence ranges from about 10:1 to about 1:10 (including e.g., about 5:1 to about 1:5 or about 3:1 to about 1:3). In one embodiment, the ratio of PEG to peptide sequence is about 1:3.

In some embodiments, the hydrogel of the present invention promotes angiogenesis in a CNS lesion without using angiogenic growth factors. Thus, in one embodiment, the hydrogel does not comprise any angiogenic growth factors. In other embodiments, the hydrogel does comprise angiogenic growth factors. Angiogenic growth factors include, without limitation, VEGF and PDGF.

A lesion of this invention can be but is not limited to, a lesion in the brain, a lesion in the spinal cord, a lesion due to ischemia, a lesion due to hemorrhage, a lesion due to stroke, a lesion due to traumatic brain injury, a lesion due to anoxic brain injury, a lesion due to acute spinal cord injury, a lesion due to chronic spinal cord injury and a lesion due to multiple sclerosis, as well as any combinations thereof.

In some embodiments, the hydrogel of this invention can comprise, consist essentially of or consist of at least one synthetic molecule or ECM molecule. In other embodiments, the hydrogel can comprise, consist essentially or of consist of at least two (e.g., 2, 3, 4, 5, 6, 7, 8, 9, 10, etc.) different synthetic molecules or ECM molecules. Such synthetic or ECM molecules can be chemically modified, and/or can be thiolated and/or acrylated. In some embodiments, the hydrogel of this invention can comprise hyaluronic acid, collagen, heparin, laminin, gelatin, polyethylene glycol (in some embodiments with up to 10 arms), and/or thiolated peptide sequences as well as any combination thereof. In certain embodiments, the hydrogel of this invention comprises hyaluronic acid and collagen. In some embodiments, the ratio of hyaluronic acid to collagen can range from about 10:1 to about 1:10 (e.g., 9:1, 8:1, 7:1, 6:1, 5:1, 4:1, 3:1, 2:1, 1:1, 1:2, 1:3, 1:4, 1:5, 1:6, 1:7, 1:8, 1:9, 1:10). In particular embodiments, the ratio of hyaluronic acid to collagen ranges from about 5:1 to about 1:5 and in more particular embodiments, the ratio of hyaluronic acid to collagen is about 1:3. In other embodiments, the hydrogel can comprise hyaluronic acid, collagen and laminin. In other embodiments, the hydrogel can comprise hyaluronic acid and gelatin in any of the ratios described herein.

In particular embodiments, the hydrogel of this invention can comprise, consist essentially of, or consist of chitosan and gelatin. The chitosan:gelatin ratio in the hydrogel can be from about 0.5:15 to about 15:0.5 (e.g., about 0.5:15, 1:15, 2:15, 3:15, 4:15; 5:15, 6:15, 7:15, 8:15, 9:15; 10:15, 11:15, 12:15, 13:15, 14:15, 15:14, 15:13, 15:12, 15:11, 15:10, 15:9, 15:8, 15:7, 15:6, 15:5, 15:4, 15:3, 15:2, 15:1, 15:0.5, etc.). In some embodiments, the chitosan:gelatin ratio can be about 6:4.

In some embodiments, the hydrogel of this invention does not comprise any angiogenic factors. In some embodiments, the hydrogel can comprise at least one neural stem cell recruiting factor, which can be, e.g., hepatocyte growth factor. In some embodiments, the hydrogel can comprise at least one mitogen (e.g., proliferating factor). In further embodiments, the hydrogel of this invention can comprise at least one neural differentiation factor, which can include but is not limited to BDNF, NT-3, GDNF and CNTF, singly or in any combination.

Some embodiments of the methods of this invention include the step comprising delivering at least one neural stem cell mobilizing factor to the CNS of a subject on whom the methods are being carried out. In particular embodiments, the neural stem cell mobilizing factor can be leukemia inhibitory factor and in some embodiments, the neural stem cell mobilizing factor can be delivered to the subventricular zone. The present invention also encompasses in the methods herein the further step comprising delivering a neural stem cell recruiting factor to a lesion site and delivering a neural stem cell mobilizing factor to the subventricular zone. In the methods described herein, the neural stem cell recruiting factor can be hepatocyte growth factor and the neural stem cell mobilizing factor can be leukemia inhibitory factor.

In the methods of this invention, the factor, agent or enzyme can be present in the hydrogel and/or can be loaded into nanoparticles, microparticles, liposomes, membranes, scaffolds and/or micelles, in any combination. Such nanoparticles, microparticles liposomes, membranes, scaffolds and/or micelles can be biodegradable. In particular embodiments, a nanoparticle of this invention can comprise PLGA or the nanoparticle can be any degradable polymer.

In some embodiments, the hydrogel, nanoparticle, microparticle, liposome, membrane, scaffold and/or micelle of this invention can comprise cells and/or constructs and/or implants, nonlimiting examples of which include neural stem cells, embryonic stem cells, olfactory ensheathing cells, neural progenitor cells, neural stem cell derived precursor cells, fibroblasts, bone marrow derived stem cells, dorsal root ganglion, axonal constructs, peripheral nerve implants, Schwann cells and any combination thereof. These cells, constructs and/or implants are added to, positioned in or on and/or incorporated into the vehicle of this invention prior to delivery, contact or administration of the vehicle to a subject. In other embodiments, the hydrogel, nanoparticle, microparticle, liposome, membrane, scaffold and/or micelle of this invention can be devoid of cells or devoid of particular types of cells (e.g., as exemplified herein) prior to delivery, contact or administration of the hydrogel, nanoparticle, microparticle, liposome, membrane, scaffold and/or micelle to the subject.

In some embodiments, the hydrogel of this invention is designed for sustained release of the factor, agent and/or enzyme. The hydrogel can be designed for sustained release of an effective amount of the factor, agent and/or enzyme for at least 5 days, at least 30 days or at least 60 days.

In the methods described herein for preventing scar tissue growth at a CNS lesion, or maintaining a scar reduced environment in a CNS lesion, the agent that blocks the biosynthesis of inhibitory ECM components can be but is not limited to p-nitrophenyl-b-D-xylopyranoside, dimethyloxalylglycine, cyclic nucleotides, and combinations thereof.

In the methods described herein for digesting scar tissue growth in a CNS lesion or maintaining a scar reduced environment in a CNS lesion, the ECM degrading enzyme can be but is not limited to chondroitinase ABC, collagenase IV, and combinations thereof.

In some methods of this invention, a pure synthetic hydrogel, a extracellular matrix (ECM) based hydrogel, a chemically modified ECM based hydrogel, or a mixture of synthetic and ECM based hydrogels can be used.

In some embodiments of the foregoing, the ECM-based hydrogel comprises at least one ECM molecule. In other embodiments, the hydrogel comprises at least two different ECM molecules. Said ECM molecule(s) may be chemically modified, such as by the addition of a thiol group. In some embodiments, the hydrogel may comprise hyaluronic acid, collagen, heparin, laminin, gelatin, fibronectin, and/or chitosan. In certain embodiments, the hydrogel comprises both hyaluronic acid and collagen. In other embodiments, the ratio of hyaluronic acid to collagen ranges from about 10:1 to about 1:10, e.g., about 1:3. Further embodiments may comprise hyaluronic acid, collagen, and laminin. In certain embodiments, the hydrogel comprises both hyaluronic acid and gelatin. In other embodiments, the ratio of hyaluronic acid to gelatin ranges from about 10:1 to about 1:10, e.g., about 1:3. Further embodiments may comprise hyaluronic acid, gelatin, and laminin. Poly(ethylene glycol) tetra-acrylate (PEGTA) or PEGDA can be used as crosslinker for gelation. The concentration of PEGTA or PEGDA can be from about 0.01% to about 20%.

In some embodiments of the foregoing, the hydrogel comprises at least one synthetic molecule. In other embodiments, the hydrogel comprises at least two (e.g., 3, 4, 5, 6, 7, 8, 9, 10, etc.) different synthetic molecules. The synthetic molecule(s) may be chemically modified, such as by the addition of one or more thiol groups or acrylate groups. In some embodiments, the hydrogel may comprise polyethylene glycol (PEG), also known as polyethylene oxide (PEO). In some embodiments, the hydrogel of this invention can comprise, consist essentially of or consist of synthetic peptide sequences (e.g., laminin peptide sequences, fibronectin peptide sequences, vitronectin peptide sequences, collagen peptide sequences, etc.), which can be thiolated (e.g., thiolated laminin peptide sequence, thiolated fibronectin peptide sequence, vitronectin peptide sequence, thiolated collagen peptide sequence). In certain embodiments, the hydrogel comprises, consists essentially of or consists of thiolated PEG and thiolated laminin peptide sequence(s). In other embodiments, the ratio of thiolated PEG to thiolated peptide sequence can range from about 1500:1 to about 1:1500, e.g., about 1:3. 1:100, 1:500; 1:1300, 1300:1, 500:1, 100:1, 3:1, etc. Further embodiments may comprise thiolated PEG and/or one or more (e.g., 2, 3, 4, 5, 6, 7, 8, 9, 10, etc.) of a thiolated peptide sequence from fibronectin, vitronectin, laminin, collagen etc. PEG can be single arm to multi-arm (e.g., 1, 2, 3, 4, 5, 6, 7, 8, 9, or 10 arms). Poly(ethylene glycol) tetra-acrylate (PEGTA) or PEGDA can be used as crosslinker for gelation. The concentration of PEGTA or PEGDA in the hydrogel can be from about 0.01% to about 20% (e.g., 1.0%, 0.5%. 1.0%. 2.0%>3.0%. 4.0%>5.0%, 6.0%, 7:0%, 8:0%, 9.0%, 10%, 11%, 12%, 13%, 14%, 15%, 16%, 17%, 18%, 19%, 20%).

Nonlimiting examples of a laminin peptide of this invention include CCRRIKVAVWLC (SEQ ID NO:2), CCRRYVVLPRWLC (SEQ ID NO:3), CCRRNIAEIIKDIWLC (SEQ ID NO:4), CCRRYIGSRWLC (SEQ ID NO:5), CDPVCCGTARPGYIGSRGTARCCAC (SEQ ID NO:6), CDPVCCGTARPGNIAEIIKDIGTARCCAC (SEQ ID NO:7), CDPVCCGTARPGYVVLPRGTARCCAC (SEQ ID NO:8), CDPVCCGTARPGIKVAVGTARCCAC (SEQ ID NO:9) and any combination thereof. Nonlimiting examples of a fibronectin peptide of this invention include CCRRGRGDSPKWLC (SEQ ID NO:10), CCRRAVTGRGDSPASSWLC (SEQ ID NO:11), CDPVCCGTARPGPQVTRGDVFTMPGTARCCAC (SEQ ID NO:12), CDPVCCGTARPGRGDGTARCCAC (SEQ ID NO:13) and any combination thereof. A nonlimiting example of a vitronectin peptide of this invention includes CCRRPQVTRGDVFTMPWLC (SEQ ID NO:14). Any or all of these peptides can be thiolated peptides.

In some embodiments of this invention, the hydrogel comprises at least one synthetic molecule and one ECM. In other embodiments, the hydrogel comprises two or more (e.g., 2, 3, 4, 5, 6, 7, 8, 9, 10, etc.) different synthetic molecules and two or more (e.g., 2, 3, 4, 5, 6, 7, 8, 9, 10, etc.) ECMs. The synthetic molecule(s) or ECM(s) may be chemically modified, such as by the addition of one or more thiol groups or acrylate groups. In some embodiments, the hydrogel may comprise polyethylene glycol, synthetic peptide sequences, hyaluronic acid, and gelatin. In certain embodiments, the hydrogel comprises both thiolated PEG, thiolated laminin short peptide sequences, thiolated hyaluronic acid, and thiolated gelatin. In other embodiments, the ratio of thiolated PEG:thiolated peptide sequence:thiolated hyaluronic acid: thiolated gelatin ranges from about 10:1:1:1 to about 1:1:1: 10, e.g., about 4:3:2:1. Further embodiments may comprise thiolated PEG, thiolated peptide sequence from fibronectin, etc. PEG can be single arm to multi-arm (e.g., 1-10 arms). Poly(ethylene glycol) tetra-acrylate (PEGTA) or PEGDA can be used as crosslinker for gelation. The concentration of PEGTA or PEGDA can be from about 0.01% to about 20%.

In some embodiments of the present invention, the factor, agent, and/or enzyme present in the hydrogel is loaded into nanoparticles (e.g., biodegradable nanoparticles), lipsomes, micelles or any combination thereof.

In some embodiments of the present invention, the hydrogel is designed for sustained release of the factor, agent, and/or enzyme present therein. In certain embodiments, the hydrogel releases an effective amount of the factor, agent, and/or enzyme for at least about 5 days, e.g., at least about 10 days, at least about 15 days, at least about 20 days, at least about 25 days, at least about 30 days or at least about 60 days.

One of skill in the art will appreciate that the factors, agents, and enzymes discussed above with relation to certain embodiments of the present invention may likewise be included in alternate embodiments of the claimed invention. Indeed, particular embodiments of the claimed invention may incorporate factors, agents, and enzymes from each of the aforementioned categories: neural stem cell recruiting factors, neural stem cell proliferation factors, neural stem cell differentiation factors, neural stem cell mobilization factors, agents that block the biosynthesis of inhibitory ECM components, and ECM-degrading enzymes.

II. Reenervation

For the ultimate repair following cerebral stroke, neuronal and glial repopulation of the cranial lesion cavity is important. An example of a cell source for neural replacement includes endogenous neural stem cells (NSCs). These cells normally reside in the forebrain subventricular zone (SVZ)-olfactory bulb pathway in adult mammalian brain, and are able to generate neurons and glia throughout life (Gage, *Science* 287:1433 (2000)). Accumulating evidence indicates the ability of SVZ-endogenous NSCs/precursors to proliferate and migrate to areas of ischemic injury in adult brain (Jin et al., *Mol. Cell. Neurosci.* 24:171 (2003); Parent, *Neuroscientist* 9:261 (2003)). Further, NSCs are able to form appropriate neural cell types to replace damaged neurons and glia cells (Arvidsson et al., *Nature Med.* 8:963 (2002); Parent et al., *Ann. Neurol.* 52:802 (2002), suggesting that the manipulation of endogenous NSCs may be a potential strategy for brain stroke repair.

Thus, embodiments of the present invention comprise, consist essentially of, or consist of a method of delivering an in-situ crosslinkable hydrogel that contains a neural stern cell recruiting factor, mitogen/proliferation factor, and/or neural differentiation factor to the lesion in an amount effective to promote both revascularization of the lesion and recruitment of neural stem cells to the lesion. In certain embodiments, the hydrogel contains at least one neural stem cell recruiting factor and/or at least one neural differentiation factor. Neural stem cell recruiting factors suitable for use in the present invention include, but are not limited to, HGF, LIF, IGF-1, SDF-1, FGF-2, and PDGF. Neural differentiation factors suitable for use in the present invention include, but are not limited to, BDNF, NT-3, GDNF, and CNTF.

Further embodiments of the claimed invention comprise supplementing the delivery of a revascularization-promoting amount of an in-situ crosslinkable hydrogel with the delivery of a neural stem cell mobilizing factor to the CNS. In certain embodiments, the neural stem cell mobilizing factor is delivered to the subventricular zone. In other embodiments, the neural stem cell mobilizing factor can be, e.g., LIF and/or G-CSF.

Additional embodiments of the claimed invention comprise a method of delivering an in-situ crosslinkable hydrogel to a lesion in an amount effective to promote revascularization of the lesion, and delivering both a neural stein cell recruiting factor and a neural stem cell mobilizing factor to the CNS. In certain embodiments, at least one neural stem cell recruiting factor is present in the hydrogel and at least one neural stem cell mobilizing factor is delivered to the subventricular zone. In other embodiments, the neural stem cell recruiting factor is HGF and the neural stein cell mobilizing factor is LIF.

III. Scar Tissue

A detailed characterization of the cellular and biomolecular sequelae arising from ischemic stroke has led to the recognition of the predominant role of the dense ECM-rich scar tissue that forms at the lesion site in inhibiting brain tissue regeneration. Following acute focal ischemic stroke, cells undergo two major modes of deaths: necrosis, and apoptosis (Lipton, *Physiol. Rev.* 79:1431 (1999)). While necrosis is more common in the core tissue, penumbral cells that are located centrifugally from the core may undergo either mode of death. Accompanying the cell deaths, the infarcted region starts to lose structural integrity in a radial fashion from the core to the penumbra. Injured neurons and activated inflammatory cells, such as microglia, macrophages, and reactive astrocytes, may release toxic mediators at the lesion site, which amplify tissue damage (Trendelenburg et al., *Glia* 50:307 (2005)). Scattered dead neurons in the ischemic core are initially seen after 10 to 20 minutes, followed by the actual infarct formation at about 1 hour. Eventually (beyond 1-2 weeks), persistent cell dysfunction and poor neural regenerative capabilities at the ischemic core and beyond lead to the formation of a cystic cavity encapsulated in a dense layer of glial scar tissue (Lipton, *Physiol. Rev.* 79:1431 (1999)).

Scar tissue, which consists primarily of reactive astrocytes and proteoglycans (Lindsay, Reactive gliosis. In: Fedoroff S, Vernadakis A, editors. Astrocytes.

Orlando: Academic Press; 1986. p 231-262), acts as a major physical barrier for brain tissue regeneration across the lesion and the structural and functional integration of the regenerating tissue with existing neural circuitry (Lipton, *Physiol. Rev.* 79:1431 (1999); Gartshore et al., *Exp. Neurol.* 147:353 (1997)). In addition, scar tissue may serve as a diffusion barrier, obstructing the delivery of pharmacological agents and the transport of oxygen and nutrients to cells implanted within the lesion cavity.

In the acute and subacute stages of stroke, inflammatory cells travel from the vasculature into the ischemic region, and interact to form a dense structure known as a glial scar. The response of astrocytes to injury is characterized by hypertrophy and hyperplasia (Barrett et al., *Exp. Neurol.* 84:374 (1984)), accompanied by an increased production of intermediate filaments (such as GFAP (Bignami et al., *J. Comp. Neurol.* 153:27 (1974); Eng, *J. Neuroimmunol.* 8:203 (1985)) and vimentin (Yang et al., *Mol. Chem. Neuropathol.* 21:155 (1994))). In addition, astrocytes—along with other CNS-resident cells, such as microglia and oligodendrocytes, and hematogenous cells, like macrophages—play a role in the regulation of ECM production after CNS injury (Fitch et al., *J. Neurosci.* 19:8182 (1999); Preston et al., *J. Neurotrauma* 18:83 (2001)). The resulting ECM contains several classes of molecules that are inhibitory to brain tissue regeneration, including proteoglycans (Gallo et al., *Exp. Cell Res.* 187:211 (1990); Gallo et al., *Dev. Biol.* 123:282 (1987)), collagen type IV (Hermanns et al., *Restor. Neurol. Neurosci.* 19:139 (2001); Hermanns et al. *J. Neurosci. Meth.* 110:141 (2001); Stichel et al. *Eur. J. Neurosci.* 11:632 (1999)), and the basal membrane (Lips et al. *J. Neurocytol.* 24:449 (1995); Stichel et al. *J. Neurocytol.* 23:615 (1994); Stichel et al. *Eur. J. Neurosci.* 7:401 (1995); Timpl et al. *Int. Rev. Exp. Pathol.* 29:1 (1986)).

Proteoglycans represent a special class of heavily glycosylated glycoproteins characterized by a protein core that is covalently linked by four sugar moieties to a sulphated glycosaminoglycan (GAG) chain. Among the four types of proteoglycans (Johnson-Green et al. *Glia* 4:314 (1991)), the chondroitin sulphate proteoglycans (CSPGs) are a relatively large family. Up-regulation of CSPG production has been documented in glial scars in both the brain and spinal cord of adult mammalians (Jones et al. *Exp. Neurol.* 182:399 (2003); McKeon et al. *J. Neurosci.* 19:10778 (1999); Tang et al. *J. Neurosci. Res.* 71:427 (2003)). The inhibitory effects of CSPGs on axonal outgrowth and CNS tissue regeneration have been demonstrated both in vitro (Hynds et al. *Exp. Neurol.* 160:244 (1999); Snow et al. *Exp. Neurol.* 109:111 (1990)) and in vivo (Jones et al. *J. Neurosci.* 22:2792 (2002); Moon et al. *Neuroscience* 109:101 (2002)), suggesting that elimination of these ECM molecules may be essential to promote CNS tissue repair and regeneration.

In addition to the inhibitory effects of CSPGs, several other molecules are known to be up-regulated in the glial scar and to contribute to regeneration failure. Collagen IV, a matrix molecule that is primarily secreted by meningeal fibroblasts, is a major component of the basal membrane, and has been implicated in the inhibition of regeneration after CNS injury (Klapka et al. *J. Neurotrauma* 23:422 (2006)). In a brain lesion model of post-commissural fornix transaction, collagenous basal membrane was shown to be a major impediment for axon regeneration (Hermanns et al. *Restor. Neurol. Neurosci.* 19:139 (2001)). Blocking collagen IV deposition promoted axonal regeneration across the lesion site following mechanical injury to adult rat brain (Stichel et al. *Eur. J. Neurosci.* 11:632 (1999)).

Since any form of treatment designed to regenerate brain tissue after stroke, TBI, or SCI will have to occur at the lesion site, sustaining a scar-reduced, permissive environment is key to successful brain tissue regeneration. To that end, the present invention provides methods of preventing scar tissue growth in a CNS lesion, digesting existing scar tissue in a CNS lesion, and maintaining a scar-reduced environment in a CNS lesion.

Selective enzymatic removal of ECM molecules from glial scar tissue results in the degradation of pre-existing scars within the CNS lesion (Zuo et al., *J. Neurosci.* 18:5203 (1998); Zuo et al., *Exp. Neurol.* 154:654 (1998)), thereby enhancing CNS repair. For example, chondroitinase ABC ($Ch^{ase}$ABC) may be used to digest the GAG moieties of CSPGs, resulting in the dissolution of pre-existing scar tissue and enhanced axonal regeneration (Snow et al., *Exp. Neurol.* 109:111 (1990); Bradbury et al., *Nature* 416:636 (2002); Moon et al., *Nature Neurosci.* 4:465 (2001); Li et al., *J. Neurosci. Res.* 85:536 (2007)). Likewise, the degradation of collagen IV quells the lesion-induced deposition of basal membrane and partially facilitates CNS tissue regeneration (Stichel et al., *Eur. J. Neurosei.* 11:632 (1999); Guth et al., *J. Neurosurg.* 52:73 (1980)).

Thus, some embodiments of the present invention comprise a method of delivering to a lesion an amount of an in-situ crosslinkable hydrogel comprising at least one ECM-degrading enzyme, wherein said amount is effective to digest scar tissue. Appropriate enzymes may include, without limitation and in any combination, CSPG-digesting enzymes, such as $Ch^{ase}ABC$, and collagen-eliminating enzymes, such as collagenase IV. In certain embodiments, the ECM-based hydrogel comprises both $Ch^{ase}ABC$ and collagenase IV.

In addition to digesting pre-existing glial scar tissue, it is desirable to prevent the formation of new scar tissue in the lesion site. The formation of new scar tissue can be prevented by blocking the biosynthesis of repair-inhibiting ECM molecules. Several compounds have been found to be useful in the present invention to inhibit scar formation, including CSPG suppressors such as p-nitrophenyl-b-D-xylopyranoside (PNPX) (Zhang et al., World Congress on Tissue Engineering and Regenerative Medicine (2006) Pittsburgh, Pa., presented Apr. 27, 2006), and prolyl hydroxylase inhibitors (PHIs), such as ethyl-3,4 dihydroxybenoate (EDHB) and dimethyloxalylglycine (DMOG) (Zhang et al., Abstracts of Papers of the American Chemical Society 229:U911 (2005) San Diego, Calif., presented Mar. 13, 2005), which notably inhibit collagen IV synthesis. In addition, it is known that cyclic nucleotides are able to convert myelin-associated glycoproteins from an axon-repulsive state to one in which they attract axonal outgrowth.

Thus, embodiments of the present invention comprise a method of delivering to a lesion an amount of an in-situ crosslinkable hydrogel comprising at least one agent that blocks the biosynthesis of inhibitory ECM components, wherein said amount is effective to prevent scarring. Appropriate agents include those that block the biosynthesis of CSPG, such as PNPX, agents that block the biosynthesis of collagen IV, such as EDHB and DMOG, and cyclic nucleotides as well as any combination thereof. In certain embodiments, the in-situ crosslinkable hydrogel comprises at least one agent that blocks the biosynthesis of CSPG and at least one agent that blocks the biosynthesis of collagen IV.

Further embodiments of the present invention are aimed at maintaining a scar-reduced lesion site. These embodiments comprise a method of delivering to a lesion an amount of an in-situ crosslinkable hydrogel comprising at least one agent that blocks the biosynthesis of inhibitory ECM components and, optionally, at least one ECM-degrading enzyme, wherein said amount is effective to maintain a scar-reduced environment. Certain embodiments comprise an in-situ crosslinkable hydrogel that contains agents that block the biosynthesis of CSPG and collagen IV, as well as the enzymes $Ch^{ase}ABC$ and collagenase IV, in any combination.

Given the ubiquitous nature of CSPGs and collagen IV within the CNS, one skilled in the art will appreciate the need to carefully control the release of enzymes and/or agents that interfere with the normal life cycle of these ECM components. The present invention provides for such control via the slow, sustained release of ECM-degrading enzymes and biosynthesis-blocking agents within the lesion, with the release rate controlled by the composition (e.g., density, charge, shape) of the hydrogel.

IV. Topical Treatment of Spinal Cord Injury

Particular embodiments of this invention are based on the unexpected discovery that topical administration of a vehicle of this invention (e.g., a hydrogel, nanoparticle, microparticle, micelle, a membrane, a scaffold, or any combination thereof) to a spinal cord injury site can have a therapeutic effect. The vehicle can deliver factors and/or agents topically to the spinal cord injury site to impart a therapeutic effect. Such topical administration provides improved results as compared with administration of such vehicles and/or factor and agents via injection.

Thus, in one embodiment of this invention, a method is provided of treating a spinal cord injury, comprising topically delivering to the spinal cord injury site an amount of a neurotrophic factor and or an anti-inflammatory agent effective to treat the spinal cord injury.

Also provided herein is a method of reducing inhibition of axonal regeneration at a spinal cord injury site, comprising topically delivering to the site an amount of a neurotrophic factor and/or an anti-inflammatory agent effective in reducing inhibition of axonal regeneration at the spinal cord injury site.

In further aspects, the present invention provides a method of decreasing secondary injury at a spinal cord injury site, comprising topically delivering to the site an amount of a neurotrophic factor and/or an anti-inflammatory agent effective in decreasing secondary injury at the spinal cord injury site.

In the methods described herein, the spinal cord injury can be an acute spinal cord injury in some embodiments and the spinal cord injury can be a chronic spinal cord injury in some embodiments. For example, an acute spinal cord injury would be treated according to the methods described herein to decrease secondary injury at the spinal cord injury site.

In the methods described herein, the neurotrophic factor and/or anti-inflammatory agent can be in a vehicle that can be, but is not limited to, a hydrogel, a nanoparticle, a nanosphere, a microparticle, a microsphere, a liposome, a micelle, a membrane, a scaffold, or any combination thereof.

In some embodiments of this invention, the vehicle is a hydrogel, which in particular embodiments is a chitosan-gelatin based hydrogel. Thus, the neurotrophic factor and/or anti-inflammatory agent can be present in a chitosan-gelatin based hydrogel. Nonlimiting examples of other hydrogels include a chitosan-laminin based hydrogel.

Nonlimiting examples of a neurotrophic factor or other factor (e.g., growth factor) that can be used in this invention include, in any combination, glial derived neurotrophic factor (GDNF), brain derived neurotrophic factor (BDNF), vascular endothelial growth factor V(EGF), neurotrophin-3 (NT-3), neurotrophin-4 (NT-4), ciliary neurotrophic factor (CNTF), hepatocyte growth factor (HGF), nerve growth factor (NGF), granulocyte colony stimulating factor (G-CSF), fibroblast growth factor (FGF), etc., as are well known in the art (see, e.g., Hempstead. "Dissecting the diverse actions of pro- and mature neurotrophins" *Curr Alzheimer Res* 3(1):19-24 (2006); Reichardt. "Neurotrophin-regulated signalling pathways" *Philos. Trans. R. Soc. Lond, B, Biol. Sci.* 361:1545-64 (2006); Allen and Dawbarn "Clinical relevance of the neurotrophins and their receptors" *Clin. Sci.* 110(2):175-91 (2006).

The present invention further provides a method of delivering a neurotrophic factor, growth factor and/or an anti-inflammatory agent to a spinal cord injury site, comprising topically delivering to the spinal cord injury site a vehicle comprising the neurotrophic factor, growth factor and/or anti-inflammatory agent, wherein the vehicle is selected from the group consisting of a hydrogel, a nanosphere, microsphere, membrane, scaffold or any combination thereof, thereby delivering the neurotrophic factor, growth factor and/or the anti-inflammatory agent to the spinal cord injury site.

Additionally provided herein is a method of preventing or reducing scar tissue growth at a spinal cord injury site, comprising topically delivering to the site an effective amount of at least one agent that reduces recruitment of particular cells (e.g., macrophages, neutrophils, astrocytes fibroblasts, lymphocytes, microglia, eosinophils, mast cells, monocytes, granulocytes, T-cells, B-cells, NK cells) to the injury site and/or reduces the inflammatory response of these cells at the spinal cord injury site, thereby preventing or reducing scar tissue growth at the spinal cord injury site. Nonlimiting examples of such agents of this invention include methylprednisone, dexamethasone, erythropoietin, minocyclin, progesterone, estrogen, anti CD-11 antibodies, magnesium sulfate, riluzole, polyethylene glycol, atorvastatin, ionosin, pioglitazone, chondrotinase ABC, anti Nogo antibodies and any combination thereof.

Furthermore, the present invention provides a method of recruiting stem cells to a spinal cord injury site, comprising topically delivering to the site at least one neural stem cell recruiting factor. Nonlimiting examples of a neural stem cell recruiting factor include stromal cell-derived factor la (SDF-1α) (Imitola et al. "Directed migration of neural stem cells to sites of CNS injury by the stromal cell-derived factor 1α/CXC chemokine receptor 4 pathway" *PNAS* 101(52): 18117-18122 (2004), hepatocyte growth factor (HGF), human recombinant annexin A2, stem cell factor-1, MCP-1, SCYA2, CCL2, MCAF, VEGF, EGF, transmembrane protein 18, tenascin-C, IGF-1, FGF-2, PDGF and any combination thereof.

In the above methods, the agent that reduces recruitment of cells to the injury site and/or reduces the inflammatory response of these cells at the injury site can be in a vehicle that can be a hydrogel, a nanoparticle, a nanosphere, a microparticle, a microsphere, a liposome, a micelle, a membrane, a scaffold and any combination thereof. In some embodiments, the vehicle is a hydrogel, which in particular embodiments is a chitosan-gelatin based hydrogel.

In the above methods, wherein the neural stem cell recruiting factor is in a vehicle that can be a hydrogel, a nanoparticle, a nanosphere, a microparticle, a microsphere, a membrane, a scaffold and any combination thereof. In some embodiments, the vehicle is a hydrogel, which in particular embodiments is a chitosan-gelatin based hydrogel.

In some embodiments, a hydrogel can be topically administered or delivered to a spinal cord injury site to impart a therapeutic effect. Thus, the present invention provides a method of treating a spinal cord injury, comprising topically delivering to the spinal cord injury site an amount of a chitosan/gelatin based hydrogel effective to treat the spinal cord injury.

Also provided herein is a method of reducing inhibition of axonal regeneration at a spinal cord injury site, comprising topically delivering to the site an amount of a chitosan-gelatin based hydrogel effective in reducing inhibition of axonal regeneration at the spinal cord injury site.

In further aspects, the present invention provides a method of decreasing secondary injury at a spinal cord injury site, comprising topically delivering to the site an amount of a chitosan-gelatin based hydrogel effective in decreasing secondary injury at the spinal cord injury site.

In some embodiments, the hydrogel can comprise, consist essentially of or consist of chitosan and gelatin. In some embodiments, the hydrogel can comprise, consist essentially or of consist of chitosan and laminin. In some embodiments, the hydrogel can comprise cells, constructs and/or implants (e.g., neural stem cells, embryonic stein cells, olfactory ensheathing cells, neural progenitor cells, neural stem cell derived precursor cells, fibroblasts, bone marrow derived stem cell, Dorsal root ganglion, axonal constructs, peripheral nerve implants, Schwann cells and any combination thereof) prior to delivery or administration to a subject. In some embodiments, the hydrogel contains no cells (e.g., no stem cells) prior to delivery or administration to the subject.

In some embodiments of this invention, the hydrogel is designed for sustained release of the factor, agent, or other substance or material present in the hydrogel. Nonlimiting examples include sustained release for at least 5 days, 10 days, 15 days, 20 days, 30 days, 40 days, 50 days, 60 days, etc. To design the hydrogel for sustained release as described herein, the polymer concentration of the hydrogel can be modified. For example higher gelatin concentration stabilizes the hydrogel and slows release of the factor, agent or other substance or material in the hydrogel. The crosslinking density also affects the release rate. This can be modified by adjusting the crosslinking time by adding different cross linkers and changing crosslinker concentration. Finally the factor, agent or other substance or material can be stabilized by adding heparin and/or albumin, which protect the factor, agent or other substance of material and also cause slow and timed release. It would known to one of skill in the art how to determine the appropriate polymer concentration (e.g., a polymer formed by combining chitosan and gelatin in particular ratios as described herein), crosslinker type, crosslinker concentration, heparin and/or albumin concentration, etc., to achieve a particular controlled release rate from the hydrogel as described herein.

The chitosan/gelatin hydrogel of this invention can comprise a crosslinker, nonlimiting examples of which include genipin (covalent cross linker) and glycerol phosphate (ionic crosslinker). In some embodiments, genipin is added first, right after mixing of chitosan and gelatin. This acts as the first crosslinker directly between the ingredients for the formation of the polymer. Glycerol phosphate can be added immediately before application/administration to the subject and further reinforces the structure and gives it the unique property of being a gel at the body temperature of the subject. In some embodiments, the concentration of genipin in the hydrogel can be about 0.4 mM (e.g., about 0.2 mM, 0.25 mM, 0.3 mM, 0.35 mM, 0.4 mM, 0.45 mM, 0.5 mM, 0.55 mM or 0.6 mM, etc.). In some embodiments, the concentration of glycerol phosphate in the hydrogel can be about 3 mg/ml (e.g., 0.1 mg/ml, 0.5 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, 100 mg/ml, etc.)

Further embodiments of the present invention comprise in-situ crosslinkable hydrogels wherein the factor, agent, and/or other material or substance contained therein is present as a nanoparticle. In certain embodiments, the factor, agent, and/or other material or substance will be loaded into a biodegradable nanoparticle, such as PLGA, liposomes, micelles, and/or any other suitable degradable polymers, as are well known in the art.

The hydrogels of this invention can further comprise a polyalkylene glycol (PAG) moiety, which is some embodiments can be poly(ethylene glycol (PEG). The PAG or PEG can have a molecular weight in the range of about 10,000 to about 40,000. The PEG of this invention can be single arm or multi-arm (e.g., 1, 2, 3, 4, 5, 6, 7, 8, 9, or 10 arms, etc.) PEG.

"Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

The present invention is explained in greater detail in the following non-limiting examples.

EXAMPLES

Example 1

Composition of Synthetic Hydrogels

FIGS. 1A-C show human embryonic stem cell derived neurospheres cultured in hydrogels comprising different ratios of 4-Arm PEG and short peptide sequence (CDPVCC GTARPGYIGSRGTARCCAC, SEQ ID NO:1). While all of the hydrogels supported growth of the cells, a PEG:peptide ratio of 25:75 produced the best results.

Example 2

Figure 2A:
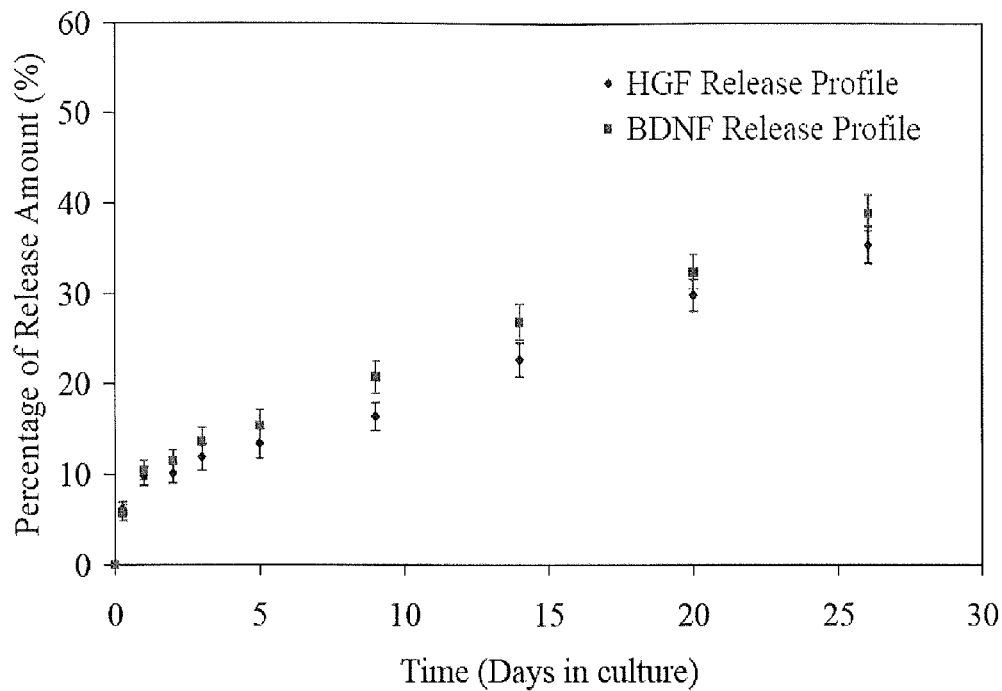
FIGS. 2A-2B show sustained release of biologically active molecules from an ECM-based hydrogel.
Figure 2B:
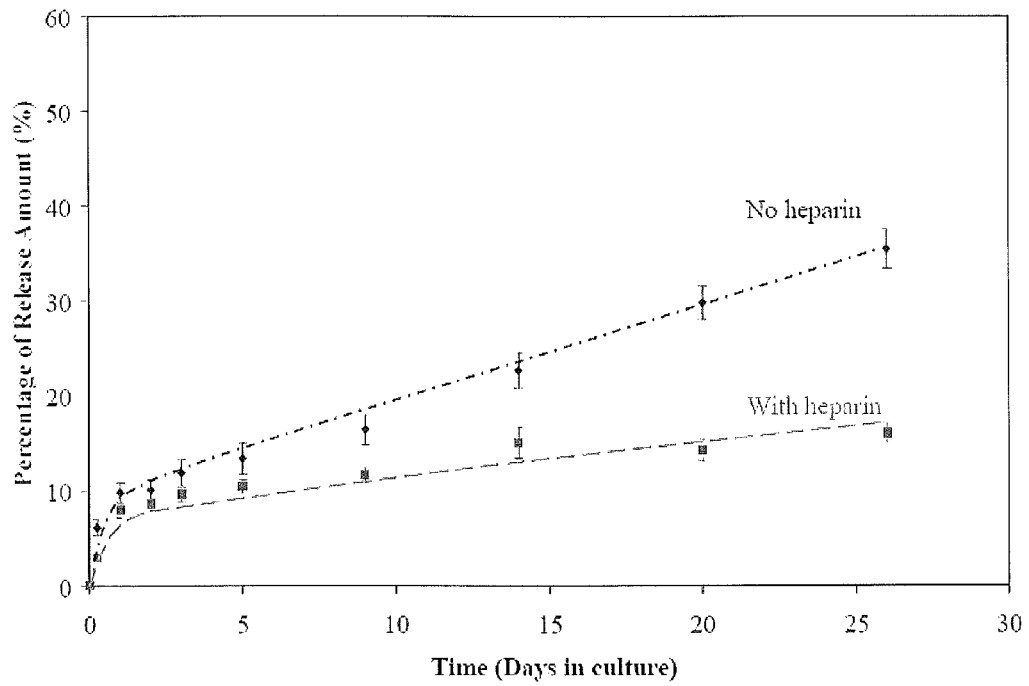
Figure 2C:
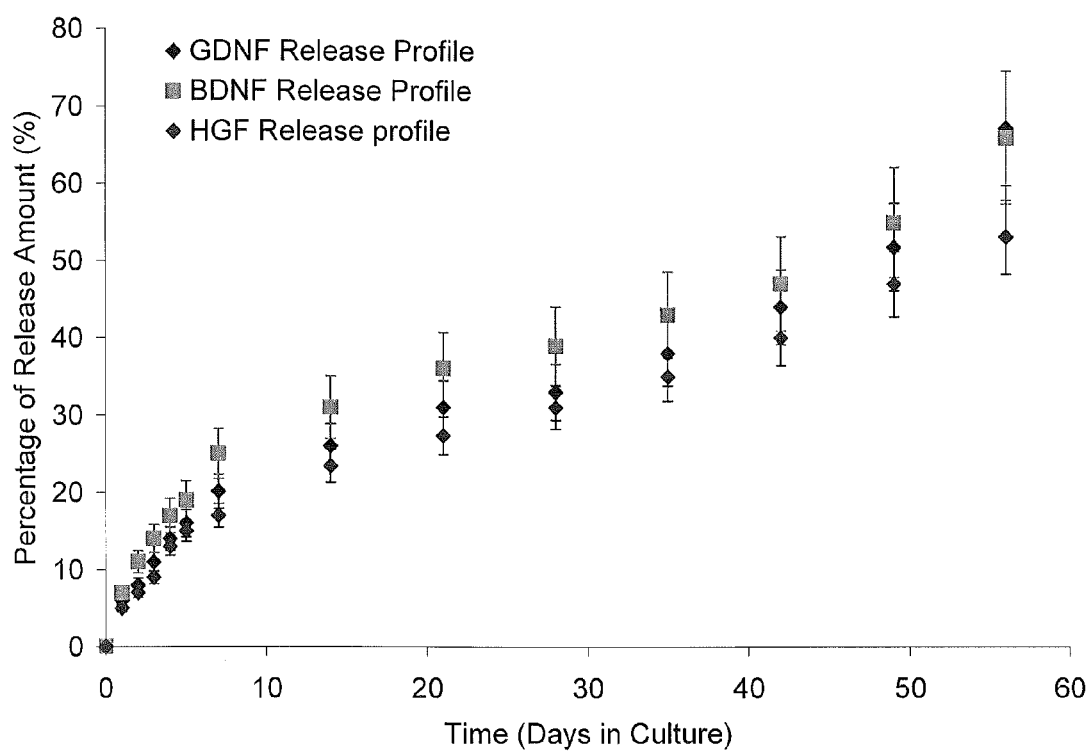
FIG. 2C shows sustained release of biologically active molecules from 4-arm thiolated PEG and thiolated laminin short peptide based hydrogel. Cumulative in vitro GDNF, BDNF and HGF release from the synthetic hydrogel is measured. After 1 and 2 months, about 35% and 70%, respectively, of the growth factors are released.

Sustained Release of Biologically Active Molecules from In-Situ Crosslinkable Hydrogels FIGS. 2A-C show sustained release of biologically active molecules from an ECM-based hydrogel. (A) Cumulative in vitro HGF and BDNF release from an ECM-based hydrogel comprising hyaluronic acid and collagen. After 26 days, approximately 35-40% of each growth factor was released from each hydrogel. (B) Cumulative in vitro HGF release from ECM-based hydrogels comprising hyaluronic acid and collagen (circles), or hyaluronic acid, collagen and heparin (squares). Addition of heparin in HA-collagen hydrogel doubles the release duration of HGF from the hydrogels. The hydrogel provides sustained release of biologically active growth factor in vitro, with release sustained for 3-6 months. This is a dramatic increase in time of availability compared to the short half-life of free growth factors in vivo. (C) Cumulative in vitro GDNF, BDNF and HGF release from the synthetic hydrogel. After 1 and 2 months, about 35% and 70%, respectively, of the growth factors are released.

Example 3

Attracting Stem Cells in Vitro and in Vivo

Figures 3A, 3B:
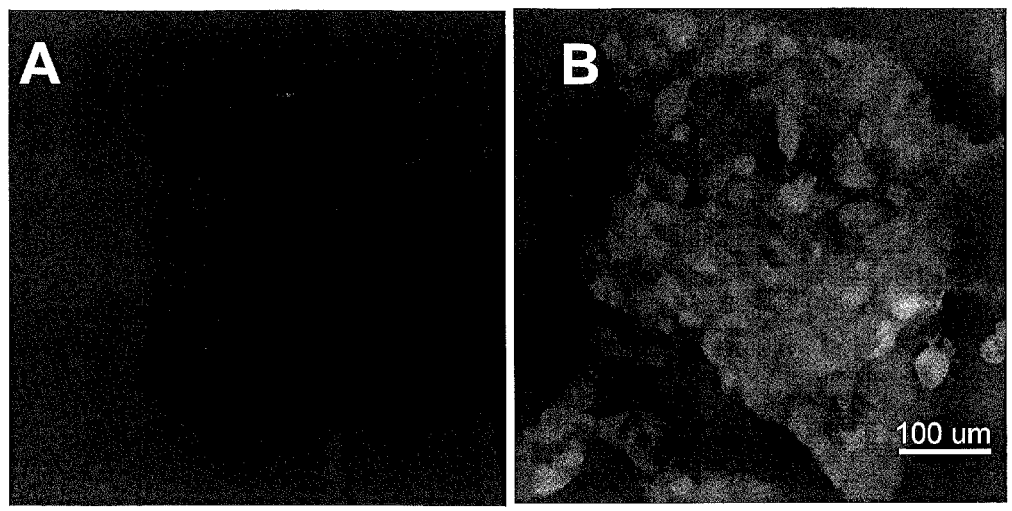
FIGS. 3A-3B show recruitment of stem cells to hydrogels containing hepatocyte growth factor in vitro. Sustained and localized release of HGF from hydrogels (B) is able to induce neural stem cell migration and recruitment into the hydrogel. Dark grey is staining for cell nuclei; black spotting is neurofilament staining, and light grey is nestin staining for neural stem cells. (A) is no HGF control.
Figure 4A:
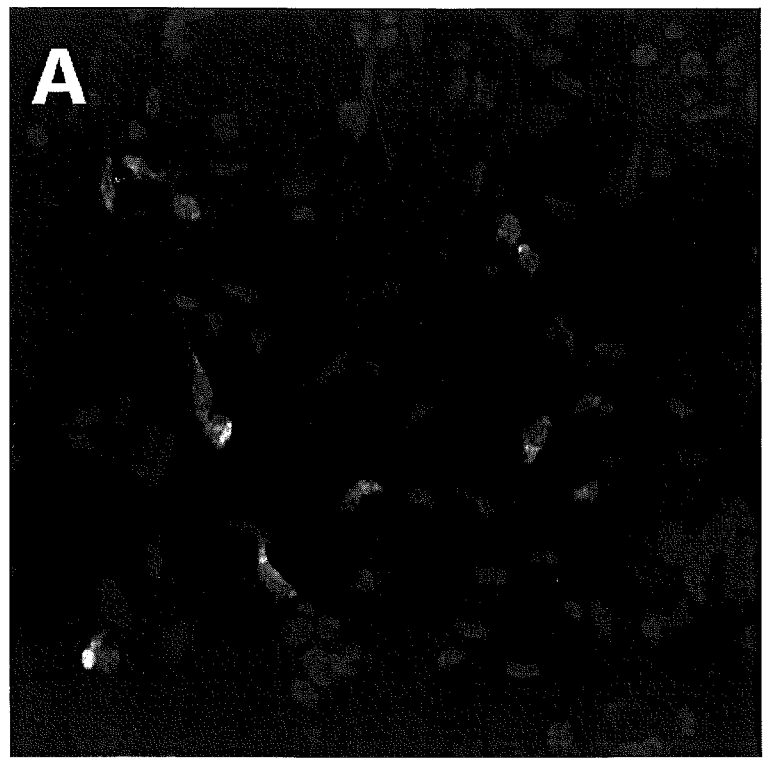
FIGS. 4A-4D show recruitment of endogenous stem cells to hydrogels containing hepatocyte growth factor. ECM-based hydrogels loaded with (A) control or (B) HGF were implanted into the subcutaneous space on the back of mice. Hydrogels were harvested 1 week after implantation, and samples of each were stained. C. Quantitative analysis of the total number of cells that migrated into control and HGF-containing hydrogels. D. HGF-loaded hydrogel stained with anti-STRO-1 following 1 week incubation in the subcutaneous space on the back of a mouse.
Figure 4B:
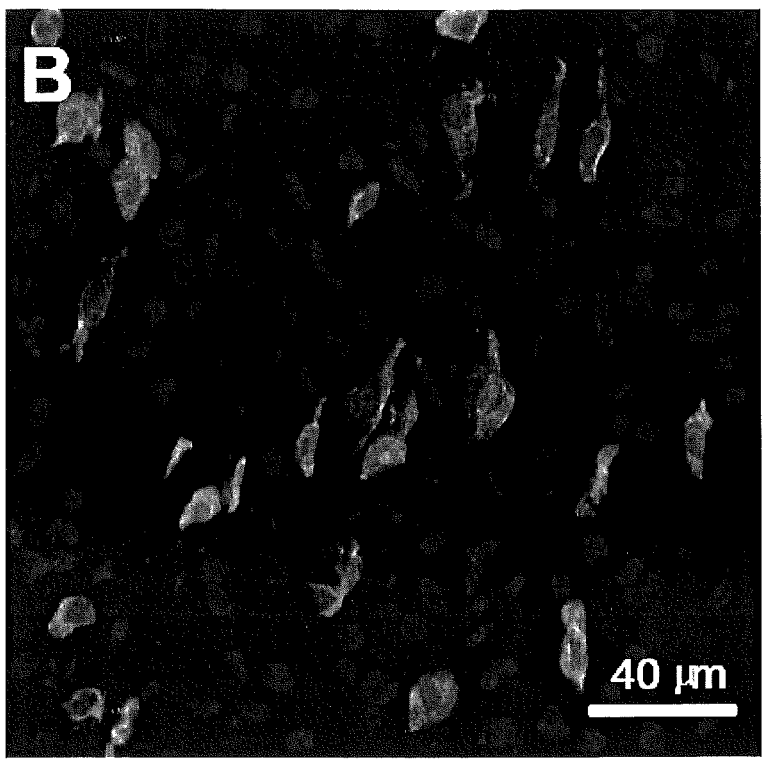
Figure 4C:
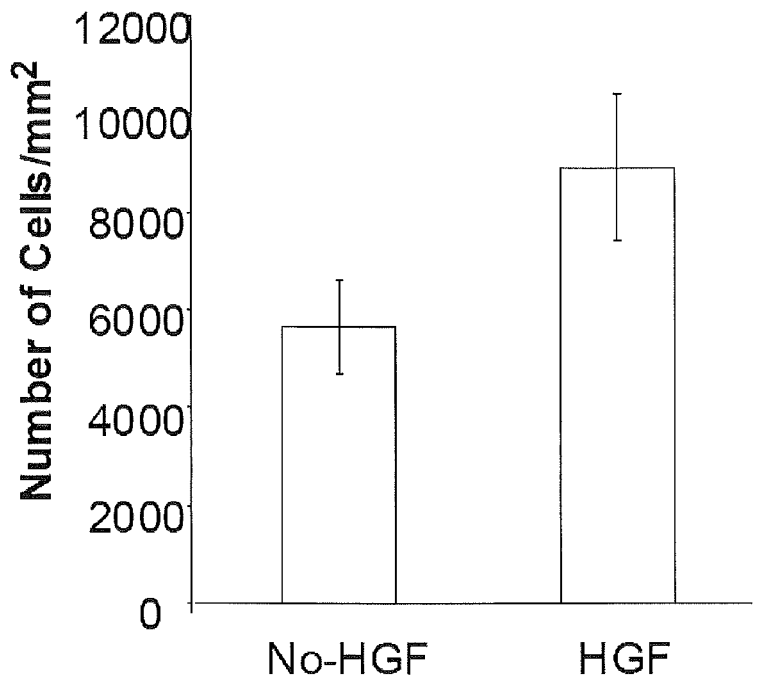
Figure 4D:
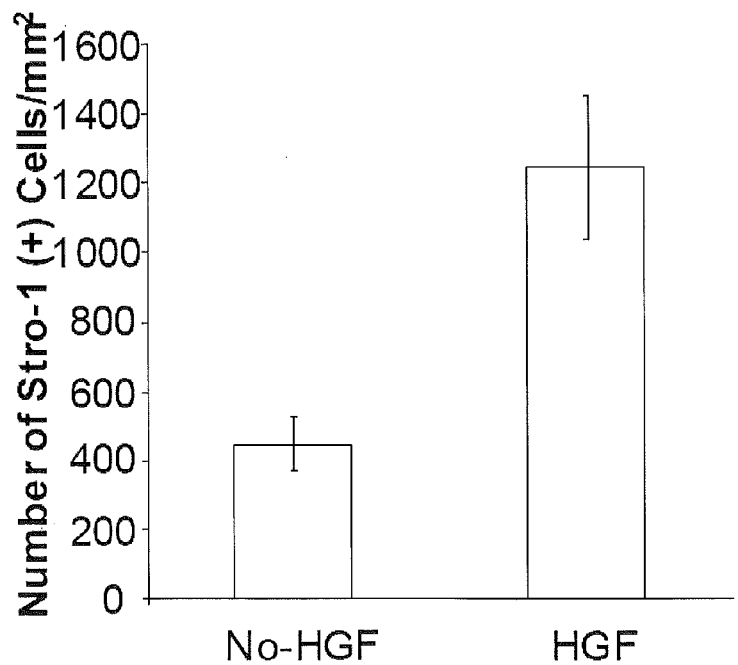
Figure 5A:
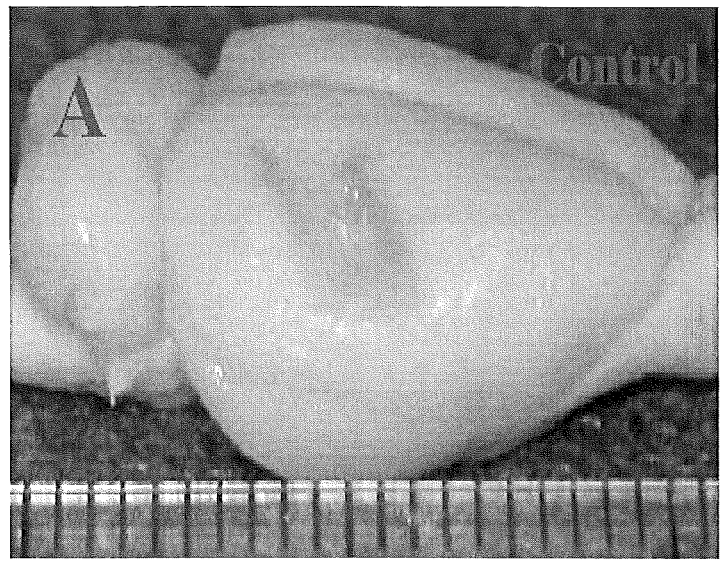
FIGS. 5A-5F show revascularization of a CNS lesion with injection of in-situ crosslinkable hydrogel following stroke.
Figure 5B:
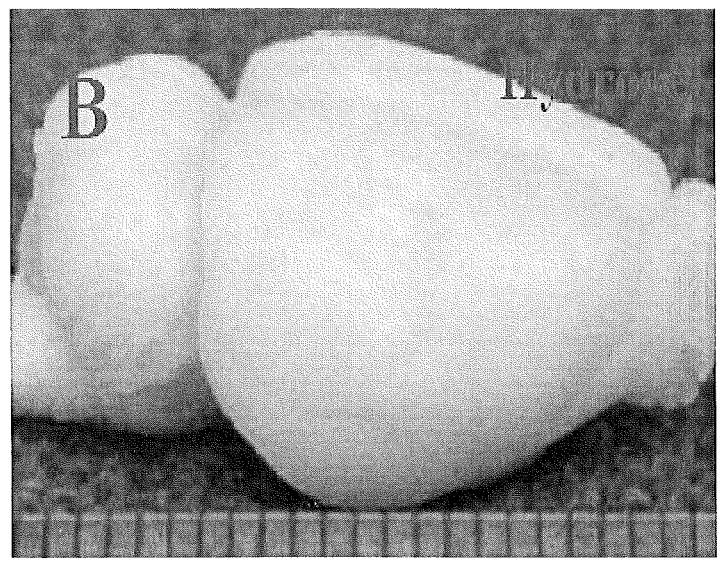
Figures 5C, 5D, 5E, 5F:
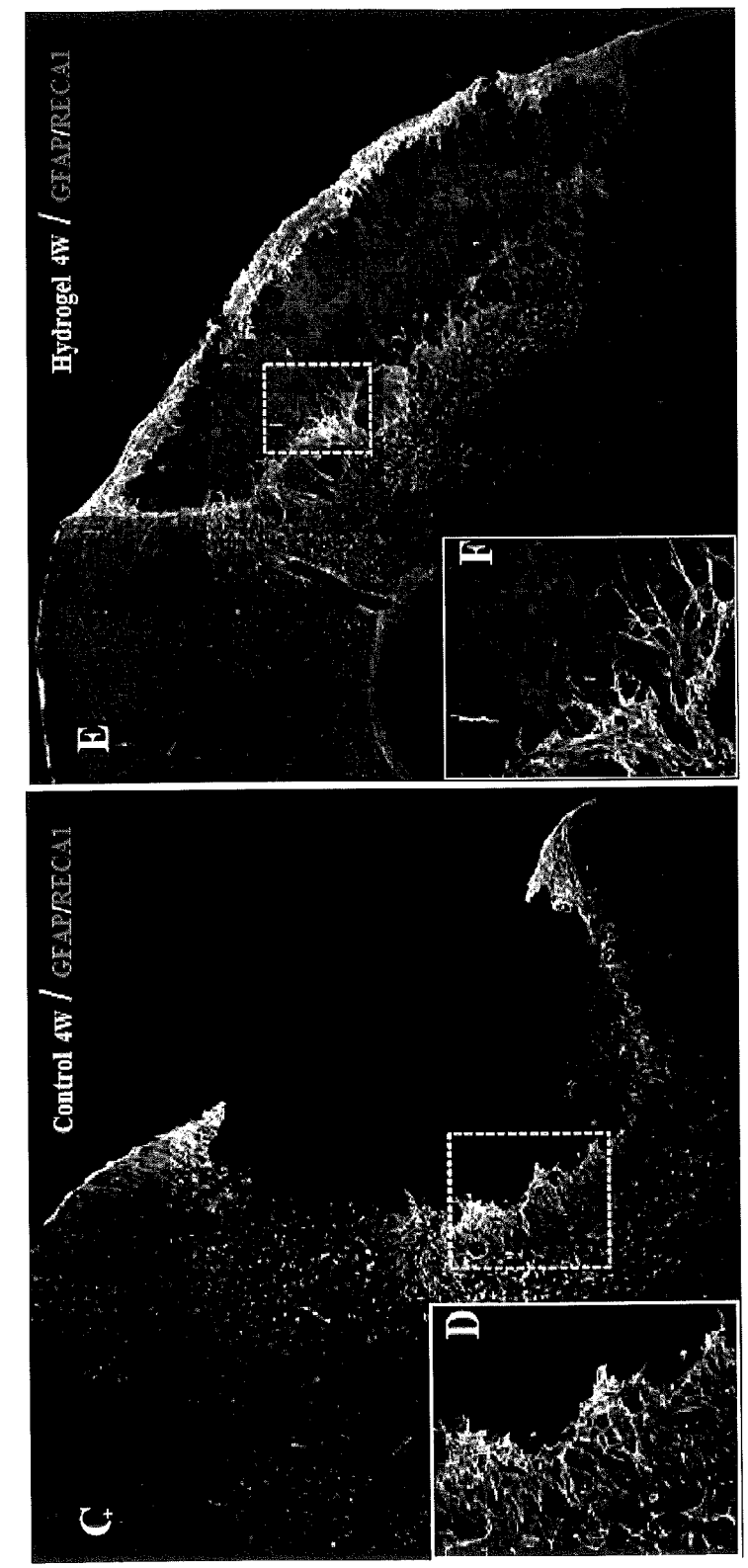
Figures 6A, 6B, 6C, 6D, 6E:
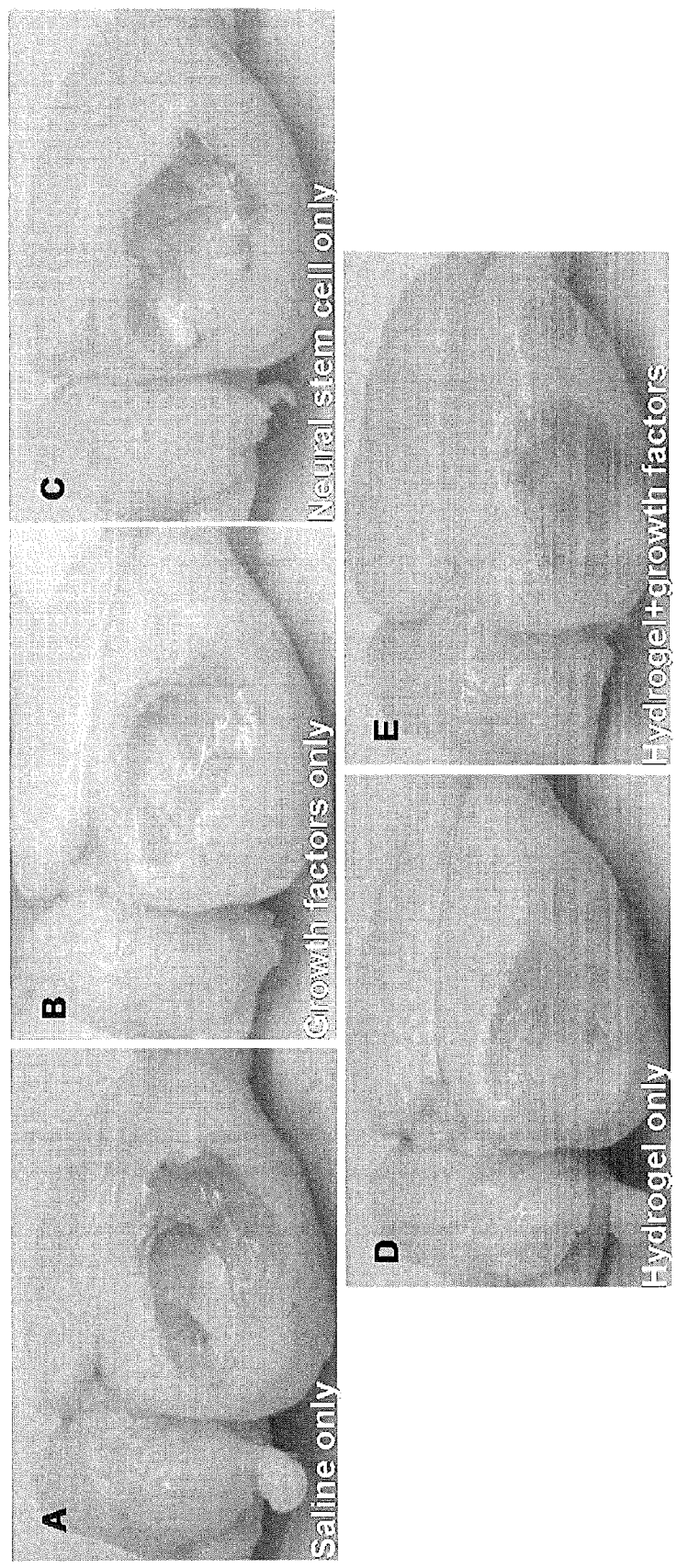
FIGS. 6A-6E show different outcomes after TBI. (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (E) No cavity formation was found 8 weeks after injection of growth factors (HGF, GDNF, BDNF, FGF2) loaded in hydrogel at the 3rd day after traumatic brain injury (TBI).

FIGS. 3A-B show recruitment of stein cells to in-situ crosslinkable hydrogels containing hepatocyte growth factor (HGF). Neural stem cells ($5\times10^3$ in 200 µl culture media) were added to the upper compartment of a transwell. The lower compartment was filled with 400 µl of culture medium and an in-situ crosslinkable hydrogel as control (A), or an in-situ crosslinkable hydrogel containing 80 ng/ml solubilized HGF (B). Hydrogels were harvested following an 8-hour incubation period and stained. Sustained and localized release of HGF from the hydrogel (B) is able to induce neural stem cell migration and recruitment into the hydrogel.

FIGS. 4A-D show recruitment of endogenous stein cells to ECM-based hydrogels containing hepatocyte growth factor (HGF). ECM-based hydrogels loaded with control (A) or HGF (B) were implanted into the subcutaneous space on the back of mice. Hydrogels were harvested 1 week after implantation and samples of each were stained. (C) Quantitative analysis of the total number of cells that migrated into control and HGF-containing hydrogels. (D) HGF-loaded hydrogel stained with anti-STRO-1 following 1 week incubation in the subcutaneous space on the back of as mouse.

Example 4

Stroke Animal Model

FIGS. 5A-F show revascularization of a CNS lesion following stroke. (A, C, D) Adult rat brain four weeks after focal ischemic stroke (untreated). (B, E, F) Adult rat brain treated with an in-situ crosslinkable hydrogel four weeks after focal ischemic stroke. A and B depict the gross morphology of the brains. C and E contain mosaic image reconstructions of the lesions. Higher resolution images of the lesions interfaces are provided in D and F. As shown in panel E, a well-structured vasculature network was rebuilt at the lesion injected with the in-situ crosslinkable hydrogel of this invention.

Example 5

TBI Animal Model

FIGS. 6A-E show different outcomes after traumatic brain injury (TBI). (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (D) No cavity formation was found 8 weeks after injection of growth factors (HGF, GDNF, BDNF, FGF2) loaded in hydrogel at the 3rd day after traumatic brain injury (TBI).

Example 6

Endogenous Neural Stem Cell Recruitment

Figures 7A, 7B:
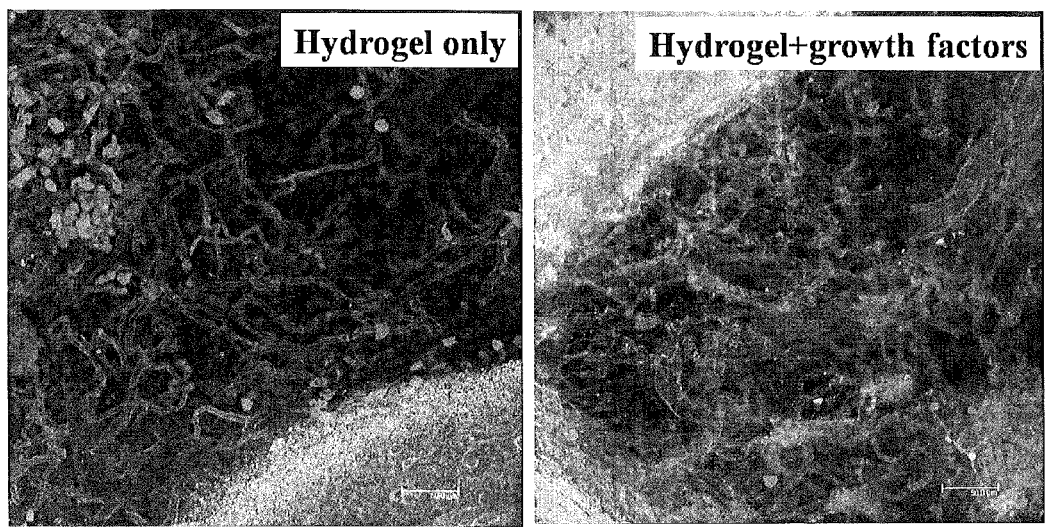
FIGS. 7A-7B. Neural regeneration after hydrogel injection. (A) There is robust vascular formation (light grey), but no neuronal regeneration in the TBI lesion site after only hydrogel injection without the use of growth factor cocktail. (B) There is robust vascular formation and neuronal regeneration (very light grey) after growth factor cocktail (HGF, FGF2, GDNF, BDNF) loaded hydrogel injection.

FIGS. 7A-B show neural regeneration after hydrogel injection. (A) There is robust vascular formation, but no neuronal regeneration in the TBI lesion site after only hydrogel injection without the use of the growth factor cocktail. (B) There is robust vascular formation and neuronal regeneration after growth factor cocktail (HGF, FGF2, GDNF, BDNF)-loaded hydrogel injection.

Example 7

Carrier for Transplantation

Figures 8A, 8B:
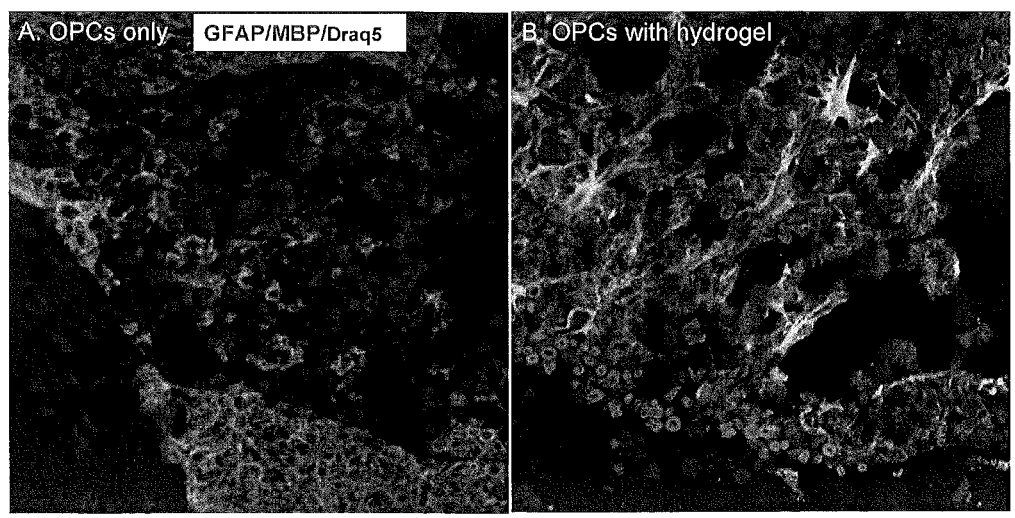
FIGS. 8A-8B. Four weeks after oligodendrocytes precursor cells (OPCs) transplanted into the ethidium bromide localized lesion rat spinal cord. (A) OPC only and (B) OPC transplanted with the hydrogel. Light grey is MBP (myelin basic protein) staining for differentiated oligodendrocytes. Very light grey is GFAP staining for astrocytes and dark grey is Draq-5 staining for cell nuclei. As shown in (B), more functionally viable oligodendrocytes and more myelination are seen in the hydrogel groups.
Figure 9A:
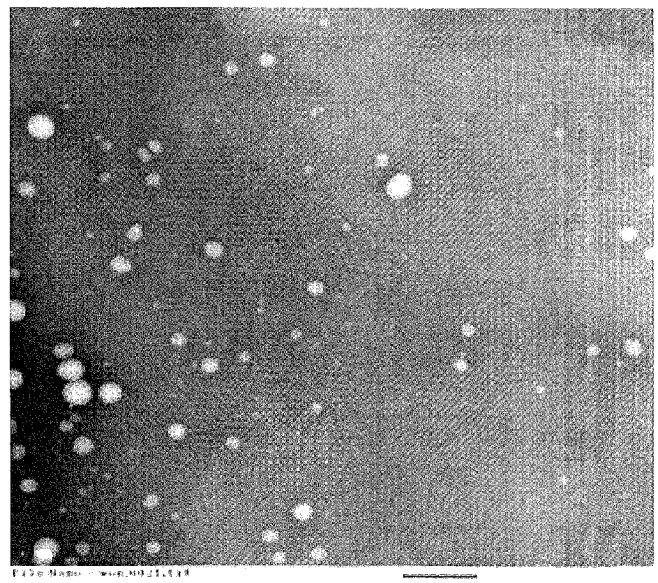
FIGS. 9A-9D. Inhibition of collagen IV biosynthesis using dimethyloxalylglycine (DMOG) nanoparticles. (A) Degradable nanoparticles loaded with DMOG. (B) Size distribution of DMOG-loaded nanoparticles (average size=45 nm). (C) Nanoparticles stained with anti-collagen IV antibody 4 weeks after the implantation of control nanoparticles. (D). nanoparticles containing DMOG. Scale bar=75 um. Dotted lines indicate the borders of implanted hollow fibers.
Figure 9B:
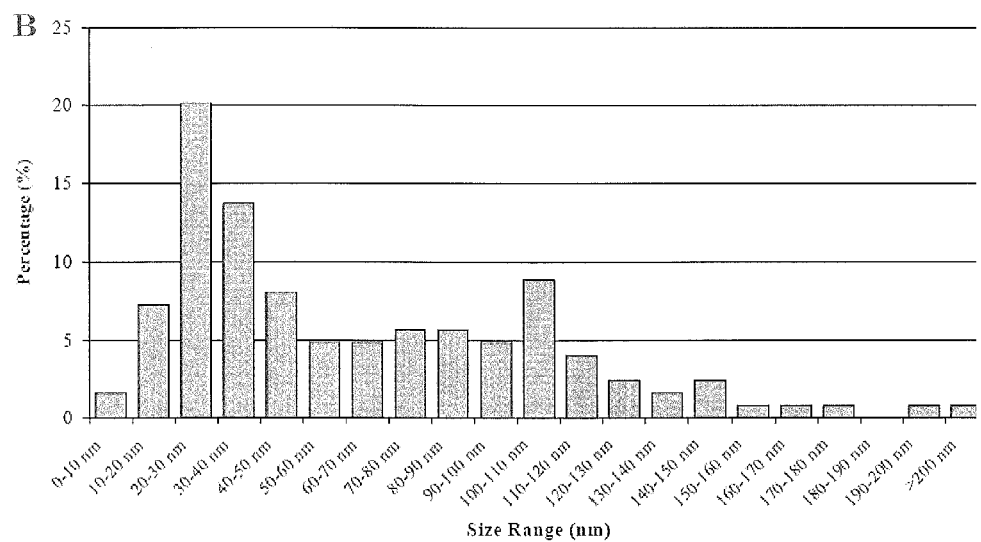
Figures 9C, 9D:
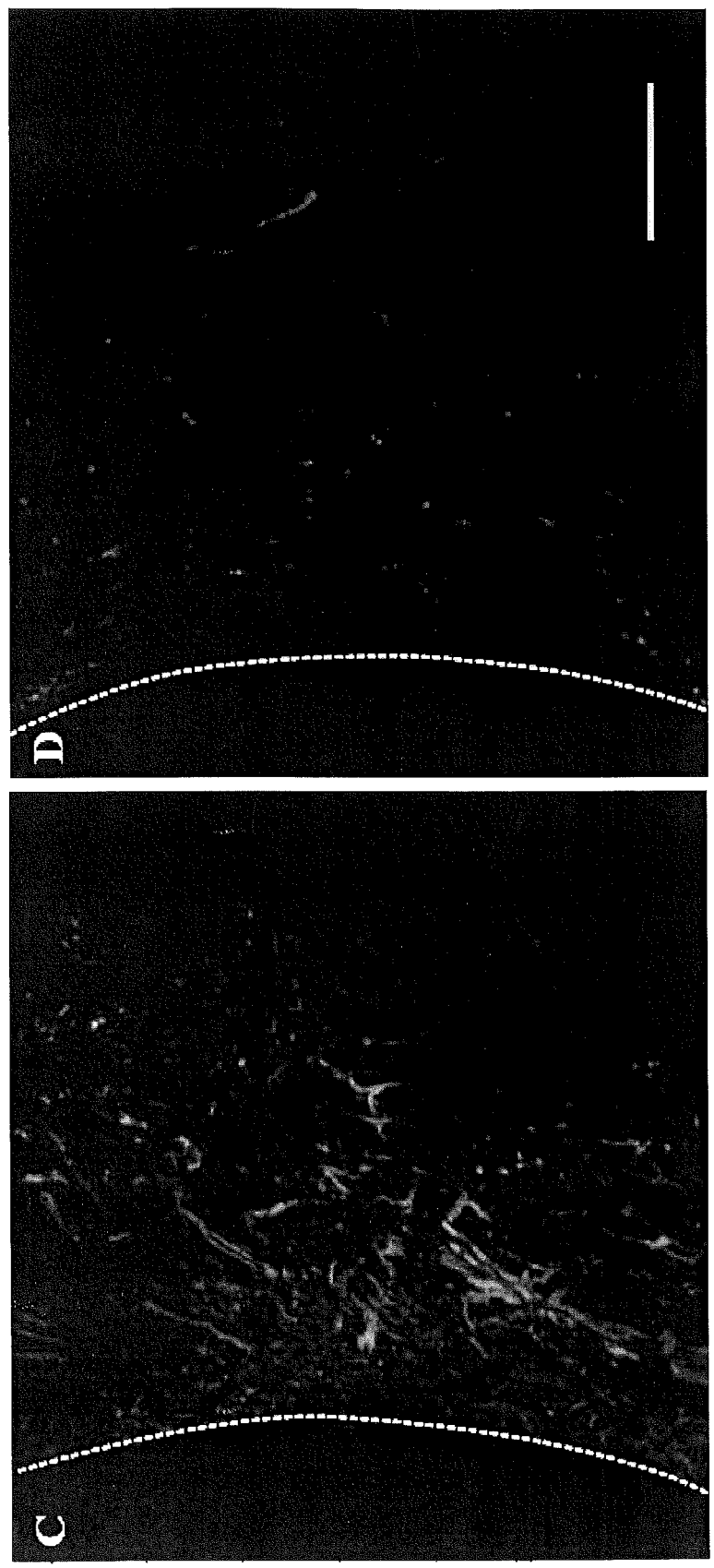

Myelin is damaged in many diseases, such as multiple sclerosis (MS) and leukodystrophies. Myelin is also destroyed in neural tissue injury, such as spinal cord injury (SCI) and traumatic brain injury (TBI). Remyelination has to occur in order to cure these diseases and is also the key step to fully regenerate injured spinal cord or brain tissue. At present, there are no effective therapies in the clinic that promote remyelination. There is growing evidence that exogenous cell transplantation is one promising strategy to promote remyelination. However, direct injection of neural stem cells or oligodendrocyte precursor cells (OPCs) to the lesion site may not be an optimal therapeutic strategy since the viability and functionality of transplanted cells are compromised by the local hostile environment, e.g., in MS disease sites. There is an urgent need to find effective strategies to improve remyelination. In order to improve the viability of the transplanted cells, the microenvironments of the diseased tissue has to be re-conditioned for transplanted cells to survive. One way to manipulate the local microenvironment is to use an injectable neural biocompatible hydrogel system loaded with factors to provide a regeneration permissive microenvironment. To this end, hydrogels made of multi-arm polyethylene glycol (PEG) and modified short laminin peptide sequence were used as a carrier for cell transplantation. These hydrogel systems support remyelination. FIG. 8 shows that increased myelination occurred when OPCs are transplanted with these hydrogels Example 8

Nanoparticles

FIGS. 9A-D show inhibition of collagen IV biosynthesis using dimethyloxalylglycine (DMOG) nanoparticles. (A) Degradable nanoparticles loaded with DMOG. (B) Size distribution of DMOG-loaded nanoparticles (average size=45 nm). (C, D) Nanoparticles stained with anti-collagen IV antibody 4 weeks after the implantation of control nanoparticles (C) or nanoparticles containing DMOG (D). Scale bar=75 um. Dotted lines indicate the borders of implanted hollow fibers.

Example 9

Functional Outcomes After Application of Chitosan-Gelatin Hydrogel in a Rat Model of Severe Spinal Cord Injury The studies described herein employ a chitosan-gelatin hydrogel system. This hydrogel is non-neurotoxic and possesses the unique property of gelation at body temperature from its liquid form at room temperature. To maximize therapeutic benefits this hydrogel was loaded with glial derived neurotrophic factor (GDNF). The therapeutic effects of this hydrogel were tested in a rat model of severe acute spinal cord injury.

Fabrication of Chitosan-Gelatin Hydrogel

Chitosan and gelatin are two naturally occurring polymers. Chitosan is a polysaccharide formed by cross linkage of multiple monosaccharide units. It has active acetyl groups available for cross linkage. At acidic pH, chitosan is able to undergo polymerization. Gelatin is a peptide polymer and chemically derived from denatured collagen. It is a part of extracellular matrix and has been shown to be important for extracellular signaling. Chitosan and gelatin co-polymer can be created by mixing chitosan with gelatin using a standard and well known procedure that involves creating acidic pH for chitosan polymerization followed by mixing with heated and stirred gelatin solution. However there are two disadvantages of this approach—high osmolarity of the resultant solution (>500 mM) and acidic pH. There are also concerns for cytotoxicity to biological tissues at such high concentrations. These disadvantages render the use of this copolymer useless for clinical application. In the present invention, chitosan and gelatin were cross linked by two different approaches—the first was a covalent linkage using genipin followed by using ionic cross linkage using glycerol phosphate. Genipin is a plant derived cross linker and quite cheap. The safety and cytotoxic profile of genipin was evaluated and a concentration of 0.4 mM was found to be safe in the in vitro cell cultures. This concentration of genipin was added to chitosan and gelatin mixture. Genipin is able to covalently link both the saccharide and amine groups available in chitosan and gelatin, respectively. This creates a polysaccharide-peptide cross linkage. The addition of genipin offers the advantage of creating a stable co-polymer which is stable over a wide range of temperature. It is in liquid state at room temperature which renders it easy for therapeutic delivery. This copolymer can be easily stored in frozen state and autoclaved for biological applications. At the time of clinical application glycerol phosphate is added for ionic cross linkage. Various concentrations of glycerol phosphate can be utilized depending on the physical property desired. The representative concentrations can be 0.1 mg/ml to 100 mg/ml. Specifically the concentration of 3 mg/ml was tested for this study. Glycerol phosphate has active phosphate moieties that result in further cross linkage between chitosan and gelatin. This provides a clinically useful property of quick gelling of the hydrogel within 30 minutes at room temperature. The osmolarity of this co-polymer can be from about 150 mM to about 300 mM (e.g., 100 mM, 150 mM, 200 mM, 250 mM, 300 mM, 350 mM, 400 mM), which is desirable for clinical application.

GDNF was mixed in a concentration of 75 microgram per mL of hydrogel. Nonlimiting examples of the concentration of GDNF or other growth factor include about 25 microgram per mL to about 250 microgam per mL (e.g., about 25, 50, 75, 100, 125, 150, 175, 200, 225, 250 microgram per mL, etc.)

Chitosan and gelatin were mixed in varying ratios from 0.5-15 to 15-0.5. The ratio of 6:4 was chosen due to its facile gelling properties. The hydrogel polymer was prepared with a synergistic contribution of covalent and ionic crosslinking. A polymer solution was first cross linked via covalent bonds using genipin in low extent to allow easy flow, and then ionic cross linker, glycerol phosphate, was added to reach a facile gelling within about 30 minutes. Growth factor (GDNF) was loaded immediately after ionic cross linker was added.

Animals and Induction of Spinal Cord Injury

All animal experiments were conducted according to the established institutional protocol and NIH guidelines for animal studies. Adult, female Sprague Dawley (SD) rats were used in this study. T10 laminectomy was performed in a standard fashion and severe contusive spinal cord injury was induced with computer-controlled impactor. This technique has previously been shown to yield severe spinal cord injury (Horn et al. "The effects of intrathecal hypotension on tissue perfusion and pathophysiological outcome after acute spinal cord injury" *Neurosurg Focus* 25(5):E12 (2008)).

Animals were divided into one control and four experimental groups. The experimental groups received injection of hydrogel alone (N=10), injection of hydrogel with GDNF (N=8), topical application of hydrogel (N=10), and topical application of hydrogel mixed with GDNF (N=8). The injury only control group received no intervention (N=8). For the injection groups, pre mixed preparations of the hydrogel were injected slowly at the injury site. In the topical application groups, the dura was carefully opened and pre-mixed hydrogel was placed on the exposed surface of injured spinal cord. Post-procedure rats received standard post spinal cord injury care including nutritional support, adequate hydration, pain control, bladder expression three times a day and treatment of complications including urinary tract infections.

Histology and Immunohistochemistry

Animals were sacrificed after 8 weeks of observation. The spinal cord was carefully removed and fixed with paraformaldehyde. Post fixed samples were cut longitudinally and mounted on microscope slides. For immunostaining, sections were permeabilized and blocked with 4% normal goat serum. Primary antibodies were then applied overnight at 4° C. The following primary antibodies were used: REC-1, β-3 tubulin, glial fibrillary acidic protein (GFAP), myelin basic protein (MBP), human macrophage glycoprotein CD-68 and chondroitin sulfate proteoglycan (CSPG).

Assessment of Functional Outcomes

Weekly behavioral assessments were carried out for 8 weeks. Two pre-trained researchers made independent observations about hind limb function. The animals were placed in an observation area with transparent walls and observed for approximately 2-4 minutes each. Functional improvement was measured using the Beattie, Breshnan, and Basso scale (BBB scale) (Basso et al. "A sensitive and reliable locomotor rating scale for open field testing in rats" (*J Neurotrauma* 12(1):1-21 (1995); Basso et al. "Graded histological and locomotor outcomes after spinal cord contusion using the NYU weight-drop device versus transaction" *Exp Neurol* 139 (2):244-256 (1996))

Data Analysis

The results from immunohistochemistry were qualitatively assessed and reported. Data were entered in Microsoft Excel® software and analyzed in SPSS® version 19 software. Mean (±SD) BBB scores were calculated for experimental and control groups.

Behavioral Scores

The contusion model consistently resulted in minimal recovery. The BBB scores of the hydrogel only group were similar to the scores in the control group implying that neither the hydrogel nor the method of administration had significant negative effects on functional recovery. The topical groups (topical and topical+GDNF) demonstrated partial recovery. The hydrogel with GDNF group resulted in maximum improvement consistently across 8 weeks.

Immunohistochemistry

Staining revealed decreased astrogliosis and preservation of axonal bridge at the injury epicenter.

Conclusions

In this study, functional recovery after severe contusion SCI in rats was demonstrated using a chitosan-gelatin hydrogel mixed with GDNF. Preservation of axons across the lesion epicenter may be a result of neuroprotection.

Example 10

Chitosan-Gelatin Hydrogel Based Delivery of Glial Derived Neurotrophic Factor Prevents Secondary Injury in a Rat Model of Severe Spinal Cord Injury Secondary injury results in exacerbation of axonal loss and poor functional recovery after spinal cord injury (SCI). A chitosan-gelatin hydrogel was designed for prevention and limitation of secondary injury. The histological and functional outcomes were evaluated after application of this hydrogel in a rat model of SCI.

Fabrication of Chitosan-Gelatin Hydrogel-Amounts

Chitosan and gelatin are mixed in ratios of gelatin/chitosan varying from 0.5:15 to 15:0.5. As described above a ratio of 6:4 was chosen due to favorable physical properties. Genipin and proanthocyanidin are used as covalent cross linkers while glycerol phosphate was used as the ionic cross linker. Genipin and proanthocyanidin are plant-derived and are much less toxic than most synthetic cross linkers. Glycerol phosphate is non-toxic as far as the osmolarity is controlled around physiological value. The injectable hydrogel was prepared with a synergic contribution of covalent and ionic crosslinkings. A polymer solution was first cross linked via covalent bonds in low extent that allows the system still flows easily, and then ionic cross linker is added to reach a facile gelling within about 30 minutes. Growth factors when included are loaded immediately after ionic cross linkers.

Animals and Induction of Spinal Cord Injury

All animal experiments were conducted according to the established institutional protocol and NIH guidelines for animal studies. 36 adult, female Sprague Dawley (SD) rats were used in this study. Rats were anesthetized with weight-based intra-peritoneal injection of 4% chloral hydrate. T10 laminectomy was performed in a standard fashion. Severe contusive spinal cord injury was induced with computer-controlled impactor with a velocity of 4 cm/sec with an impact depth of two millimeters. This technique has previously been shown to yield severe spinal cord injury.

Animals were divided into four experimental and two control groups. The experimental groups received injection of hydrogel alone (N=8), hydrogel injection with GDNF (N=6), topical application of hydrogel (N=7), and topical application of hydrogel mixed with GDNF (N=8). The injury only control group received no intervention (N=6), while the sham surgery group (N=1) underwent surgery without injury being induced. For the gel injection groups, pre mixed preparations of the hydrogel were injected at six different sites proximal, within and distal to the lesion bilaterally. By using 6 injection sites the maximal diffusion of the gel throughout the lesion site was ensured. To minimize injection related damage, the hydrogel was administered at a depth of 1 mm (assuming the average spinal cord diameter of 3 mm) at a rate of 10 μl/minute and single injection volume of 10 μl. The microinjector was carefully withdrawn following visual confirmation of gelation. In the topical application groups, after induction of injury, the dura was carefully opened and 60 μl of pre-mixed gel was placed on the exposed spinal cord. The wound was subsequently closed in multiple layers. After these procedures, rats received standard post spinal cord injury care including nutritional support, adequate hydration, pain control, bladder expression three times a day and treatment of complications including urinary tract infections.

Histology and Immunohistochemistry

Rats were sacrificed after eight weeks of observation. After induction of anesthesia with sevoflurane, the rats were transcardially perfused initially with phosphate buffered saline (PBS) and then with 4% paraformyldehyde. The spinal cord was carefully removed and fixed with paraformayldehyde for 24 hours followed by 30% sucrose. Postfixed samples from the transplant site were cut longitudinally at the epicenter of the lesion and mounted with the cut surfaces facing down in TBS tissue freezing medium. Twenty um thick transverse sections were cut on a cryostat and mounted on microscope slides. For immunostaining, sections were permeabilized and blocked with 4% normal goat serum. Primary antibodies are then applied overnight at 4° C. The following primary antibodies are used: with REC-1, axonal regeneration with β-3 tubulin, astrogliosis with glial fibrillary acidic protein (GFAP), myelination with myelin basic protein (MBP), macrophages with CD-68 and scar tissue with chondroitin sulfate proteoglycan (CSPG). Alexa Fluor secondary antibodies, goat anti mouse, and rabbit 488, 594, and 647 are used at 1:400 (Invitrogen, Carlsbad, Calif.).

Assessment of Functional Outcomes

Behavioral assessments were carried out every week on the same day for 8 weeks following injury and intervention. Because discomfort immediately following surgery and complications associated with SCI can influence functional scores, the first behavioral assessment was carried out at the one week postoperative time point (Basso et al. "Behavioral testing after spinal cord injury: congruities, complexities, and controversies" *J Neurotrauma* 21(4):395-404 (2004). The time at which these assessments were conducted was maintained throughout the duration of the study in order to further standardize the assessment. Two pre-trained researchers made independent observations about hind limb function. The animals were placed in an observation area with transparent walls and observed for approximately 2-4 minutes each. A video recording was also carried out for future reference. Functional improvement was measured using the Beattie, Breshnan, and Basso scale (BBB scale).

Data Analysis

The results from immunohistochemistry were qualitatively assessed and reported. Data were entered in Microsoft Excel® software and analyzed in SPSS® version 19 software. Mean (±SD) BBB scores were calculated for experimental and control groups.

Animal Surgery and Survival

Most of the animals tolerated surgical procedures well, with approximately 90% rate of survival at 8 weeks follow up. Animals that seemed to develop discomfort from sores, or urinary tract infection were sacrificed prior to completion of the study and any data collected prior to sacrifice was excluded.

Immunohistochemistry

Inflammation, Astrogliosis, and Scar Formation
Preserved Axonal Bridge And Myelination Across the Injury Site
Angiogenesis Behavioral Scores The contusion model resulted in BBB scores around 1 to 2 yielding a consistent severe SCI model. Some animals demonstrated minor improvements at the first observation more than a week removed from surgery.

The BBB scores of the gel only group were similar to the scores of the control group implying that neither the gel nor the method of administration had significant negative effects on functional recovery. The topical groups (topical and topical+GDNF) demonstrated partial recovery with average BBB scores of 4 (95% CI 1.9-6.1) and 4.06 (95% CI 2.07-6.05) respectively. The hydrogel with GDNF group resulted in maximum improvement which was consistent across 8 weeks (BBB score of 4.33, 95% CI 1.88-6.78). This trend towards improvement was not statistically significant.

A trend towards improvement in hind limb function was observed in the experimental group that received GDNF mixed with chitosan-gelatin hydrogel. Three out of six animals showed movement in all three joints in this group as compared to one out of eight in gel only and one of out six in injury only groups. Although the improvement was gradual over the course of eight weeks, some animals showed significant improvement within the first 10-17 days. Release of neurotrophic factors from this hydrogel slowly over 4 weeks has been demonstrated. Preservation of axons across the lesion epicenter may be a result of both neuroprotection from secondary injury and regeneration.

In this investigation, prevention of axonal loss from secondary injury in a severe contusion spinal cord injury in rats using a chitosan-gelatin hydrogel mixed with GDNF was demonstrated.

A contusion model of severe spinal cord injury was used in this study because it closely emulates clinical presentation. Although a transection model yields consistent, severe spinal cord injury, it seldom represents the human spinal cord injury pattern. Axonal regeneration across the transection cavity proves the effectiveness of the experimental strategy in a lab setting, however the applicability of such results in a clinical setting is speculative. To ensure a uniform distribution of hydrogel, six injection sites proximal, distal, and within the lesion epicenter were selected. A potential disadvantage of multiple injections is the potential of further trauma and foreign body reaction. The microinjection was carried out very slowly at a depth of 1 mm to minimize such adverse reactions.

Example 11

Functional Outcomes After Injection of Chitosan-Gelatin Hydrogel in a Rat Model of Severe Spinal Cord Injury Introduction Functional recovery after severe spinal cord injury is modest due to inhibition of axonal regeneration by several intrinsic factors. Poor axonal regeneration results in limited functional improvement after spinal cord injury. An injectable chitosan-gelatin hydrogel was developed for delivery of neurotrophic factors and/or supporting cells and for enhancement of delivery of neurotrophic factors for axonal regeneration. The functional outcomes were evaluated after injection of this hydrogel in rat model of severe spinal cord injury.

Methods

Twenty eight adult SD rats were randomly assigned to two control (sham surgery (N=2), spinal cord injury only (N=6)) and three experimental groups (hydrogel injection (N=8); hydrogel with GDNF injection (N=6); hydrogel, GDNF and oligodendrocyte precursor cell (OPC) injection (N=6)). Spinal cord injury was induced by a computer controlled impactor with a diameter of 3 mm and depth of 2 mm at a speed of 4 cm/sec. 10 μL of hydrogel solution was administered by injection at six different points bilaterally distal, proximal and within the injury site slowly over one minute. All animals were followed for 8 weeks and weekly behavioral testing was performed using the BBB scale (minimum 0, maximum 21). Subsequently animals were sacrificed and spinal cords removed for studying axonal regeneration and myelination. Immunohistochemical staining with REC-1 (vascularization), β-3 tubulin (axonal regeneration), GFAP (astrogliosis) MBP (myelination) and CD-68 (macrophage) was performed.

Results

Figure 10:
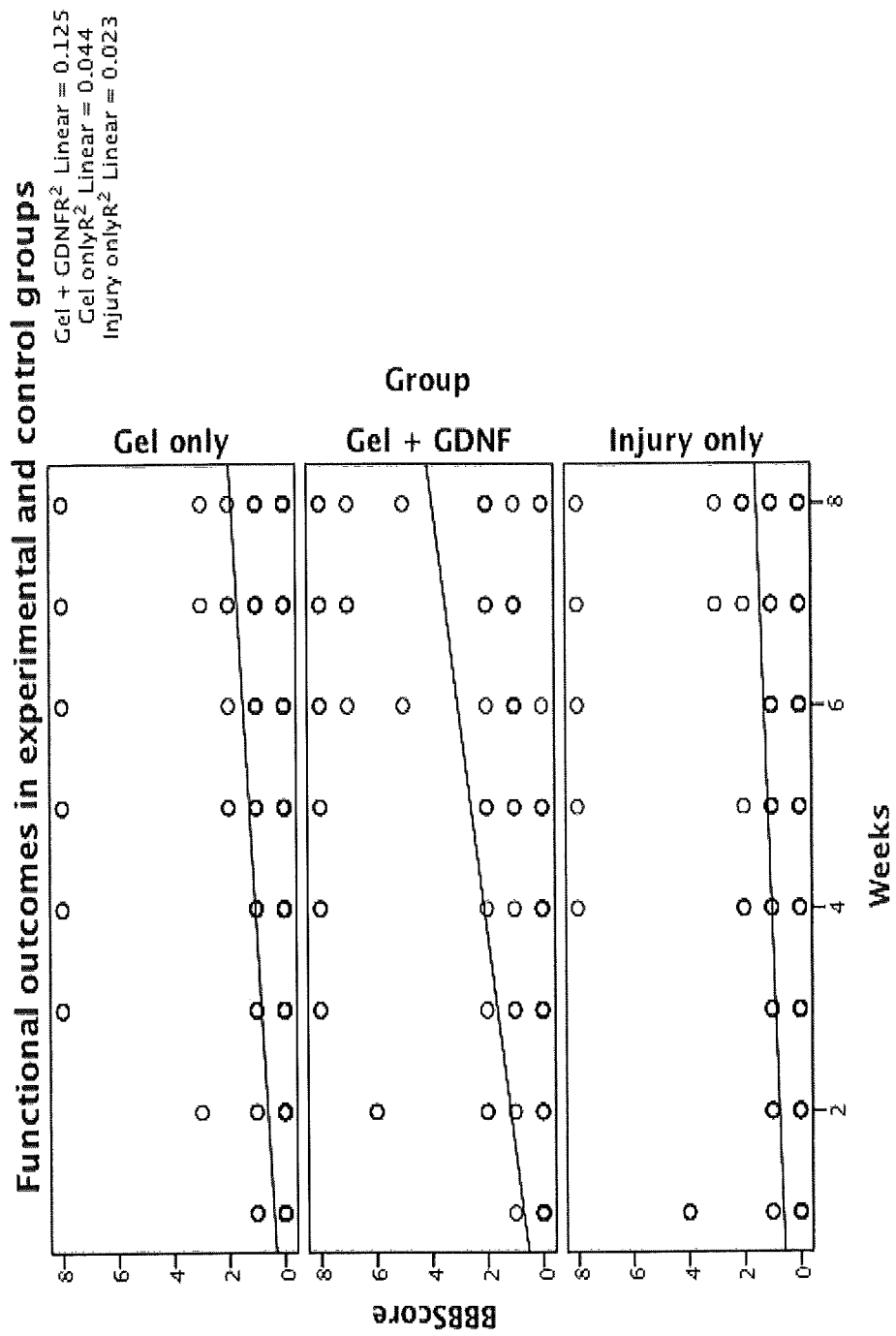
FIG. 10. Scatter plots depicting functional outcomes.
Figure 11:
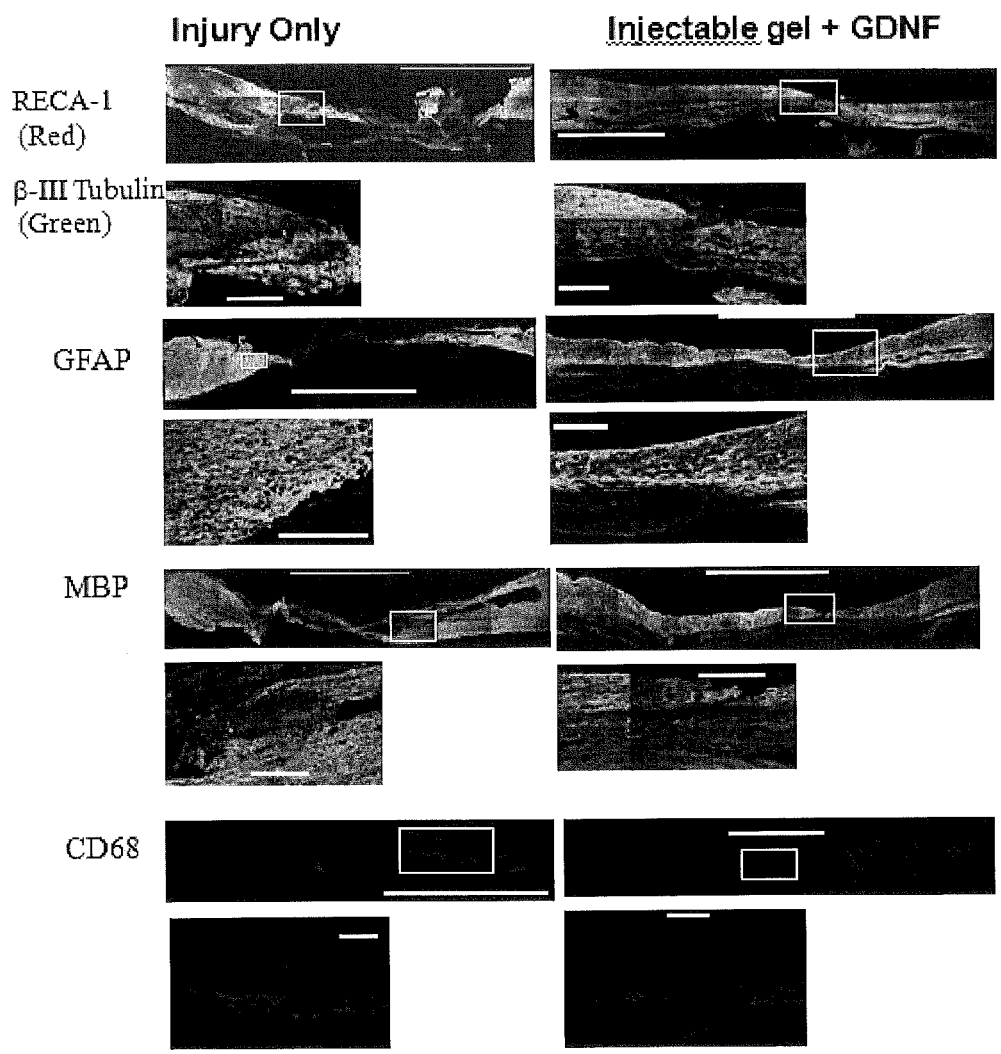
FIG. 11. Immunostaining of control and gel with GDNF groups.

The mean BBB scores (FIG. 10) for control group at eight weeks was 1.67 (95% CI 0.39-2.95). The hydrogel injection did not seem to adversely affect functional recovery (BBB score of gel only group —1.56 (95% CI 0.26-2.86)). The functional score improved with the inclusion of GDNF (BBB score—4.33 (95% CI 1.88-6.78)) but not with simultaneous inclusion of GDNF and OPCs (1.75, 95% CI—0.05-3.1). GDNF in the gel preparation results in preservation of tissue bridge across the injury site (FIG. 11). This bridge has abundant blood vessels and astrocytes. Myelinated axons were observed as well. Although there is evidence of inflammation it appears to be lesser than the control group.

Conclusions

The chitosan-gelatin based injectable hydrogel medium improves functional outcomes when combined with GDNF in a rat model of severe spinal cord injury. Preservation of supporting environment (blood vessels and astrocytes) and decreased inflammation appear to be primary mechanisms of improved functional outcomes.

Example 12

Functional Outcomes After Topical Application of Chitosan-Gelatin Hydrogel for in a Rat Model of Severe Spinal Cord Injury Introduction Functional recovery after severe spinal cord injury is modest due to inhibition of axonal regeneration by several intrinsic factors. Loss of axonal membrane integrity results in significant neuronal loss after spinal cord injury. A topical chitosan-gelatin hydrogel was designed for stabilizing the damaged axonal membrane and simultaneously delivering neurotrophic factors. The effects of this hydrogel were tested in rat model of severe spinal cord injury.

Methods

Twenty three adult SD rats were randomly assigned to two control (sham surgery (N=2), spinal cord injury only (N=6)) and two experimental groups (topical hydrogel application (N=7) and topical hydrogel with GDNF (N=8)). Spinal cord injury was induced by a computer controlled impactor with a diameter of 3 mm and depth of 2 mm at a speed of 4 cm/sec. The dura was opened widely to expose the injured segment. 60 μL of hydrogel solution was topically administered and allowed to gelate before closure. All animals were followed for 8 weeks and weekly behavioral testing was performed using the BBB scale (minimum 0, maximum 21). Subsequently animals were sacrificed and spinal cords removed for studying axonal regeneration and myelination. Immunohistochemical staining was performed to study vascularization (REC-1), axonal regeneration (β-3 tubulin), astrogliosis (GFAP), myelination (MBP) and inflammation (CD-68).

Results

Figure 12:
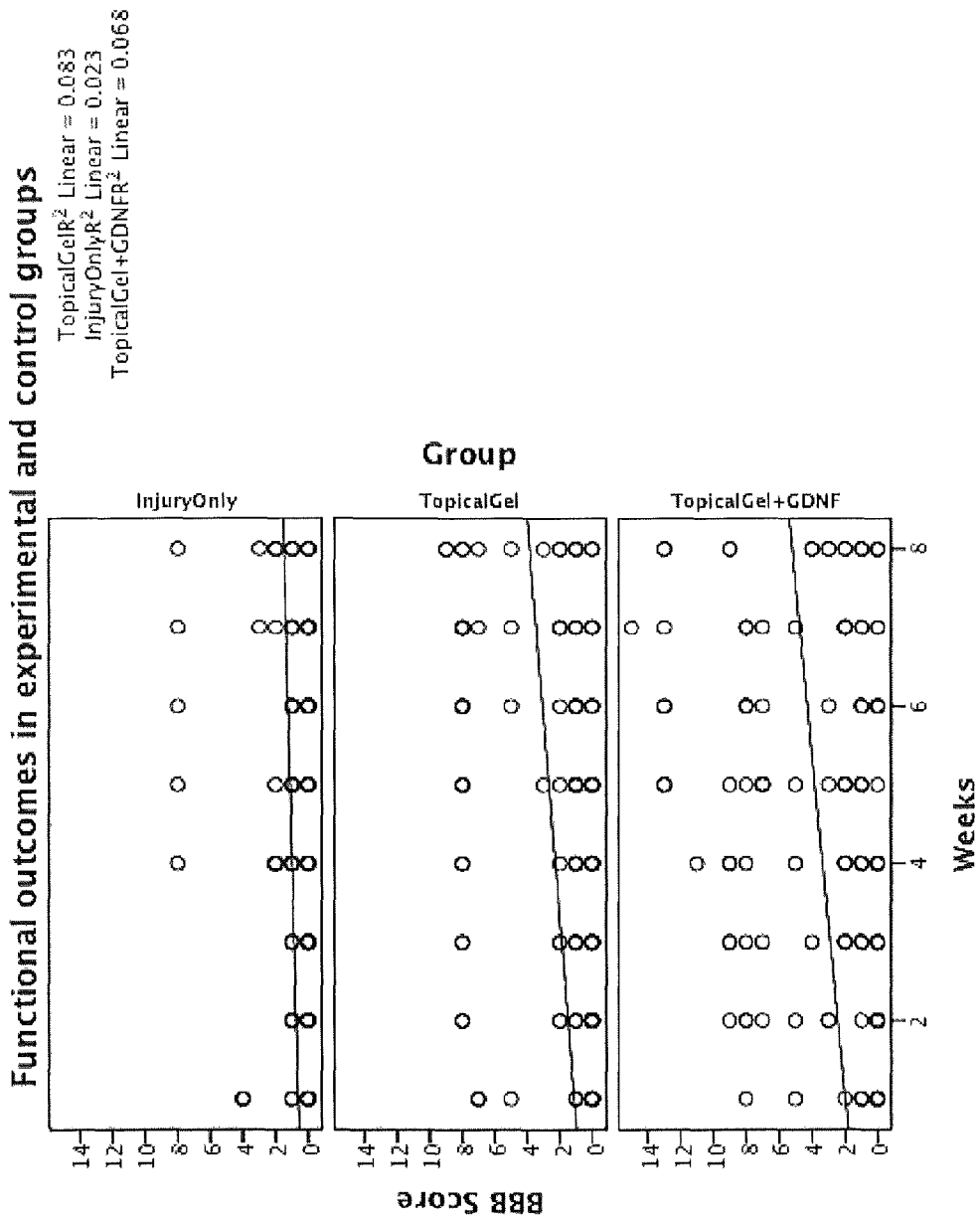
FIG. 12. Scatter plots depicting functional outcomes.
Figure 13:
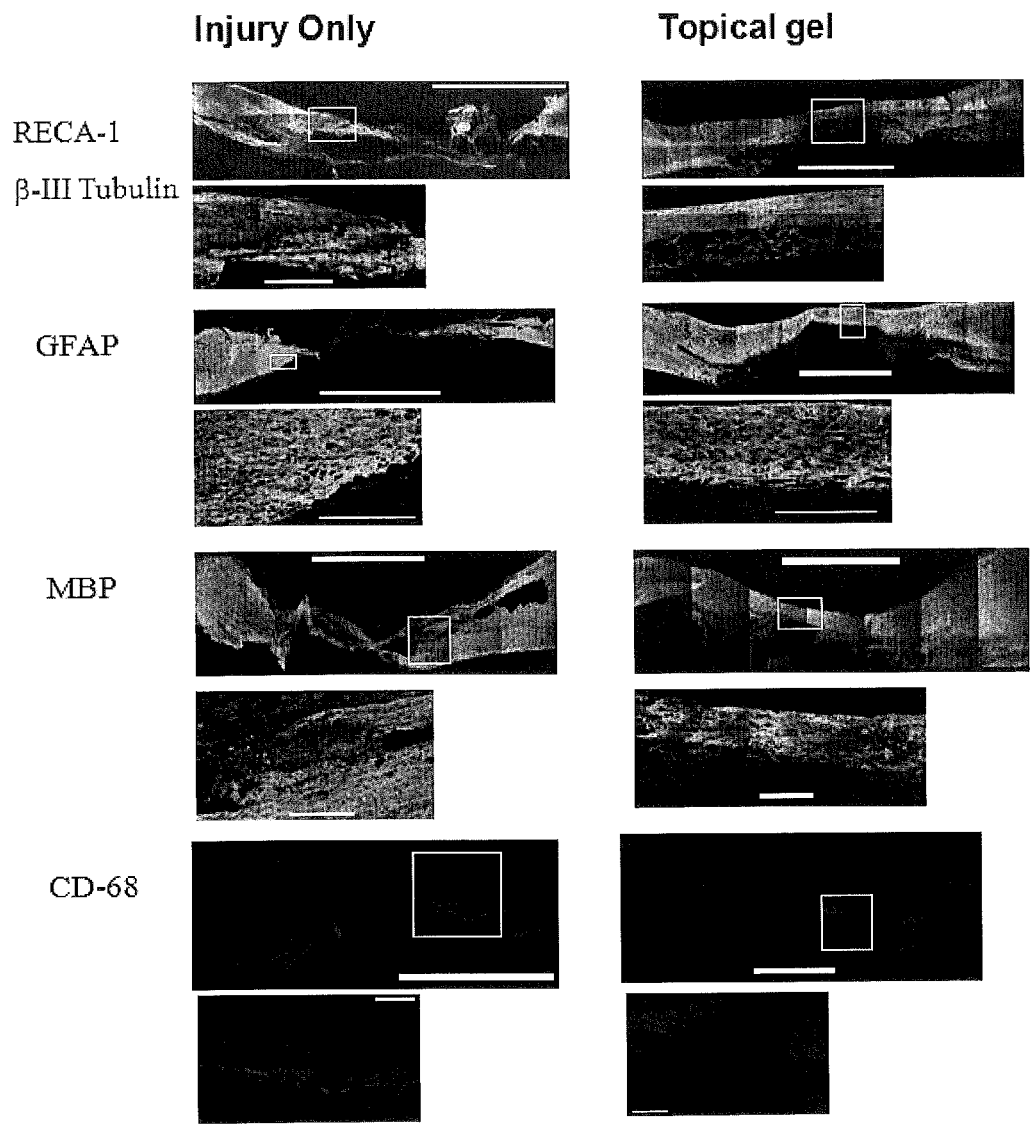
FIG. 13. Immunostaining in control and topical gel groups.

Improvement in BBB scores was observed in treatment groups as early as the first week (FIG. 12). The mean BBB scores for control group at eight weeks was 1.67 (95% CI 0.39-2.95). The topical hydrogel application significantly improved functional recovery (BBB score of topical gel group—4 (95% CI 1.9-6.1). The functional scores were comparable after the inclusion of GDNF (BBB score—4.06 (95% CI 2.07-6.05)). Immunostaining (FIG. 13) demonstrates a tissue bridge with abundant blood vessels and myelinated axons across the injury area. Although there is evidence of inflammation in the tissue bridge the distribution of astrocytes is relatively uniform and is comparable to sham animals.

Conclusions

The topical chitosan-gelatin topical hydrogel improves functional outcomes when used alone or in combination with GDNF after severe spinal cord injury in rats. This treatment strategy appears to preserve axons across injury site and prevent the formation of astroglial scar. Decreased astrogliosis and scar formation; preservation of axons, vasculature and myelination across the injury epicenter; and increased regeneration across the injury epicenter were all observed with topical hydrogel application. Topical application of hydrogel improved hind limb function in rats after 8 weeks follow up.

Example 13

Functional Outcomes After Application of Chitosan-Gelatin Hydrogel in a Rat Model of Severe Spinal Cord Injury Introduction A thermo-sensitive, biodegradable chitosan-gelatin hydrogel for neuroprotection and growth factor delivery after neurotrauma was designed. The functional outcomes were evaluated after application of the hydrogel in a rat model of severe spinal cord injury.

Methods

Adult SD rats were randomly assigned to a control (spinal cord injury only) and four experimental groups (hydrogel injection, hydrogel with GDNF injection, topical hydrogel and topical hydrogel with GDNF). Severe spinal cord injury was induced by a computer-controlled impactor. In the injection group, hydrogel solution was administered slowly within the injury site while it was placed on the cord surface in the topical group. All animals were followed for 8 weeks and weekly behavioral testing was performed using the BBB scale (minimum 0, maximum 21). Immunohistochemistry was performed to study scar formation and tissue preservation.

Results

The application of hydrogel did not adversely affect the functional outcomes. The BBB scores were better in the topical group as compared to the injection group. Inclusion of GDNF, both in topical and injection groups, appears to improve functional outcomes. Immunohistochemistry revealed preservation of neuronal bridge across the injury epicenter.

Conclusion

The application of chitosan-gelatin hydrogel improves functional outcomes when combined with GDNF in a rat model of severe spinal cord injury.

Example 14

Engineering an in Situ Crosslinkable Hydrogel for Enhanced Remyelination

Introduction. Demyelination is the pathological process in which myelin sheaths are lost from around axons. The loss of myelin sheaths is associated with conduction block, progressive axonal and neuronal loss, and functional deficits. In addition to focal demyelinating diseases, such as multiple sclerosis (MS), and leukodystrophies, axonal demyelination is an inevitable component in many types of neural tissue injury, including spinal cord injury, and traumatic brain injury. Remyelination has to occur in order to cure these diseases, and to fully regenerate injured spinal cords or brain tissues.

At present, there are no effective therapies that promote remyelination. Existing immunosuppressive and immunomodulatory treatments have little efficacy in either preventing long-term disability or in restoring lost functions[1]. Since remyelination involves the generation of new mature oligodendrocytes, current research strategies for remyelination in animal models have been focused on oligodendrogenic stem/precursor cells of both endogenous and exogenous origins[2, 3]. Previous studies on the role of oligodendrocytes and oligodendrocyte progenitors in CNS remyelination have evidenced the dominant contribution of oligodendrocyte precursor cells (OPCs) to remyelinate spinal cord lesions. Although spontaneous remyelination mediated by endogenous OPCs can be a highly effective regenerative process, this response is incomplete and fails over time due to the limited availability, migratory capacity, and myelinating ability[4, 5]. In contrast, cell transplantation (exogenous therapies) using glial cell lineages or precursors including OPCs[6], induced pluripotent stem cells[7], mesenchymal stem cells[8], neural stem cells[9], embryonic stem cell-derived precursors[10], and olfactory ensheathing cells[11], have all been shown to achieve some remyelination in demyelinated adult CNS.

The fate of transplanted cells is strongly influenced by the type of diseases/injuries and local microenvironmental signals (biomechanical and biomolecular signals). As to remyelination failure, the scarring and inflammatory tissue environment at the demyelinating site may be deleterious to the survival and directed differentiation of transplanted cells with the presence of differentiation block of oligodendroglial progenitors in chronic MS lesions[1,2,5, 14-16]. Control over stem cell trafficking, survival, proliferation, and differentiation within a complex demyelinating in vivo milieu continues to be extremely challenging.

Figure 14:
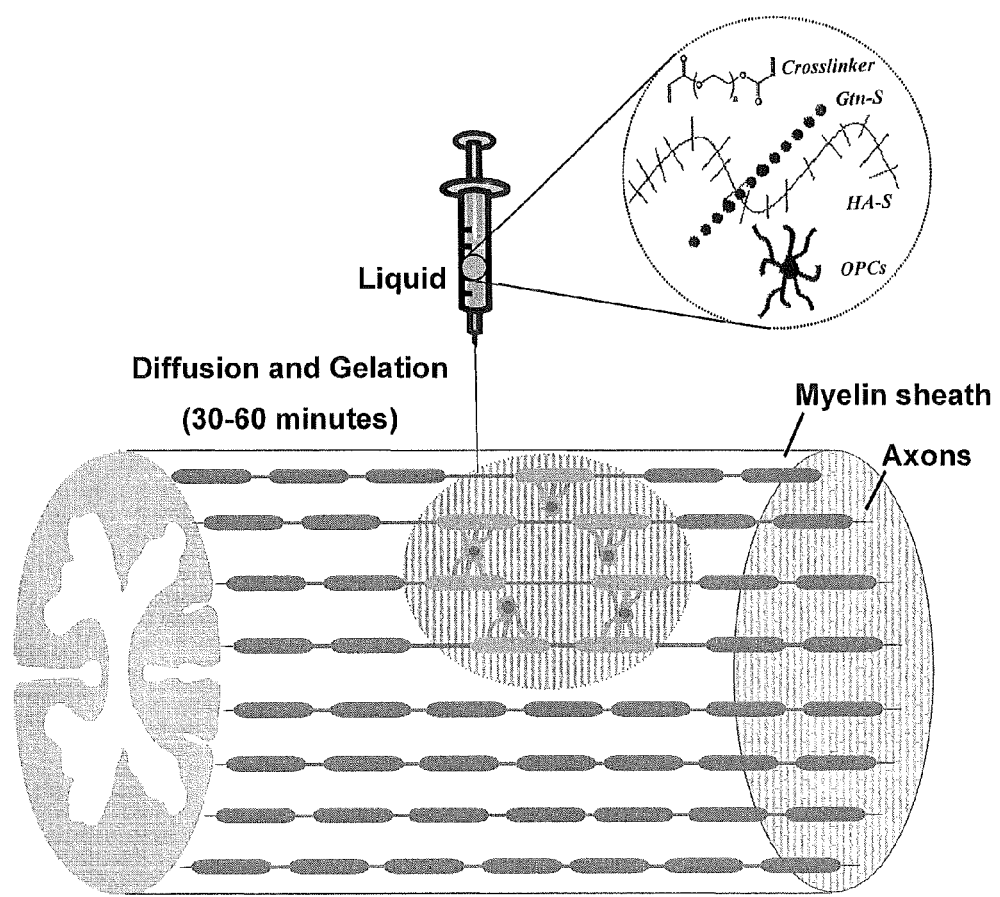
FIG. 14. Schematic drawing of OPCs transplanted with in-situ crosslinkable hydrogels for spinal cord remyelination.

The overall objective of this study was to engineer an injectable biocompatible hydrogel system as a supportive niche to provide a regeneration permissive microenvironment for transplanted OPCs to survive, functionally differentiate, and remyelinate central nervous system (CNS) lesions. The system employs a highly biocompatible hydrogel, based on thiol functionalized hyaluronic acid (HA-S) and thiol functionalized human recombinant gelatin (Gtn-S), which can be crosslinked by poly (ethylene glycol) diacrylate (PEGDA) through Michael-type addition reaction. This hydrogel system was engineered regarding cell adhesive properties and mechanical properties to best support the growth properties of OPCs in culture. Transplanted OPCs with the hydrogels optimized in vitro exhibited enhanced survival, and oligodendrogenic differentiation, and were able to remyelinate demyelinated axons inside ethidium bromide (EB) demyelination lesion in adult spinal cord. The schematic drawing of OPCs transplanted with in-situ crosslinkable hydrogels for spinal cord remyelination is shown in FIG. 14. This study demonstrates extensive remyelination with transplanted stem cells and provides a new treatment for demyelination-related diseases and CNS injuries in which cell therapies may be beneficial.

Figure 15:
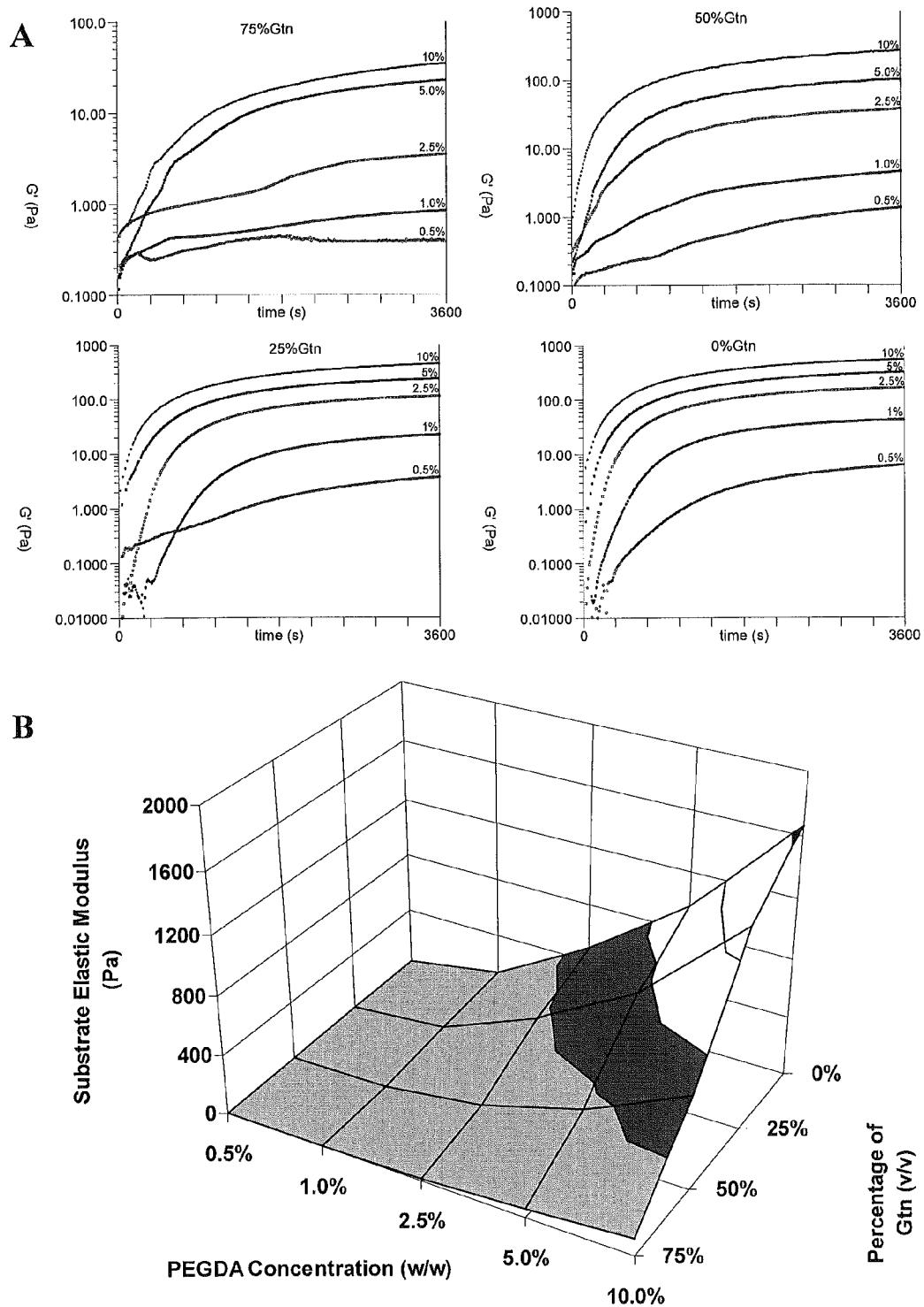
FIGS. 15A-B. (A) Time sweep of G' as a function of PEGDA concentration (10%, 5%, 2.5%, 1% and 0.5%) and Gtn-S percentage (75%, 50%, 25%, and 0%). (B) the elastic modulus of the hydrogel as a function of PEGDA concentration and Gtn-S percentage.

Mechanical Property of Hydrogel. To develop CNS-compatible hydrogels to be used as cell carriers in the adult CNS, it is appropriate to ensure the mechanical compliance of the hydrogels with native CNS tissue. The storage modulus (G') of rat CNS is about 40 Pa or elastic modulus (E') of around 120 Pa as characterized by rheometer. Note that the storage modulus G' always exceeds the loss modulus G", indicating that the adult rat CNS has an elasticity-dominant rather than viscosity-dominant mechanical property, which is in agreement with previous studies[24]. The mechanical properties of this hydrogel system can be controlled by varying a couple of parameters, such as the concentrations of HA-S and Gtn-S, the ratio of HA-S to Gtn-S, PEGDA concentration, and so on. In this study, the effects of two parameters, i.e., Gtn-S percentage, and PEGDA concentration on hydrogel properties and OPC behaviors are examined. Each of the two parameters was examined independently while keeping other variables constant. By varying the gelatin percentages, or PEGDA concentrations, hydrogels with elastic modulus ranging from 1 Pa to 1600 Pa, which spans the range of that of native CNS tissue (120 Pa), can be achieved (FIG. 15). The gelatin percentage and PEGDA concentration exhibited opposing effects on the hydrogel elastic modulus, i.e., E' increases as a function of decreasing Gtn-S percentage, whereas E' increases with increasing PEGDA concentration. Since PEGDA acts as the crosslinker for the hydrogel system, E' increases with the increasing PEGDA concentration. The cell adhesive component in the hydrogel, Gtn-S, contributes to the viscosity rather than the elasticity of the hydrogels.

Optimizing Hydrogels for OPCs Culture. Extracellular matrix (ECM) is an important component for the stem cell niche and regulating stem cell behavior and functions. Biomaterials can be used to create a niche to support stem cell survival in vivo by providing the biochemical and biomechanical environments for the tissues to be regenerated. Hyaluronic acid (HA) is an important EMC component for CNS tissues. Inclusion of HA imparts hydrophilic network structures to the hydrogels. However, HA is extremely hydrophilic and polyanionic, which prevents cell attachment and limits its ability to support cell growth and tissue remodeling. To promote cell growth and function, cell adhesive component, human recombinant gelatin, was incorporated in the hydrogel. The effect of biochemical and biomechanical properties of the hydrogels on OPC attachment, proliferation, and directed differentiation were examined in vitro and in vivo.

Figure 16:
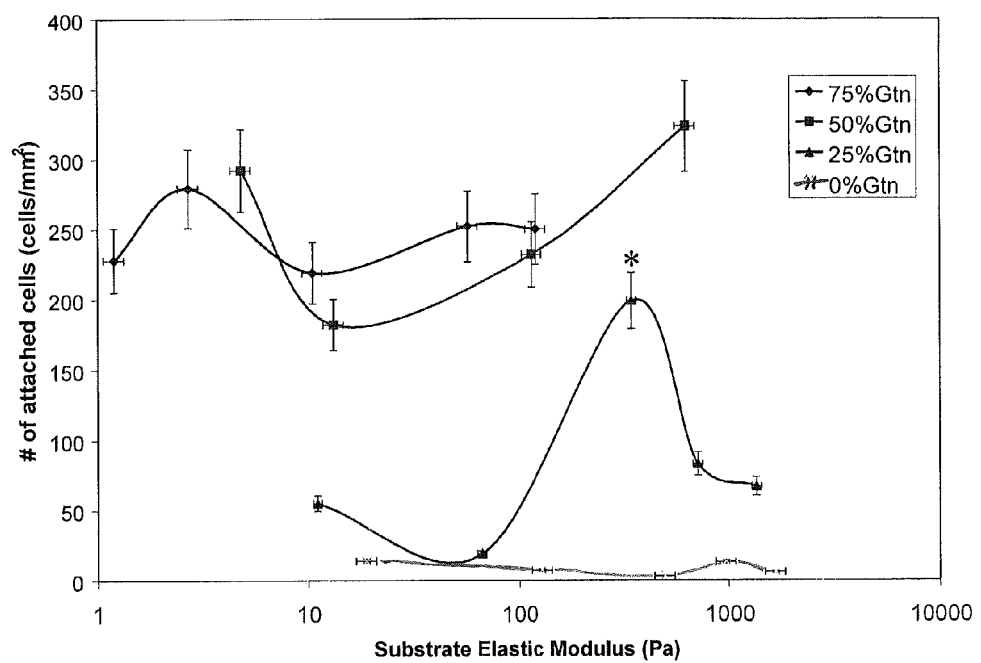
FIG. 16. The numbers of attached OPCs on the surfaces of the hydrogels as a function of hydrogel elastic modulus and Gtn-S content. On the hydrogels with 25% GTn-S, OPCs preferred to attach on hydrogels of medium stiffness ($*P<0.05$).

The effect of the adhesive component Gtn-S in the hydrogels on OPC behavior, such as attachment, morphology, and proliferation, was evaluated by culturing OPCs on the surfaces of the hydrogels with different gelatin content and elastic modulus. When compared to that of the elastic modulus, Gtn-S content in the hydrogels exerted greater effect on cell attachment, as evidenced by magnitude-higher numbers of attached OPCs on hydrogels with high Gtn-S content (exceeding 50%) relative to those with low Gtn-S content (FIG. 16). At low Gtn-S percentages (25%), the numbers of attached OPCs were dependent on hydrogel elastic modulus, manifested by the appearance of a peak on the curve. In comparison, at high Gtn-S percentages (50%), OPC attachment was independent of the elastic modulus with the curves almost flattened over the elastic modulus. These results suggest that when adhesive components present at sufficiently high percentages in the hydrogels, cell adhesive component may dominate over material mechanical properties and dictate cell attachment. There was no significant difference in OPC attachment between the 50% and 75% gelatin groups, perhaps due to the saturation in the presentation of surface binding domains by high-percentage Gtn-S in the hydrogels. Given the range of elastic modulus achieved with each value of gelatin percentage, OPC attachment was best favored on the surfaces of the hydrogels with 50% Gtn-S.

Parallel investigations of the morphologies of attached OPCs on hydrogels of the same elastic modulus (10 Pa) but with different gelatin percentages revealed no significant difference among the groups. All the attached cells displayed spreading cytoskeletons (red is the staining for A2B5, a specific surface marker for OPCs). The proliferation of attached OPCs on hydrogel surfaces was examined using Click iT-EdU kit. All the attached OPCs on the hydrogel surfaces were stained in red using PI, while the proliferating OPCs were stained in blue using Click iT-EdU 647. Regardless of the gelatin percentage, attached OPCs exhibited an approximate 5% proliferation rate (blue to red cell ratio).

Hydrogel Stiffness Affects Cell Behaviors. OPCs were cultured on the surfaces and inside the hydrogels, representing 2D and 3D culture conditions, respectively. At 3 days in 2D culture (on the surfaces of the hydrogels), OPCs exhibited a biphasic change in morphology over increasing elastic modulus of the hydrogels. On soft hydrogels (4.8 Pa and 13.8 Pa), OPCs displayed round morphology with very few spreading processes. On hydrogels of medium stiffness (116 Pa), OPCs were primarily spreading resembling the natural morphology of OPCs in the body, which is important for oligodendrocytes to spirally enwrap axons, forming multi-lamellar myelin sheaths. On stiff hydrogels (624 Pa), cell spreading was diminished over hydrogel stiffness with OPCs assuming round morphology in cell aggregates. A similar trend of biphasic change was observed in cell morphology vs. hydrogel stiffness at 7 days in 2D culture. OPCs were increasingly spreading with sprouting processes within low to medium range of hydrogel elastic modulus, and were then progressively aggregated and assumed round morphology within medium to high range of hydrogel elastic modulus.

In parallel, OPCs survived in 3D culture (i.e., inside the hydrogels). The viability of OPCs was high (>98%) regardless of the hydrogel elastic modulus (4.8 Pa, 13.8 Pa, 116 Pa, 312 Pa and 624 Pa tested). However, OPCs expressed normal oligo-morphology with hydrogel elastic modulus less than 120 Pa. Hydrogels with higher elastic modulus led to spherical structures of OPCs without sprouting processes. These hydrogels may be too stiff to allow processes sprouting and extension for the OPCs[25].

Cell adhesion and proliferation are important indices to evaluate the appropriateness of a cell carrier to support cell functions. As a function of the hydrogel elastic modulus, the proliferation rate of cultured OPCs on the surfaces of the hydrogels increased when the modulus is lower than 120 Pa and decreased when the modulus is greater than 120 Pa. Hydrogel with a 120 Pa elastic modulus, which is close to that of native CNS tissue, best supports OPC proliferation.

OPC Transplantation with Optimized Hydrogels as Carrier. OPCs are most often referred to as a population of adult CNS stem/precursor cells that are capable of differentiating into mature oligodendrocytes[26]. Lines of evidence on the contribution of OPCs as the major source of remyelinating oligodendrocytes have come from studies through in vivo tracing of both endogenous OPCs[4,27] and transplanted OPCs. Complementary studies on mature oligodendrocytes have suggested their inability to contribute to remyelination in adult CNS, further supporting the role of OPCs as the primary cell source for functional remyelination. To remyelinate the axons, OPCs have to establish contact with the axon to be remyelinated, express myelin genes, and form a myelin membrane which then ensheaths the axon. In addition to a deficiency of differentiation-inducing factors, a demyelinating tissue environment presents inhibitory factors that are responsible for differentiation failure[15,28]. The demyelination model was established by the injection of EB at the left ventrolateral funiculus of the rat spinal cords, which leaves a population of demyelinated axons in a glial-depleted environment. OPCs were transplanted to the EB demyelinated lesion area in two treatment groups, i.e., OPCs only, and OPCs with optimized hydrogel carrier. When compared to the untreated control group (demyelinated lesion+saline injection) in which the demyelinated area remained as a substantial cavity, both treatment groups displayed cell populations at the lesion site, as evidenced by the presence of cell nuclei. In particular, the lesion site in the OPCs with optimized hydrogel group was much more densely repopulated by myelin basic protein (MBP)-positive oligodendrocytes (indicated by the presence of numerous circle-shaped MBP-positive structures typical of normal myelination) when compared to that in the OPCs only treatment group, where very few MBP-positive cells were seen within the lesion site. A few GFAP-positive astrocytes were seen in both treatment groups. The absence of cells at the lesion site in the untreated control suggests that the cells seen at the lesion in the two treatment groups were primarily transplanted cells rather than of endogenous origin. The hydrogel carrier has protected transplanted OPCs within a hostile demyelinated lesion environment for better survival and overcomes environmental cues that normally restrict the differentiation potential of transplanted OPCs, which may have facilitated OPCs differentiation into mature oligodendrocytes.

Conclusions. A hydrogel system has been developed as a candidate material for OPC niche formation. This study demonstrates extensive remyelination with transplanted stem cells in vivo. The hydrogel harnesses the potential of exogenous OPCs for CNS remyelination by promoting the survival, attachment, natural morphology, proliferation, oligodendrogenic differentiation, and myelin formation of transplanted OPCs in a demyelinated CNS lesion environment. This work exemplifies the efforts to develop material equivalents to the stem/precursor cell niche through engineering strategies based upon an integration of material properties with neural compatible biochemical and biomechanical properties. This study demonstrates the engineering of neural compatible hydrogels as a niche for OPCs to promote remyelination in vivo. The results indicate that human recombinant gelatin benefits OPC attachment without significant effect on OPC proliferation and morphology. Hydrogel elastic modulus affects the overall cell morphology and an optimal range of elastic modulus exists that best supports the natural oligo-morphology, and proliferation of OPCs in both 2D and 3D cultures. OPCs transplanted with hydrogels optimized with cell adhesive properties and mechanical properties as determined in the in vitro experiments exhibited enhanced survival, oligodendrogenic differentiation, and the ability to remyelinate demyelinated axons inside demyelination lesion in adult spinal cord. This study provides a new therapeutic approach to treat demyelination related diseases and other trauma/disease conditions in which cell therapies may be beneficial or essential.

In-situ crosslinkable hydrogels and rheological testing. To test the mechanical properties of the formed hydrogel series, HA-S solution (1% w/v, Glycosan BioSystems Inc. Salt Lake City, Utah) and Gtn-S solution (1%, w/v, different Gtn ratio: 75%, 50%, 25% and 0%) with varying PEGDA concentrations (10%, 5%, 2.5%, 1%, and 0.5%) were inspected with oscillatory shear rheometer AR 1000 (TA Instruments Inc.). The time sweep was performed to monitor the in situ gelation at 37° C., recording the temporal evolution of shear storage modulus, G' and the shear loss modulus, G". Frequency sweep tests are used to obtain information about the stability of hydrogel structures[29]. The stress sweep was set up by holding the frequency 1 Hz constant while increasing the stress level from 1 to 10 Pa. The applied range of 1-10 Pa was found to be safe-for-use from a prior experiment where the linear viscoelastic region (LVR) profiles of the hydrogels were determined by shearing them until structural breakdown. Oscillatory stress sweep allows determination of G' of hydrogels. The elastic modulus, E', can be evaluated by $E'=2G'(1+\gamma)$. When a material can be assumed to be incompressible, its Poisson's ratio, γ, approaches 0.5 and this relationship approaches E'=3G'. This assumption for hydrogels is supported by research showing that n for polyacrylamide hydrogels is nearly 0.5, and because these hydrogels are typically used under very low strain conditions[30]. In addition to using a rheometer to test the mechanical properties of hydrogels, fresh adult rat CNS tissues were examined by rheometer using the same rheological protocol.

OPC culture. Oligodendrocyte progenitor cells (OPCs, CG4 cell[31]) were maintained with serum-free growth medium supplemented with platelet-derived growth factor (PDGF, 10 ng/mL) and fibroblast growth factor 2 (FGF2, 10 ng/mL). For 2D culture, OPCs were seeded on the surface of hydrogels at $5 \times 10^3$ cells/cm$^2$. For 3D culture, $1 \times 10^4$ cells/mL were mixed into the hydrogels.

Cell viability. Viability of cells was examined using a LIVE/DEAD Viability Kit (L-7013, Molecular Probes). Live cells were stained with green fluorescent SYTO 10; and dead cells with compromised cell membranes were stained with red fluorescent ethidium homodimer-2.

Cell morphology. Morphology of cells was examined by immunocytochemistry. The OPCs were fixed, stained with A2B5 (MsIgM, ab5321, abeam) and 4',6-Diamidino-2-Phenylindole, Dihydrochloride (DAPI, Molecular Probes), and visualized with a Leica TCS SP5 laser scanning confocal microscope. For each well, 5 images are taken from different regions.

Cell adhesion and proliferation. Proliferation of cells was examined using Click iT-EdU cell proliferation assay (C10085, Invitrogen). The total attached cells were detected by PI staining. The samples were imaged using a Leica TCS SP5 laser scanning confocal microscope. For each well, five images were taken from different regions. The percentage of EdU cells in the population was calculated and compared among groups.

Demyelinating lesion and transplantation of OPCs. An experimental model of toxin-induced focal demyelination using ethidium bromide (EB) to demyelinate specific CNS tracts in a dose-dependent manner[32] was used. A total of 21 female nude rats (150-200 g, Charles River Laboratories) were used throughout the study. The EB model of focal demyelination induced by injecting EB at left ventral white matter of the thoracic spinal cord was conducted as previously described. All transplantations were performed 7 day post-surgery. Following induction of anesthesia, T8/T9 laminectomy site was re-exposed. OPCs ($1 \times 10^5$ cells/uL) were transplanted in two treatment groups: (1) OPCs only, (2) OPCs with optimized hydrogels. OPCs were delivered at a rate of 0.5 μL/min directly into the EB lesion using the stereotactic coordinates.

Tissue processing and immunohistochemistry. To evaluate OPCs transplanted following demyelination, animals were sacrificed at 4 weeks post transplantation. 20 μm thick transverse sections were cut and stained with glial fibrillary acidic protein (GFAP) for astrocytes (1:1000; Dako), myelin basic protein (MBP) for mature oligodendrocytes (1:500, abeam), and β III tubulin for axons (1:1000; Sigma). The specimens were imaged using a Leica TCS SP5 laser scanning confocal microscope.

Statistical Analysis. Data were presented as the mean±the standard error of mean for each group. One-way analysis of variance (ANOVA) was performed to determine the effect of hydrogel property and hydrogel use on the outcome using SPSS software. Statistical significance is accepted at $P<0.05$.

REFERENCES FOR EXAMPLE 14

[1] T. Ben-Hur, S. A. Goldman, *Ann. N.Y. Acad. Sci.* 2008, 1142, 218.

[2] J. Yang, A. Rostami, G. X. Zhang, *J. Neurol. Sci.* 2009, 276, 1.

[3] J. Jadasz, L. Aigner, F. Rivera, P. Küry, *Cell Tissue Res.* 2012.

[4] B. E. Deverman, P. H. Patterson, *J. Neurosci.* 2012, 32, 2100.

[5] M. R. Kotter, C. Stadelmann, H.-P. Hartung, *Brain* 2011, 134, 1882.

[6] Q. Cao, Q. He, Y. Wang, X. Cheng, R. M. Howard, Y. Zhang, W. H. DeVries, C. B. Shields, D. S. K. Magnuson, X.-M. Xu, D. H. Kim, S. R. Whittemore, *J. Neurosci,* 2010, 30, 2989.

[7] O. Tsuji, K. Miura, Y. Okada, K. Fujiyoshi, M. Mukaino, N. Nagoshi, K. Kitamura, G. Kumagai, M. Nishino, S. Tomisato, H. Higashi, T. Nagai, H. Katoh, K. Kohda, Y. Matsuzaki, M. Yuzaki, E. Ikeda, Y. Toyama, M. Nakamura, S. Yamanaka, H. Okano, *PNAS* 2010, 107, 12704.

[8] D. Gordon, G. Pavlovska, J. B. Uney, D. C. Wraith, N. J. Scolding, *J. Neuropathol. Exp. Neurol.* 2010, 69, 1087.

[9] O. Einstein, Y. Friedman-Levi, N. Grigoriadis, T. Ben-Hur, *J. Neurosci.* 2009, 29, 15694.

[10] M. Aharonowiz, O. Einstein, N. Fainstein, H. Lassmann, B. Reubinoff, T. Ben-Hur, *PLoS ONE* 2008, 3, e3145.

[11] M. Sasaki, K. L. Lankford, C. Radtke, O. Honmou, J. D. Kocsis, *Exp. Neurol.* 2011, 229, 88.

[12] T. Kuhlmann, V. Miron, Q. Cuo, C. Wegner, J. Antel, W. Bruck, *Brain* 2008, 131, 1749.

[13] E.-M. Hur, I. H. Yang, D.-H. Kim, J. Byun, Saijilafu, W.-L. Xu, P. R. Nicovich, R. Cheong, A. Levchenko, N. Thakor, F.-Q. Zhou, *PNAS* 2011, 108, 5057.

[14] M. Zawadzka, R. J. M. Franklin, *Curr. Opin. Neurol.* 2007, 20, 294.

[15] Y. Wang, X. Cheng, Q. He, Y. Zheng, D. H. Kim, S. R. Whittemore, Q. L. Cao, *J. Neurosci.* 2011, 31, 6053.

[16] K. S. Carbajal, C. Schaumburg, R. Strieter, J. Kane, T. E. Lane, *PNAS* 2010, 107, 11068.

[17] M. C. Cushing, K. S. Anseth, *Science* 2007, 316, 1133.

[18] D. E. Discher, D. J. Mooney, P. W. Zandstra, *Science* 2009, 324, 1673.

[19] A. Mammoto, K. M. Connor, T. Mammoto, C. W. Yung, D. Huh, C. M. Aderman, G. Mostoslaysky, L. E. H. Smith, D. E. Ingber, *Nature* 2009, 457, 1103.

[20] M. W. Tibbitt, K. S. Anseth, *Biotechnol. Bioeng.* 2009, 103, 655.

[21] R. A. Marklein, J. A. Burdick, *Adv. Mater.* 2010, 12, 175.

[22] Z. Liu, H. Wang, Y. Wang, Q. Lin, A. Yao, F. Cao, D. Li, J. Zhou, C. Duan, Z. Du, Y. Wang, C. Wang, *Biomaterials* 2012, 33, 3093.

[23] M. Habib, K. Shapira-Schweitzer, O. Caspi, A. Gepstein, G. Arbel, D. Aronson, D. Seliktar, L. Gepstein, *Biomaterials* 2011, 32, 7514.

[24] Y.-B. Lu, K. Franze, G. Seifert, C. Steinhäuser, F. Kirchhoff, H. Wolburg, J. Guck, P. Janmey, E.-Q. Wei, J. Käs, A. Reichenbach, *PNAS* 2006, 103, 17759.

[25] M. J. Mahoney, K. S. Anseth, *Biomaterials* 2006, 27, 2265.

[26] F. J. Sim, J. K. Lang, B. Waldau, N. S. Roy, T. E. Schwartz, W. H. Pilcher, K. J. Chandross, S. Natesan, J. E. Merrill, S. A. Goldman, *Ann Neurol* 2006, 59, 763.

[27] K. S. Carbajal, J. L. Miranda, M. R. Tsukamoto, T. E. Lane, *Glia* 2011, 59, 1813.

[28] D. E. Discher, P. Janmey, Y.-l. Wang, *Science* 2005, 310, 1139.

[29] K. Ghosh, X. Z. Shu, R. Mou, J. Lombardi, G. D. Prestwich, M. H. Rafailovich, R. A. F. Clark, *Biomacromolecules* 2005, 6, 2857.

[30] T. Boudou, J. Ohayon, C. Picart, P. Tracqui, *Biorheology* 2006, 43, 721.
[31] J. C. Louis, E. Magal, D. Muir, M. Manthorpe, S. Varon, *J Neurosci Res* 1992, 31, 193.
[32] R. H. Woodruff, R. J. M. Franklin, *Glia* 1999, 25, 216.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method of treating a spinal cord injury, comprising topically delivering to the spinal cord injury site an amount of a neurotrophic factor and/or an anti-inflammatory agent effective to treat the spinal cord injury, wherein the neurotrophic factor and/or the anti-inflammatory agent is in a hydrogel comprising chitosan, gelatin and a crosslinker, wherein the hydrogel is delivered to the spinal cord injury site as a liquid and gels in situ.

2. The method of claim 1, wherein the spinal cord injury is an acute spinal cord injury.

3. The method of claim 1, wherein the hydrogel comprises a covalent crosslinker and an ionic crosslinker.

4. The method of claim 3, wherein the covalent crosslinker is genipin.

5. The method of claim 3, wherein the ionic crosslinker is glycerol phosphate.

6. The method of claim 3, wherein the covalent crosslinker is added to a chitosan and gelatin mixture prior to addition of the ionic crosslinker.

7. The method of claim 1, wherein the neurotrophic factor is glial derived neurotrophic factor (GDNF).

8. A method of treating a spinal cord injury, comprising topically delivering to the spinal cord injury site an amount of a hydrogel effective to treat the spinal cord injury, wherein the hydrogel comprises chitosan, gelatin and a crosslinker, wherein the hydrogel is delivered to the spinal cord injury site as a liquid and gels in situ.

9. The method of claim 8, wherein the spinal cord injury is an acute spinal cord injury.

10. The method of claim 8, wherein the hydrogel comprises a neurotrophic factor and/or an anti-inflammatory agent.

11. The method of claim 10, wherein the neurotrophic factor is glial derived neurotrophic factor (GDNF).

12. A method of reducing inhibition of axonal regeneration at a spinal cord injury site, comprising topically delivering to the site an amount of a hydrogel effective in reducing inhibition of axonal regeneration at the spinal cord injury site, wherein the hydrogel comprises chitosan, gelatin and a crosslinker, wherein the hydrogel is delivered to the spinal cord injury site as a liquid and gels in situ.

13. The method of claim 12, wherein the hydrogel comprises a neurotrophic factor and/or an anti-inflammatory agent.

14. The method of claim 13, wherein the neurotrophic factor is glial derived neurotrophic factor (GDNF).

15. A method of decreasing secondary injury at a spinal cord injury site, comprising topically delivering to the site an amount of a hydrogel effective in decreasing secondary injury at the spinal cord injury site, wherein the hydrogel comprises chitosan, gelatin and a crosslinker, wherein the hydrogel is delivered to the spinal cord injury site as a liquid and gels in situ.

16. The method of claim 15, wherein the spinal cord injury is an acute spinal cord injury.

17. The method of claim 15, wherein the hydrogel comprises a neurotrophic factor and/or an anti-inflammatory agent.

18. The method of claim 17, wherein the neurotrophic factor is glial derived neurotrophic factor (GDNF).

* * * * *

UNITED STATES PATENT AND TRADEMARK OFFICE
CERTIFICATE OF CORRECTION

PATENT NO. : 8,680,182 B2
APPLICATION NO. : 13/447041
DATED : March 25, 2014
INVENTOR(S) : Jin et al.

Page 1 of 1

It is certified that error appears in the above-identified patent and that said Letters Patent is hereby corrected as shown below:

In the Specification:

Column 1, line 27: Please correct "9662-4IP_$_{ST}$25.txt,"
to read -- 9662-4IP_ST25.txt, --

Column 5, lines 61-62: Please correct "CDPVCC GTARPGYIGSRGTARCCAC,"
to read -- CDPVCC GTARPG<u>YIGS</u>RGTARCCAC, --

Column 15, lines 48-49:
Please correct "Vernadakis, A., editors. Astrocytes.
Orlando: Academic Press; 1986 p 231-262), acts as a"
to read -- Vernadakis, A., editors. Astrocytes. Orlando: Academic Press;
1986 p 231 -262), acts as a --

Column 21, lines 45-46: Please correct "CDPVCC GTARPGYIGSRGTARCCAC,"
to read -- CDPVCC GTARPG<u>YIGS</u>RGTARCCAC, --

Column 34, lines 54-55:
Please correct "oscillatory shear rheometer AR 1000 (TA
Instruments Inc.). The time sweep was performed to moni-"
to read -- oscillatory shear rheometer AR 1000 (TA Instruments Inc.). The
time sweep was performed to moni- --

Signed and Sealed this
Fifteenth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,680,182 B2  Page 1 of 1
APPLICATION NO. : 13/447041
DATED : March 25, 2014
INVENTOR(S) : Jin et al.

It is certified that error appears in the above-identified patent and that said Letters Patent is hereby corrected as shown below:

Column 1, Line 15 STATEMENT OF GOVERNMENT SUPPORT:
Please replace the entire paragraph to read as follows:

-- This invention was made with government support under Grant No. R01 NS050243 awarded by the National Institutes of Health and Grant Number W81XWH-10-1-0954 awarded by the Department of Defense. The government has certain rights in the invention. --

Signed and Sealed this
Sixth Day of October, 2015

Michelle K. Lee
*Director of the United States Patent and Trademark Office*